US012779231B2

(12) United States Patent
Tieu et al.

(10) Patent No.: US 12,779,231 B2
(45) Date of Patent: Nov. 3, 2026

(54) DEVICES, SYSTEMS AND METHODS THAT SELECT ELECTRODE VECTOR FOR CONDUCTIVE COMMUNICATION BETWEEN EXTERNAL DEVICE AND IMPLANTABLE MEDICAL DEVICES

(71) Applicant: Pacesetter, Inc., Sylmar, CA (US)

(72) Inventors: Thanh Tieu, Simi Valley, CA (US); Robert Williams, San Jose, CA (US); Yongjian Wu, San Jose, CA (US); Jun Yang, Valencia, CA (US); Mei Phelps, Newbury Park, CA (US); Arash Azarmi, Pasadena, CA (US); Jenny Huang, San Jose, CA (US); Min Yang, Los Altos, CA (US); Hussain Fatakdawala, Milpitas, CA (US); Dulip Kaluarachchi, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 76 days.

(21) Appl. No.: 19/062,363

(22) Filed: Feb. 25, 2025

(65) Prior Publication Data

US 2025/0303179 A1 Oct. 2, 2025

Related U.S. Application Data

(60) Provisional application No. 63/570,205, filed on Mar. 26, 2024.

(51) Int. Cl.
*A61N 1/372* (2006.01)
*A61N 1/37* (2006.01)

(52) U.S. Cl.
CPC ....... *A61N 1/37241* (2013.01); *A61N 1/3706* (2013.01)

(58) Field of Classification Search
CPC .............. A61N 1/3706; A61N 1/37241; A61N 1/37252; A61N 1/37288
See application file for complete search history.

(56) References Cited

U.S. PATENT DOCUMENTS 4,891,812 A 1/1990 Bocci
7,925,343 B1 4/2011 Min et al.
(Continued)

OTHER PUBLICATIONS

Extended European Search Report dated Dec. 1, 2023, European Patent Application No. 23183888.9.
(Continued)

*Primary Examiner* — Scott Luan
(74) *Attorney, Agent, or Firm* — Pearl Cohen LLP

(57) ABSTRACT

While an external device is not in an active conductive communication session with one or more IMD(s), a test vector is selected and used to search for advertisement sequence(s) transmitted by the IMD(s) during an OOS search window. If the advertisement sequence(s) is/are not detected using the test vector during the OOS search window, another electrode combination is selected and used as the test vector. In response the advertisement sequence(s) being detected, an active conductive communication session is established with the IMD(s) and a respective score is determined. Then different combinations of other ones of the external electrodes are used as the test vector during an accelerated search window having a duration shorter than the OOS search window, and a respective score is determined for each of the other test vectors. Based on the scores,
(Continued)

a preferred vector is selected and used to perform further conductive communication with the IMD(s).

20 Claims, 16 Drawing Sheets

(56) References Cited

U.S. PATENT DOCUMENTS

| | | | |
|---|---|---|---|
| 9,656,091 | B2 | 5/2017 | Huelskamp et al. |
| 10,143,847 | B1 | 12/2018 | Edmonson et al. |
| 10,213,610 | B2 | 2/2019 | Maile et al. |
| 10,722,720 | B2 | 7/2020 | Stahmann et al. |
| 10,835,753 | B2 | 11/2020 | Koop et al. |
| 2010/0114209 | A1 | 5/2010 | Krause |
| 2015/0196758 | A1 | 7/2015 | Stahmann et al. |
| 2016/0007873 | A1 | 1/2016 | Huelskamp |
| 2016/0030757 | A1 | 2/2016 | Jacobson |
| 2016/0038747 | A1 | 2/2016 | Maile |
| 2017/0215731 | A1 | 8/2017 | Huelskamp et al. |
| 2017/0319863 | A1 | 11/2017 | Thompson-Nauman et al. |
| 2019/0184181 | A1 | 6/2019 | Zhao et al. |
| 2021/0236827 | A1 | 8/2021 | Jiang et al. |
| 2021/0402190 | A1 | 12/2021 | Zhang et al. |
| 2022/0212019 | A1* | 7/2022 | Lee .................... A61N 1/37217 |
| 2024/0382766 | A1 | 11/2024 | Sprowls et al. |
| 2024/0382769 | A1 | 11/2024 | Sprowls et al. |

OTHER PUBLICATIONS

Response to Invitation pursuant to Rules 70a(1) EPC dated Jun. 17, 2024, European Patent Application No. 23183888.9.

Breeman, Karel T.N., et al., "Long-term performance of a novel communicating antitachycardia pacing-enabled leadless pacemaker and subcutaneous implantable cardioverter-defibrillator system: a comprehensive prelinical study," Heart Rhythm Society, [https://doi.org/10.1016/j.hrthm.2022.01.024], May 2022, 10 pages.

Extended European Search Report dated Jul. 30, 2024, European Patent Application No. 24172047.3.

Non-final Office Action dated Mar. 16, 2026, U.S. Appl. No. 18/640,751, filed Apr. 19, 2024.

Response to Final Office Action dated Apr. 23, 2025, U.S. Appl. No. 17/880,928, filed Aug. 4, 2022.

Response to Office Action dated May 21, 2026, U.S. Appl. No. 18/640,751, filed Apr. 19, 2024.

Notice of Allowance dated May 19, 2025, U.S. Appl. No. 17/880,928, filed Aug. 4, 2022.

Final Office Action dated Mar. 18, 2025, U.S. Appl. No. 17/880,928, filed Aug. 4, 2022.

* cited by examiner

DEVICES, SYSTEMS AND METHODS THAT SELECT ELECTRODE VECTOR FOR CONDUCTIVE COMMUNICATION BETWEEN EXTERNAL DEVICE AND IMPLANTABLE MEDICAL DEVICES

PRIORITY CLAIM

The present application claims priority to U.S. Provisional Patent Application No. 63/570,205, filed Mar. 26, 2024, which is incorporated by reference as if set forth herein in its entirety.

FIELD OF TECHNOLOGY

Embodiments described herein generally relate to devices, systems and methods that enable an external device, such as an external programmer or a remote monitor, to perform conductive communication with one or more implantable medical devices, such as one or more leadless pacemakers, implanted within a patient using external electrodes that are in contact with the patient. Certain embodiments can also be used to enable communication between multiple implantable medical devices.

BACKGROUND

From time to time a non-implanted device needs to communicate with one or more implantable medical devices (IMDs), such as one or more leadless pacemakers (LPs), so that the non-implanted device can, for example, program the IMD(s), interrogate the IMD(s), and/or obtain notifications and/or other types of diagnostic information from the IMD(s). Such a non-implanted device, which can also be referred to as an external device or an external medical device (EMD), can be, e.g., an external programmer or a remote monitor, but is not limited thereto.

Communication between an external device and one or more IMDs (e.g., one or more LPs) may be facilitated by conductive communication via patient tissue, whereby two or more skin electrodes (that are part of or communicatively coupled to the external device) are attached to or otherwise placed in contact with skin of a patient within which (i.e., in whom) one or more IMDs is/are implanted, and the two or more skin or electrodes are used to transmit information to and/or receive information from the IMD(s) via conduction through body tissue of the patient. In other words, the two or more skin electrodes can be used by the external device to transmit conductive communication signals to and receive conductive communication signals from one or more individual IMDs. The conductive communication signals transmitted from an external device to an IMD, or vice versa, to achieve conductive communication can be referred to herein as conductive communication signals. The skin electrodes are examples of external electrodes, i.e., non-implanted electrodes. In certain embodiments, the skin electrodes are dry electrodes, which are electrodes that do not utilize an electrolyte gel at the interface between the electrode and skin of the patient. Conductive communication can also equivalently be referred to as conducted communication, or as tissue conductance communication (TCC).

One potential problem with using conductive communication signals to perform communication between an external device and one or more IMDs is that the orientation of the IMD(s) can cause fading that can adversely affect the conductive communication quality. Additionally, the locations of the skin electrodes, which in part define a communication vector for the external device, may affect the conductive communication quality between the external device and one or more IMDs. Additionally, noise that may vary over time can adversely affect conductive communication quality. These problems may be exacerbated when there is a need or desire for the external device to communicate with multiple (i.e., two or more) IMDs, such as multiple LPs.

SUMMARY

Certain embodiments of the present technology are directed to a method for use by an external device that is configured to communicate with an IMD implanted within a patient using conductive communication, wherein the external device includes or is communicatively coupled to at least three external electrodes that are in contact with the patient. The method includes, while the external device is not in an active conductive communication session with the IMD, selecting one of a plurality of different combinations of the at least three external electrodes as a test vector, and during an out-of-session (OOS) search window having a first duration using the test vector to search for an advertisement sequence transmitted by the IMD. The method further includes, if the advertisement sequence is not detected using the test vector during the OOS search window, selecting and using another one of the plurality of different combinations of the at least three external electrodes as the test vector to search for the advertisement sequence during another instance of the OOS search window having the first duration. In response to detecting the advertisement sequence from the IMD, the method includes establishing an active conductive communication session with the IMD using the test vector that was used to detect the advertisement sequence and determining a respective score for the test vector. Further, while the active conductive communication session is established with the IMD, the method includes using each of other ones of the plurality of different combinations of the at least three external electrodes as the test vector to perform conductive communication with the IMD during an accelerated search window having a second duration that is shorter than the first duration, and determining a respective score for each of the other ones of the plurality of different combinations of the at least three external electrodes used as the test vector during different instances of the accelerated search window. Additionally, the method includes selecting as a preferred vector, based on the scores, one of the plurality of different combinations of the at least three external electrodes used as the test vector, and performing further conductive communication with the IMD using the preferred vector.

In accordance with certain embodiments, the second duration of the accelerated search window is at least half of the first duration of the OOS search window.

In accordance with certain embodiments, when one of the plurality of different combinations of the at least three external electrodes is selected as the test vector, a first subset of the at least three external electrodes that is used by the external device to transmit conductive communication pulses to the IMD differs from a second subset of the at least three external electrodes that is used by the external device to receive conductive communication pulses from the IMD. Alternatively, when one of the plurality of different combinations of the at least three external electrodes is selected as the test vector, a same subset of the at least three external electrodes that is used by the external device to transmit conductive communication pulses to the IMD is also used by the external device to receive conductive communication pulses from the IMD.

In accordance with certain embodiments, the method includes, a next time the external device is not in an active conductive communication session with the IMD, and the external device attempts to communicate with the IMD, the external device using the preferred vector as an initial combination of the at least three external electrodes to use as the test vector to search for the advertisement sequence during another instance of the OOS search window.

In accordance with certain embodiments, the respective score, determined for each of the plurality of different combinations of the at least three external electrodes used as the test vector, comprises or is based at least in part on a bit score indicative of how well a certain type of bit (e.g., bits having a 1 bit value) is conductively communicated using the test vector.

In accordance with certain embodiments, the respective score, determined for each of the plurality of different combinations of the at least three external electrodes, is based at least in part on one or more of the following: how many valid frame headers were conductively communicated using the test vector; how many valid frame segments were conductively communicated using the test vector; or how many write acknowledgements were conductively communicated using the test vector.

In accordance with certain embodiments, a test vector must satisfy predetermined criteria to be eligible for being selected as the preferred vector.

Certain embodiments of the present technology are directed to a method for use by an external device that is configured to communicate with each of a plurality of IMDs implanted within a patient using conductive communication, wherein the external device includes or is communicatively coupled to at least three external electrodes that are in contact with the patient, and wherein each of the IMDs is configured to transmit a different one of a plurality of advertisement sequences. The method comprises while the external device is not in an active conductive communication session with the IMDs, selecting one of a plurality of different combinations of the at least three external electrodes as a test vector, and during an OOS search window having a first duration using the test vector to search for advertisement sequences transmitted by the IMDs. If the advertisement sequences transmitted by the IMDs are not detected using the test vector during the OOS search window, the method includes selecting and using another one of the plurality of different combinations of the at least three external electrodes as the test vector to search for the advertisement sequences during another instance of the OOS search window having the first duration. In response to detecting the advertisement sequences transmitted by the IMDs, the method includes establishing active conductive communication sessions with the IMDs using the test vector that was used to detect the advertisement sequences and determining for the test vector a separate respective score for each of the IMDs. While the active conductive communication session is established with the IMDs, the method includes using each of other ones of the plurality of different combinations of the at least three external electrodes as the test vector to perform conductive communication with the IMDs during an accelerated search window having a second duration that is shorter than the first duration, and determining for each of the other ones of the plurality of different combinations of the at least three external electrodes used as the test vector during different instances of the accelerated search window a separate respective score for each of the IMDs. The method further includes selecting as a preferred vector, based on the scores, one of the plurality of different combinations of the at least three external electrodes used as the test vector, and performing further conductive communication with the IMDs using the preferred vector.

Certain embodiments of the present technology are directed to an external device that includes at least three external electrodes configured to be placed in contact with skin of the patient within which the IMD is implanted, a conductive communication receiver, a conductive communication transmitter, a plurality of switches, and a controller communicatively coupled to the conductive communication receiver, the conductive communication transmitter, and the switches.

In certain embodiments, where the external device is configured to communicate with an IMD that is implanted in a patient, the controller is configured to control the switches to select one of a plurality of different combinations of the at least three external electrodes as a test vector while the external device is not in an active conductive communication session with the IMD, and use the test vector to search for an advertisement sequence transmitted by the IMD during an OOS search window having a first duration. If the advertisement sequence is not detected using the test vector during the OOS search window, the controller is configured to control the switches to select and use another one of the plurality of different combinations of the at least three external electrodes as the test vector to search for the advertisement sequence during another instance of the OOS search window having the first duration. In response the advertisement sequence being detected from the IMD, the controller is configured to establish an active conductive communication session with the IMD using the test vector that was used to detect the advertisement sequence and determine a respective score for the test vector. While the active conductive communication session is established with the IMD, the controller is configured to control the switches to use each of other ones of the plurality of the different combinations of the at least three external electrodes as the test vector to perform conductive communication with the IMD during an accelerated search window having a second duration that is shorter than the first duration, and determine a respective score for each of the other ones of the plurality of different combinations of the at least three external electrodes used as the test vector during different instances of the accelerated search window. The controller is further configured to select as a preferred vector, based on the scores, one of the plurality of different combinations of the at least three external electrodes used as the test vector, and perform further conductive communication with the IMD using the preferred vector.

In certain embodiments, the external device is configured to communicate with a plurality of implantable medical devices IMDs implanted in a patient, wherein each of the IMDs is configured to transmit a different one of a plurality of advertisement sequences. In such embodiments, the controller is configured to control the switches to select one of a plurality of different combinations of the at least three external electrodes as a test vector while the external device is not in an active conductive communication session with the IMDs, and use the test vector to search for the advertisement sequences transmitted by the IMDs during the OOS search window having the first duration. If the advertisement sequences transmitted by the IMDs are not detected using the test vector during the OOS search window, the controller is configured to control the switches to select and use another one of the plurality of different combinations of the at least three external electrodes as the test vector to search for the advertisement sequences transmitted by the IMDs during another instance of the OOS search window having the first duration. In response the advertisement sequences being detected from the IMDs, the controller is configured to establish active conductive communication sessions with the IMDs using the test vector that was used to detect the advertisement sequences and determine for the test vector a separate respective score for each of the IMDs. While the active conductive communication sessions are established with the IMDs, the controller is configured to control the switches to use each of other ones of the plurality of different combinations of the at least three external electrodes as the test vector to perform conductive communication with the IMDs during an accelerated search window having a second duration that is shorter than the first duration, and determine for each of the other ones of the plurality of different combinations of the at least three external electrodes used as the test vector during different instances of the accelerated search window a separate respective score for each of the IMDs. The controller is further configured to select as a preferred vector, based on the scores, one of the plurality of different combinations of the at least three external electrodes used as the test vector, and perform further conductive communication with the IMDs using the preferred vector.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Embodiments of the present technology can be used to enable and/or improve conductive communication between an external device and one or more implantable medical devices (IMDs) in time, cost and/or energy efficient manners. For example, certain embodiments of the present technology relate to specifying an appropriate edge detection threshold for use when performing conductive communication. Certain embodiments relate to use of the edge detection threshold to produce edge detections and decode a received conductive communication signal. Other embodiments of the present technology relate to an external device's tiered search for an advertisement sequence transmitted by an IMD to enable the external device to detect the presence of the IMD and establish an active conductive telemetry session with the IMD. Still other embodiments relate to the use of at least three different cyclic redundancy check (CRC) codes within a same frame, which enables one or more segments of the frame that do not include an error (as determined based on its respective CRC) to be accepted, while one or more other segments of the frame that do include an error (as determined based on its respective CRC) are rejected. Individual ones of the aforementioned embodiments can be used on their own, or together with one or more other embodiments. Addition embodiments of the present technology are also disclosed herein. However, before providing addition details of the specific embodiments of the present technology, an example environment in which embodiments of the present technology can be useful will first be described with reference to FIGS. 1-3.

Figure 1:
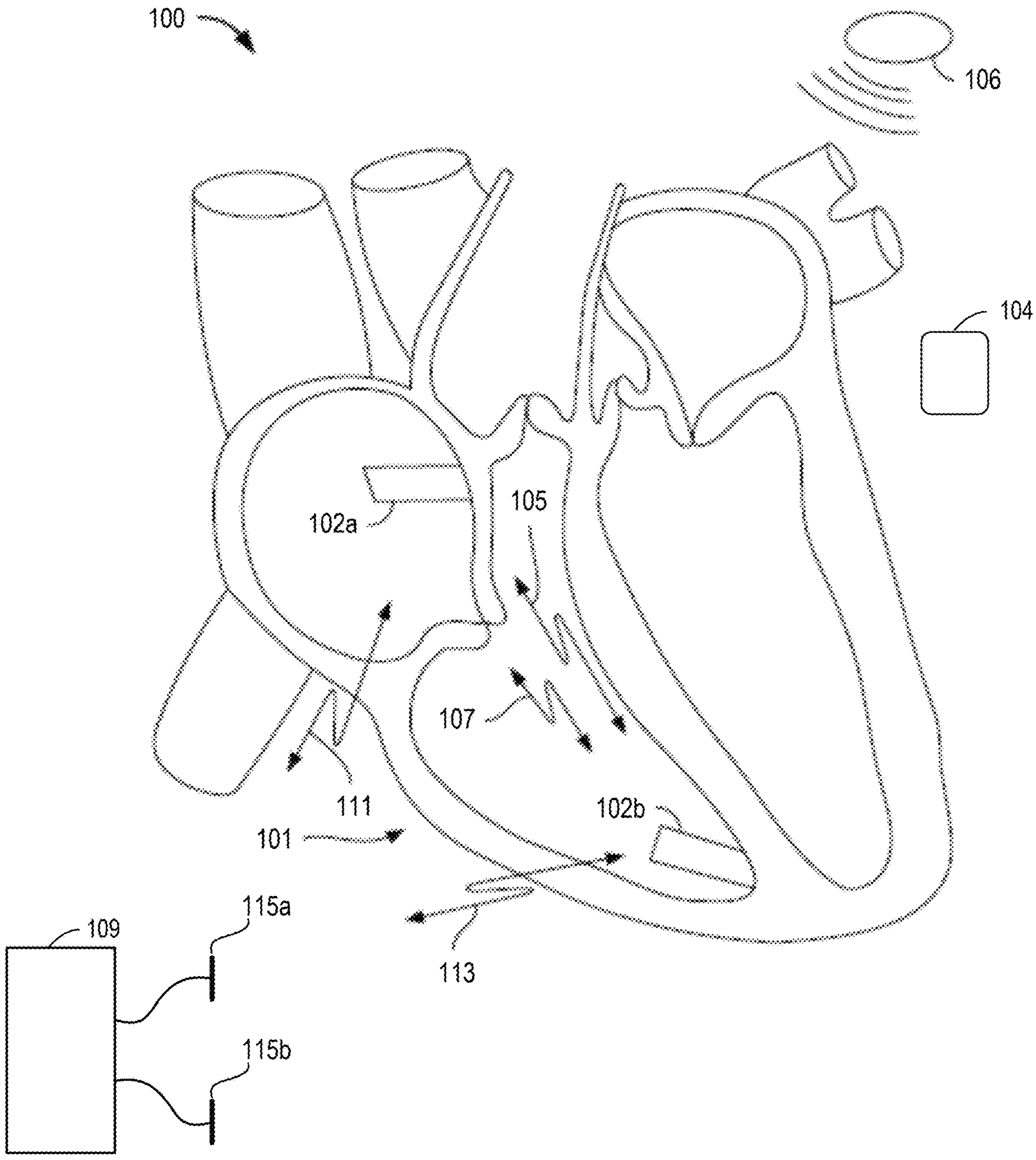
FIG. 1 illustrates a system that includes a plurality of IMDs that are implanted in a patent and an external device that can be used to program and/otherwise communicate with the IMDs.
Figure 2:
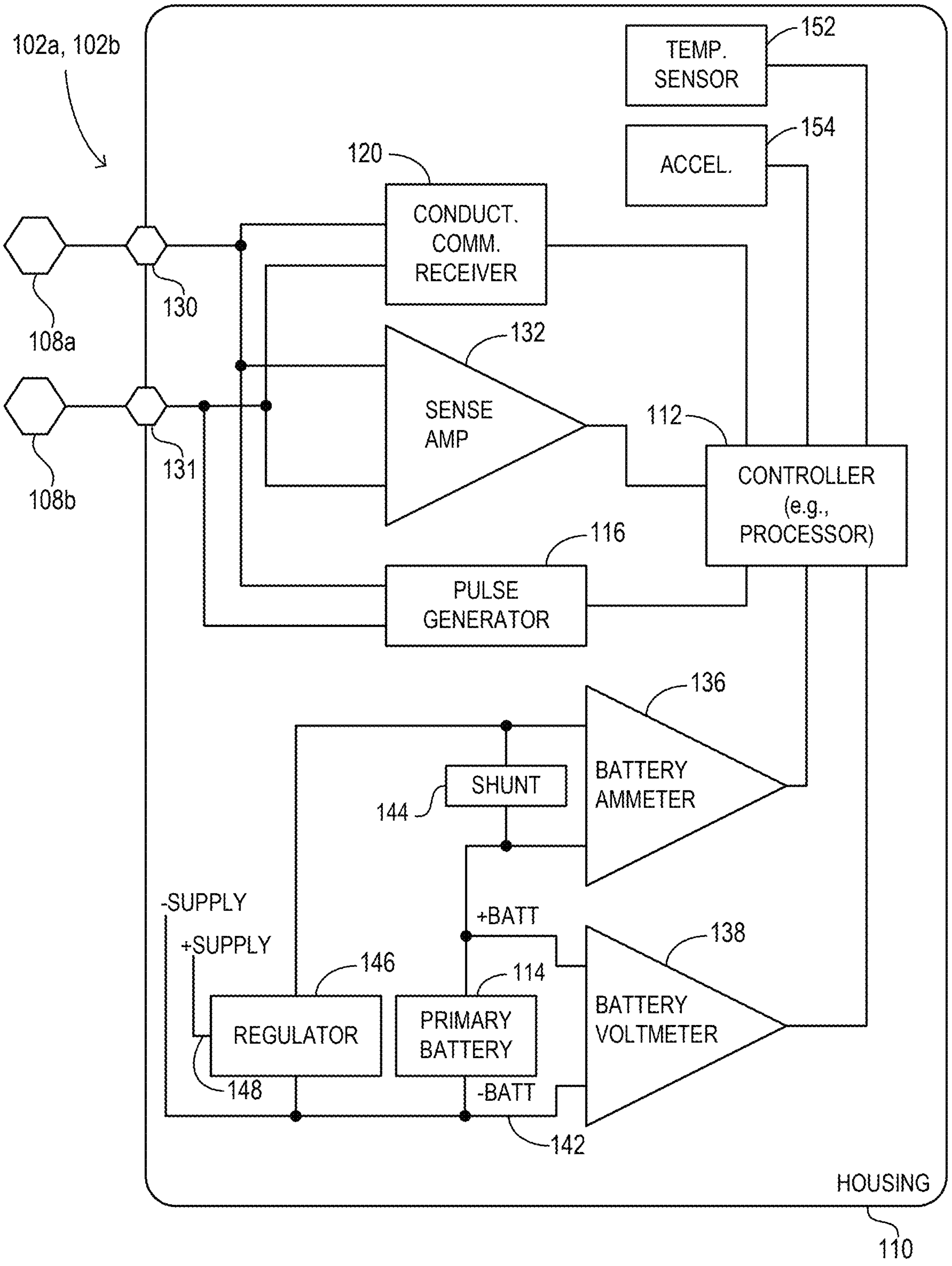
FIG. 2 is a high level block diagram of an example LP.
Figure 3:
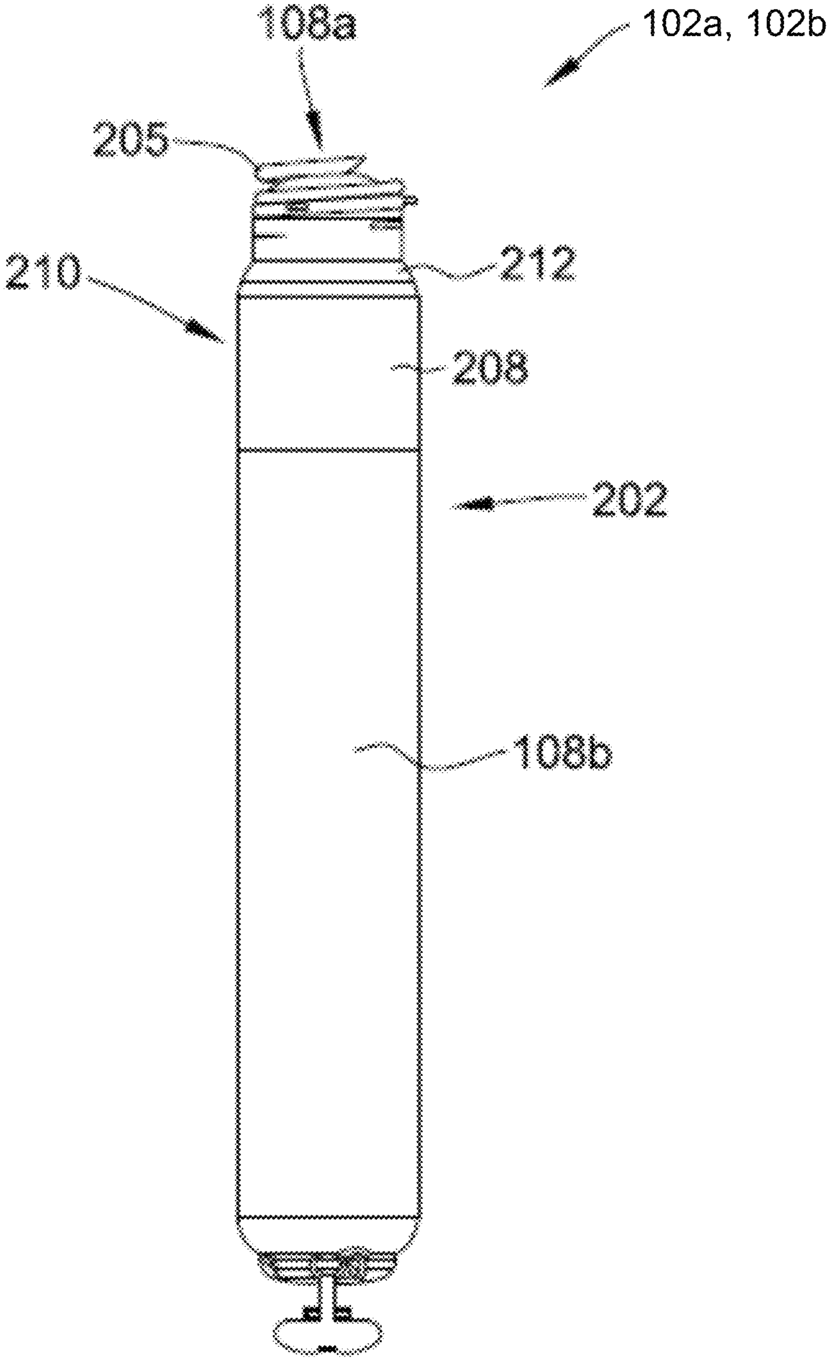
FIG. 3 illustrates an example form factor for an LP.

More specifically, FIGS. 1-3 will be used to describe an example cardiac pacing system, wherein pacing and sensing operations can be performed by multiple IMDs. Such systems may include one or more leadless pacemakers (LPs), an implantable cardioverter defibrillator (ICD), such as a non-vascular ICD (NV-ICD), an insertable cardiac monitor (ICM), and/or an external device. Where the system includes an ICD, the system is also capable of performing defibrillation. Where the only IMD is an ICM, the system may only be capable of performing monitoring without performing any therapy. The external device may also be referred to herein as an external medical device (EMD).

FIG. 1 illustrates a system 100 that is configured to be at least partially implanted in a heart 101. The system 100 includes LPs 102*a* and 102*b* located in different chambers of the heart 101. The LP 102*a* is located in a right atrium, while LP 102*b* is located in a right ventricle. The LPs 102*a* and 102*b* can communicate with one another to inform one another of various local physiologic activities, such as local intrinsic events, local paced events, and/or the like. The LPs 102*a* and 102*b* may be constructed in a similar manner, but operate differently based upon which chamber LP 102*a* or 102*b* is located. The LPs 102*a* and 102*b* may sometimes be referred to collectively herein as the LPs 102, or individually as an LP 102.

In certain embodiments, the LPs 102*a* and 102*b* communicate with one another, and/or with an ICM 104, and/or with an ICD 106, by conductive communication through the same electrodes that are used for sensing and/or delivery of pacing therapy. The LPs 102*a* and 102*b* also use conductive communication to communicate with a non-implanted device 109, having at least two electrodes 115*a* and 115*b* placed on or against the skin of a patient within which the LPs 102*a* and 102*b* are implanted. The non-implanted device 109, which can also be referred to as an external device 109 or an external medical device (EMD) 109, can be an external programmer that is capable of programming the LPs 102, the ICM 104, and/or the ICD 106. The external device 109 can alternatively be an external monitor, such as a bedside monitor, or a patient link monitor (PLM), that is incapable of programming the LPs 102, the ICM 104, and/or the ICD 106.

While not shown (and not preferred, since it would increase the size and power consumption of the LPs 102*a* and 102*b*), the LPs 102*a* and 102*b* can potentially include an antenna and/or telemetry coil that would enable them to communicate with one another, the ICD 106 and/or a non-implanted device using RF and/or inductive communication. While only two LPs 102 are shown in FIG. 1, it is possible that more than two LPs can be implanted in a patient. For example, to provide for bi-ventricular pacing and/or cardiac resynchronization therapy (CRT), in addition to having LPs implanted in or on the right atrial (RA) chamber and the right ventricular (RV) chamber, a further LP can be implanted in or on the left ventricular (LV) chamber. It is also possible that a single LP be implanted within a patient, e.g., in or on the RV chamber, the RA chamber, or the LV chamber, but not limited thereto. It would also be possible for more than one LP to be implanted in or on a same cardiac chamber.

In some embodiments, one or more of the LPs 102*a*, 102*b* can be co-implanted with the ICM 104 and/or the ICD 106. In such embodiments, the ICM 104 and/or the ICD 106 are examples of other types of IMDs that may need to communicate with an external device, such as an external programmer, from time to time. The ICM 104 and/or the ICD 106 may utilize conductive communication to communicate with the LPs 102, as well as to communicate with an external device. It may alternatively or additionally be possible for the ICM 104 and/or the ICD 106 to utilize radio frequency (RF) communication and/or inductive communication to communicate with an external device, depending upon the specific implementation, and depending upon the capabilities of the external device.

Each LP 102 uses two or more electrodes located within, on, or within a few centimeters of the housing of the pacemaker, for pacing and sensing at the cardiac chamber, for bidirectional conductive communication with one another, with the external device 109, the ICD 106, and/or the ICM 104. Such an ICM 104 can be intended for subcutaneous implantation at a site near the heart 101. The ICM 104 can include, for example, a pair of spaced-apart sense electrodes positioned with respect to a housing, wherein the sense electrodes provide for detection of far-field EGM signals, and can also be used for conductive communication with one or more other implanted devices, such as the LP(s) 102*a* and/or 102*b* and/or the ICD 106, and/or can be used for conductive communication with the external device 109. Such an ICM can also include an antenna that is configured to wirelessly communicate with an external device using one or more wireless communication protocols (e.g., Bluetooth, Bluetooth low energy, Wi-Fi, etc.). The housing of the ICM 104 can include various other components such as: sense electronics for receiving signals from the electrodes, a microprocessor for processing the signals in accordance with algorithms, a loop memory for temporary storage of cardiac activity (CA) data, a device memory for long-term storage of CA data upon certain triggering events, sensors for detecting patient activity and a battery for powering components.

Each LP 102 and/or other type of IMD can transmit an advertisement sequence using at least two electrodes of the IMD (e.g., LP) from time to time so that an external device (e.g., an external programmer, or a remote monitor) that has or is communicatively coupled to external electrodes that are in contact with the patient (within which the LP(s) and/or other IMD(s) is/are implanted) can detect the presence of the IMD(s) and optionally establish an active conductive telemetry session (which can also be referred to as an active conductive communication session) with one or more IMD(s). For a more specific example, an LP (or other type of IMD) can transmit an advertisement sequence once every specified number of cardiac cycles (e.g., once every eight cardiac cycles), or once every specified period of time (e.g., once every 5 seconds), but is not limited thereto. As will be described below with reference to FIG. 8A, in accordance with certain embodiments of the present technology, each advertisement sequence includes a preamble followed by a device address, wherein the preamble is a known sequence of bits (e.g., a known byte) regardless of which IMD transmits the advertisement sequence, and the device address is one of a plurality (e.g., four) possible device addresses that corresponds to the type of IMD and/or the location of the IMD that transmits the advertisement sequence. In order to reduce the probability that advertisement sequences transmitted by different IMDs will collide with one another (i.e., be transmitted at overlapping times by different IMDs, making them difficult or impossible for the external device to receive), different IMDs will transmit their respective advertisement sequences at a different rate or periodicity. For example, a first IMD may transmit its advertisement sequence (which includes the preamble and a first device address) once every seven cardiac cycles, a second IMD may transmit its advertisement sequence (which includes the preamble and a second device address) once every eight cardiac cycles, a third IMD may transmit its advertisement sequence (which includes the preamble and a third device address) once every nine cardiac cycles, and so on. For another example, a first IMD may transmit its advertisement sequence (which includes the preamble and a first device address) once every seven seconds, a second IMD may transmit its advertisement sequence (which includes the preamble and a second device address) once every eight seconds, a third IMD may transmit its advertisement sequence (which includes the preamble and a third device address) once every nine seconds, and so on.

In accordance with certain embodiments, the advertisement sequence is a predetermined sequence that indicates to an external device (e.g., an external programmer, or a remote monitor) that an LP (or other type of IMD) is implanted within a patient. The advertisement sequence can also be referred to as a sniff sequence, or more succinctly as a sniff. In other words, the terms advertisement sequence, sniff sequence, and sniff, are used interchangeably herein.

In certain embodiments, each sniff sequence (aka advertisement sequence) that is transmitted by an LP (or another type of IMD) is transmitted during a cardiac refractory period that follows an intrinsic or pace cardiac activation (aka depolarization). Where an LP is implanted in or on a ventricular cardiac chamber, the refractory period associated with that LP follows an intrinsic or paced ventricular depolarization. Where an LP is implanted in or on an atrial cardiac chamber, the refractory period associated with that LP follows an intrinsic or paced atrial depolarization. The length of the refractory periods can be programmed and can be, e.g., in the range of 100 to 500 msec long. It is also possible that a refractory period is rate dependent and/or is dependent on one other factors that may change over time.

In certain embodiments, described below, each sniff sequence (aka advertisement sequence) that is transmitted by an LP 102 (or another type of IMD) includes a specified preamble and an address of the LP 102 (or other type of IMD).

In certain embodiments, the external device 109 can use the sniff sequence to initiate an active conductive telemetry session (aka an active conductive communication session) with an LP 102 (or another type of IMD), as will be described in additional detail below.

In certain embodiments, the external device 109 can use the sniff sequence to identify which one of a plurality of possible conductive communication vectors is a preferred conductive communication vector for communicating with the LP 102 (or other type of IMD) that transmitted the sniff sequence. For example, where the external device 109 has or is communicatively coupled to three external electrodes, i.e., first, second, and third external electrodes (e.g., 115*a*, 115*b*, 115*c* in FIGS. 6 and 7), the external device 109 can test and select among first, second, and third subsets of the external electrodes, wherein the first subset includes the first and second external electrodes (e.g., 115*a* and 115*b* in FIGS. 6 and 7), the second subset includes the first and third external electrodes (e.g., 115*a* and 115*c* in FIGS. 6 and 7), and the third subset includes the second and third external electrodes (e.g., 115*b* and 115*c* and FIGS. 6 and 7). Each of the aforementioned subsets of external electrodes can also be thought of as defining a conductive communication vector.

Referring to FIG. 2, a block diagram shows an example embodiment for portions of the electronics within the LPs 102*a*, 102*b* configured to provide conductive communication through the same electrodes that are used for cardiac pacing and/or sensing. Each of the LPs 102*a*, 102*b* includes at least two leadless electrodes configured for delivering cardiac pacing pulses, sensing evoked and/or natural cardiac electrical signals, and uni-directional and/or bi-directional communication. In FIG. 2 (and FIG. 3) the two electrodes shown therein are labeled 108*a* and 108*b*. Such electrodes can be referred to collectively as the electrodes 108, or individually as an electrode 108. An LP 102, or other type of IMD, can include more than two electrodes, depending upon implementation.

In FIG. 2, each of the LPs 102*a*, 102*b* is shown as including a conductive communication receiver 120 that is coupled to the electrodes 108 and configured to receive conductive communication signals from the other LP 102, the ICM 104 and/or the ICD 106, but not limited thereto. The conductive communication receiver 120 and the electrodes 108 can also be used to receive conductive communication signals from the external device 109. Although one receiver 120 is depicted in FIG. 2, in other embodiments, each LP 102*a*, 102*b* may also include one or more additional receivers. As will be described in additional detail below, the pulse generator 116 can function as a transmitter that transmits conductive communication signals using the electrodes 108, under the control of the controller 112. In certain embodiments, the LPs 102*a*, 102*b* may communicate over more than just first and second communication channels 105 and 107. In certain embodiments, the LPs 102*a*, 102*b* may communicate over one common communication channel 105. More specifically, the LPs 102*a* and 102*b* can communicate conductively over a common physical channel via the same electrodes 108 that are also used to deliver pacing pulses. Usage of the electrodes 108 for conductive communication enables the one or more LPs 102*a*, 102*b* to perform antenna-less and inductive coil-less communication. Where multiple implantable devices (such as the LPs 102*a* and 102*b*) communicate with one another using conductive communication, such conductive communication can be referred to as implant-to-implant (i2i) conductive communication, or more succinctly, as i2i conductive communication.

Optionally, an LP (or other IMD) that receives any conductive communication signal from another LP (or other IMD) or from a non-implanted device (aka an external device) may transmit a receive acknowledgement indicating that the receiving LP (or other IMD, or external device) received the conductive communication signal. In certain embodiments, where an IMD expects to receive a conductive communication signal within a window, and fails to receive the conductive communication signal within the window, the IMD may transmit a failure-to-receive acknowledgement indicating that the receiving IMD failed to receive the conductive communication signal. A failure-to-receive acknowledgement can also be referred to herein as a negative acknowledgement (NACK). Other variations are also possible and within the scope of the embodiments described herein. Each conductive communication signal can include one or more sequences of conductive communication pulses. In accordance with certain embodiments, conductive communication pulses are delivered during cardiac refractory periods that are identified or detected by the LP(s) and/or other IMD(s) and/or or from a non-implanted device (aka an external device). In accordance with certain embodiments, conductive communication pulses are subthreshold, i.e., they are below the capture threshold for the patient.

The LPs 102*a*, 102*b* can exchange event messages within i2i conductive communication signals to enable synchronized therapy and additional supportive features (e.g., measurements, etc.). To maintain synchronous therapy, each of the LPs 102*a*, 102*b* is made aware (through the event messages) when an event occurs in the chamber containing the other LP 102*a*, 102*b*. As will be described in additional detail below, with reference to FIG. 5, instead of the LP 102*a* being located within RA chamber, the LP 102*a* can be located on an exterior surface of the RA chamber. Additionally, or alternatively, instead of the LP 102*b* being located within RV chamber, the LP 102*b* can be located on an exterior surface of the RV chamber.

For synchronous event signaling, LPs 102*a* and 102*b* may maintain synchronization and regularly communicate at a specific interval. Synchronous event signaling allows the transmitter and receiver in each LP 102*a*, 102*b* to use limited (or minimal) power as each LP 102*a*, 102*b* is only powered for a small fraction of the time in connection with transmission and reception. For example, LP 102*a*, 102*b* may transmit/receive (Tx/Rx) communication messages in time slots having duration of 10-20 μs, where the Tx/Rx time slots occur periodically (e.g., every 10-20 ms). Such time slots can also be referred to as windows.

Still referring to FIG. 2, each LP 102*a*, 102*b* is shown as including a controller 112 and a pulse generator 116. The controller 112 can include, e.g., a microprocessor (or equivalent control circuitry), logic and timing circuitry, state machine circuitry, and I/O circuitry, but is not limited thereto. The controller 112 can include random access memory (RAM) and/or read only memory (ROM), and/or can be coupled to memory 118. More generally, the memory 118, which can include RAM and/or ROM, can be within the controller 112 and/or external to and coupled to the controller 112. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies.

The controller 112 and the pulse generator 116 may be configured to transmit event messages, via the electrodes 108, in a manner that does not inadvertently capture the heart in the chamber where LP 102*a*, 102*b* is located, such as when the associated chamber is not in a refractory state. In addition, an LP 102*a*, 102*b* that receives an event message may enter an "event refractory" state (or event blanking state) following receipt of the event message. The event refractory/blanking state may be set to extend for a determined period of time after receipt of an event message in order to avoid the receiving LP 102 from inadvertently sensing another signal as an event message that might otherwise cause retriggering. For example, the receiving LP 102 may detect a measurement pulse from another LP 102 or the external device 109. While only one pulse generator 116 is shown in FIG. 2, it is possible that the LP 102 includes two pulse generators 116, one of which is used to generate pacing pulses and another one of which is used to generate conductive communication pulses. Alternatively, the same pulse generator 116 can be used to generate both pacing pulses and conductive communication pulses.

In accordance with certain embodiments herein, the external device 109 may communicate over an external device-to-LP channel, with LPs 102*a*, 102*b* utilizing the same communication scheme. The external device 109 may listen to the event message transmitted between LPs 102*a*, 102*b*, wherein the event message is a type of i2i messaging sequence, and the external device can synchronize external device to implant communication such that the external device 109 does not transmit communication signals 113 until after an i2i messaging sequence is completed.

In some embodiments, an individual LP 102 can comprise a hermetic housing 110 configured for placement on or attachment to the inside or outside of a cardiac chamber and at least two leadless electrodes 108 proximal to the housing 110 and configured for conductive communication with at least one other device within or outside the body. Depending upon the specific implementation, and/or the other device with which an LP is communicating, the conductive communication may be unidirectional or bidirectional.

FIG. 2 shows functional elements of the LP 102 substantially enclosed in a hermetic housing 110. The LP 102 has at least two electrodes 108 located within, on, or near the housing 110, for delivering pacing pulses to and sensing electrical activity from the muscle of the cardiac chamber, and for conductive communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receiver 120 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example an optional battery current monitor 136 and an optional battery voltage monitor 138, and can contain circuits for controlling operations in a predetermined manner.

The electrodes 108 can be configured to communicate bidirectionally among the multiple leadless cardiac pacemakers, the implanted ICD 106 and/or the implanted ICM 104 to coordinate pacing pulse delivery and optionally other therapeutic or diagnostic features using messages that identify an event at an individual pacemaker originating the message and a pacemaker receiving the message react as directed by the message depending on the origin of the message. An LP 102*a*, 102*b* that receives the event message reacts as directed by the event message depending on the message origin or location. In some embodiments or conditions, the two or more leadless electrodes 108 can be configured to communicate bidirectionally among the one or more LPs, the ICD 106, and/or the ICM 104 and transmit data including designated codes for events detected or created by an individual pacemaker. Individual pacemakers can be configured to issue a unique code corresponding to an event type and a location of the sending pacemaker. The electrodes 108 can also be used to transmit and/or receive conductive communication signals to/from the external device 109.

Also shown in FIG. 2, the primary battery 114 has positive terminal 140 and negative terminal 142. Current from the positive terminal 140 of primary battery 114 flows through an optional shunt 144 to an optional regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114. The LP is also shown as including a temperature sensor 152 and an accelerometer 154, but may include just one of those, but not the other, or neither.

In various embodiments, each LP 102*a*, 102*b* can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102 can access signals on the electrodes 108 and can examine output pulse amplitude, duration, etc. from another LP for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

FIG. 3 shows an example form factor of an LP 102*a*, 102*b*. The LP can include a hermetic housing 202 (110) with electrodes 108*a* and 108*b* disposed thereon. As shown, electrode 108*a* can be separated from but surrounded partially by a fixation mechanism 205, and the electrode 108*b* can be disposed on the housing 202. The fixation mechanism 205 can be a fixation helix, a plurality of hooks, barbs, or other attaching features configured to attach the pacemaker to tissue, such as heart tissue. The electrodes 108*a* and 108*b* are examples of the electrodes 108 shown in and discussed above with reference to FIG. 2. The housing can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example. The housing can comprise a conductive, biocompatible, inert, and anodically safe material such as titanium, 316L stainless steel, or other similar materials. The housing 202 can further comprise an insulator disposed on the conductive material to separate electrodes 108*a* and 108*b*. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108*a* and 108*b*. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate electrodes 108*a* and 108*b*. The header assembly 212 can be made from PEEK, tecothane or another biocompatible plastic, and can contain a ceramic to metal feedthrough, a glass to metal feedthrough, or other appropriate feedthrough insulator as known in the art. The term metal, as used herein, also encompasses alloys that are electrically conductive. The electrodes 108*a* and 108*b* can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108*a* can be a pace/sense electrode and electrode 108*b* can be a return electrode. The electrode 108*b* can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108*a* in FIG. 2) into contact with stimulable tissue. Electrode 108*b* can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Figure 4:
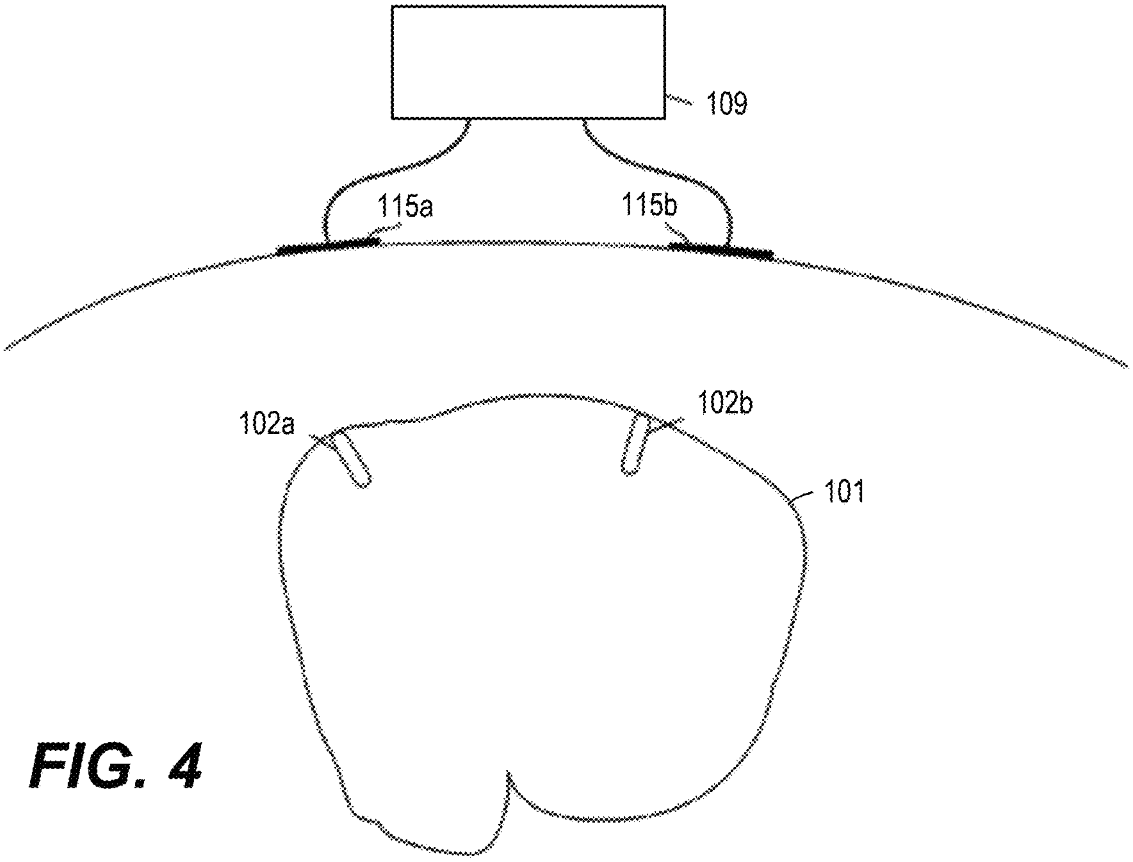
FIG. 4 depicts a sample configuration involving an external device and two endocardially implanted LPs.
Figure 5:
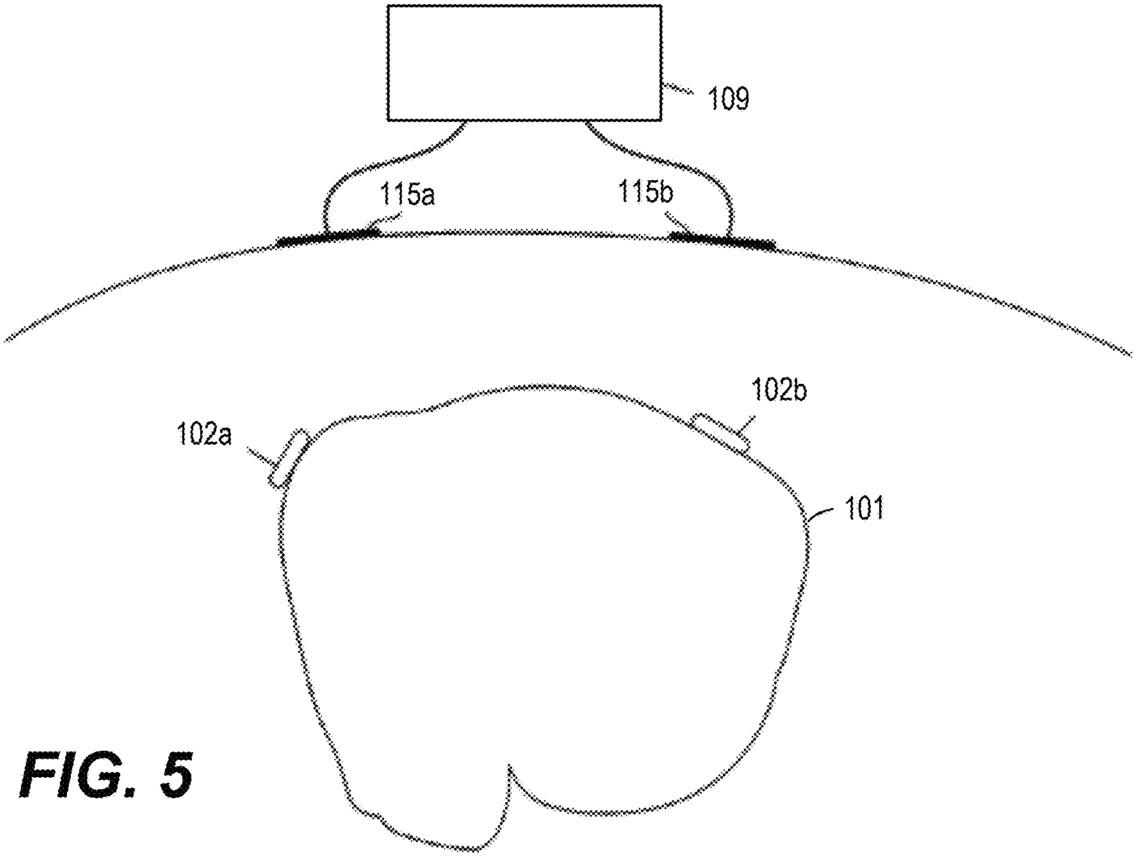
FIG. 5 depicts a sample configuration involving an external device and two LPs implanted epicardially (on the external heart surface).

FIGS. 4 and 5 are schematic pictorial views depicting how an external device 109 coupled to two electrodes 115*a*, 115*b* can communicate with the LP 102*a* and/or the LP 102*b* via conductive communication, which is also referred to interchangeably herein as conducted communication. Such communication may take place via bidirectional communication pathways comprising a receiving pathway that decodes information encoded on pulses generated by one or more of the LPs 102*a* or 102*b* and conductive through body tissue to the external device 109. According to the illustrative arrangement, the bidirectional communication pathways can be configured for communication with multiple LPs 102*a* and 102*b* via two or more electrodes and conduction through body tissue. While the external device 109 is shown as being coupled to two electrodes 115*a*, 115*b* in FIGS. 4 and 5 (and in FIG. 1), the external device 109 can also be coupled to one or more additional external electrode (e.g., 115*c* in FIGS. 6 and 7).

The external device 109 is connected by a communication transmission channel and has transmitting and receiving functional elements for a bidirectional exchange of information with one or more IMDs, such as LP 102*a* and/or LP 102*b*. The communication channel includes two (or more) external electrodes 115*a* and 115*b* which can be affixed or secured to the surface of the skin. From the point of the skin, the communication transmission channel is wireless, includes the ion medium of the intra- and extra-cellular body liquids, and enables electrolytic-galvanic coupling between the external electrodes, which can also be referred to as surface electrodes, and the LPs, or more generally, IMDs. The bidirectional communication pathways can further comprise a transmitting pathway that passes information from the external device 109 to one or more of the LPs 102*a* and/or 102*b* by direct conduction through the body tissue by modulation that avoids skeletal muscle stimulation using modulated signals at a frequency in a range from approximately 10 KHz to 100 kHz, or at higher frequencies.

Information transmitted from the external device 109 to an implanted LP 102 can be conveyed by modulated signals. The signals are passed through the communication transmission channel by direct conduction. A modulated signal in the frequency range has a sufficiently high frequency to avoid any depolarization within the living body which would lead to activation of the skeletal muscles and discomfort to the patient. The frequency is also low enough to avoid causing problems with radiation, crosstalk, and excessive attenuation by body tissue. Thus, information may be communicated at any time, without regard to the heart cycle or other bodily processes. Nevertheless, to minimize the probability that a conductive communication signal may cause capture of cardiac tissue, conductive communications signals can be transmitted during refractory periods in accordance with certain embodiments of the present technology. It is also noted that the use of other frequency ranges is also possible and within the scope of the embodiments described herein.

FIG. 4 depicts an example configuration involving the external device 109 and two endocardially implanted LPs 102*a* and 102*b*. The external device 109 is physically connected to the skin surface via two external electrodes 115*a* and 115*b* (also referred to as surface electrodes or skin electrodes), which can serve three functions. The external electrodes 115*a* and 115*b* can be referred to individually as an external electrode 115 (or a surface electrode 115 or skin electrode 115), or collectively as external electrodes 115 (or surface electrodes 115 or skin electrodes 115). First, the electrodes 115 can be used transmit encoded information from the external device 109 to the LPs 102 or other IMD(s) using a modulated signal. Second, the external electrodes 115 can be used to receive encoded information from individual LPs 102 or other IMD(s). Third, the external electrodes 115 can receive or sense a surface electrocardiogram (ECG) for display, recording and/or analysis by the external device 109. While only two external electrodes 115 are shown in FIG. 4, it is also possible that more than two (e.g., three or more) external electrodes 115 can be placed in contact with a patient, to enable various different communication vectors to be selected among, as will be explained in further detail below, e.g., with reference to FIGS. 6 and 7.

In FIG. 4, the LPs 102 are implanted within the heart 101 endocardially. Alternatively, as shown in FIG. 5, the LPs 102 can be implanted by affixing to the exterior surface of the heart 101. The external electrodes 115 and the external device 109 function similarly in arrangements shown in FIGS. 4 and 5 whether the LPs 102 are implanted endocardially or epicardially (on the external heart surface). No restriction is imposed that the LPs are all implanted inside or all implanted outside the heart. One or more LP may be implanted endocardially along with one or more others implanted on the outer surface of the heart.

Figure 6:
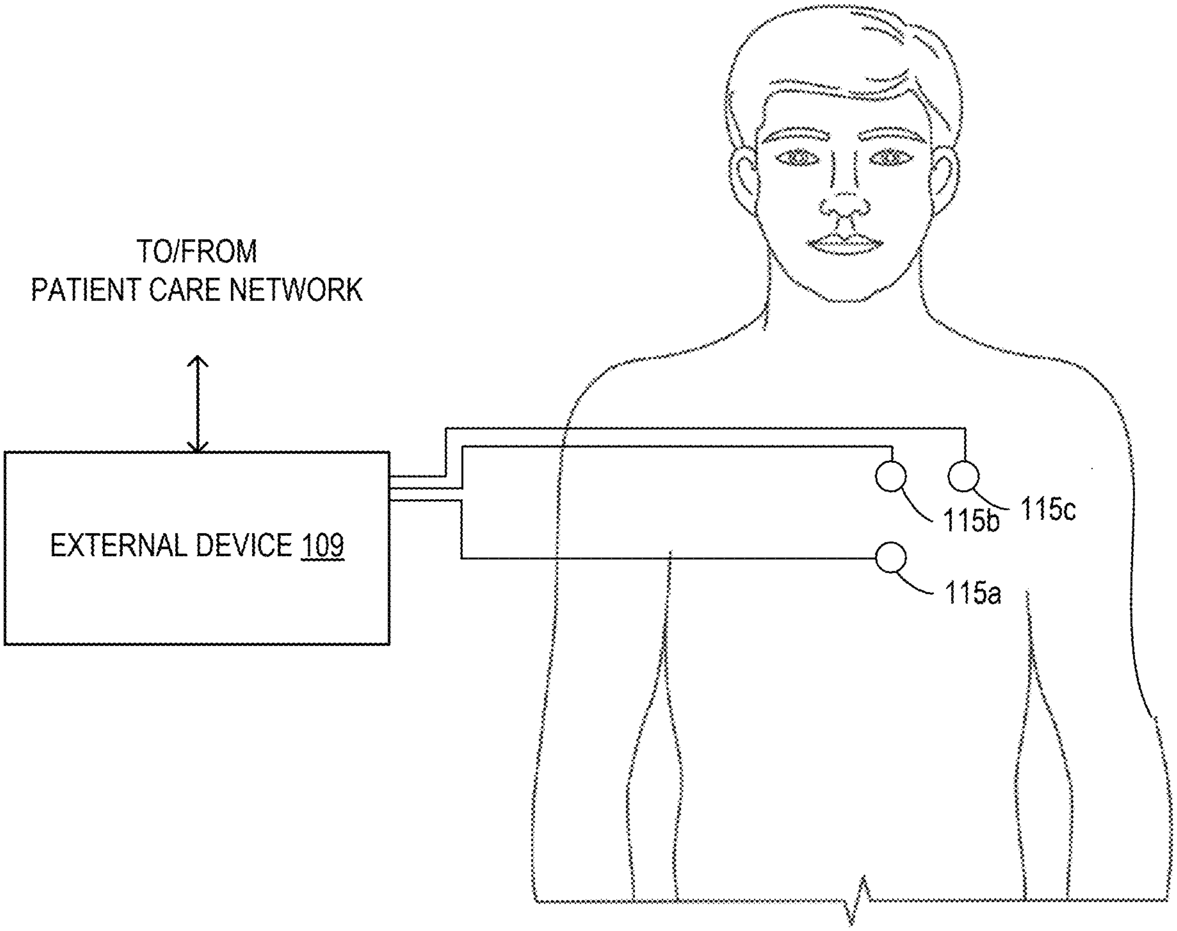
FIG. 6 depicts an example of an external device communicatively coupled to three electrodes that are in contact with the chest of a patient.

Referring to FIG. 6, an external device 109 is shown as being communicatively coupled to three external electrodes 115*a*, 115*b*, and 115*c*, which can be referred to collectively as the external electrodes 115, or individually as an external electrode 115. In FIG. 6 the external electrodes 115 are shown as being in contact with the chest of a patient, however, that need not be the case. Alternatively, one or more external electrodes 115 can be in contact with the back of the patient, and/or with limbs or digits of the patient, but are not limited thereto. The external electrodes 115 can be physically separated from one another to thereby enable each of the electrodes to be independently placed in contact with the patient's skin at any desired location. Alternatively, the external electrodes 115, while electrically isolated from one another, can be physically attached to a same patch or substrate, e.g., a triangular or Y-shaped patch, or the like, that can be configured to be placed on a patient's chest or back, but not limited thereto. The external device 109 can alternatively include (or be communicatively coupled to) one or more external electrodes 115 configured to be grasped by a patient's left hand, one or more external electrodes 115 configured to be grasped by the patient's right hand, and one or more electrodes 115 configured to be placed against one of the patient's thighs or ankles. Other variations are also possible and within the scope of the embodiments described herein. The external device 109 can optionally be communicatively coupled to a remote patient care network, e.g., via one or more wired and/or wireless communication network(s). Example details of the external device 109 are described below with reference to FIG. 7.

Figure 7:
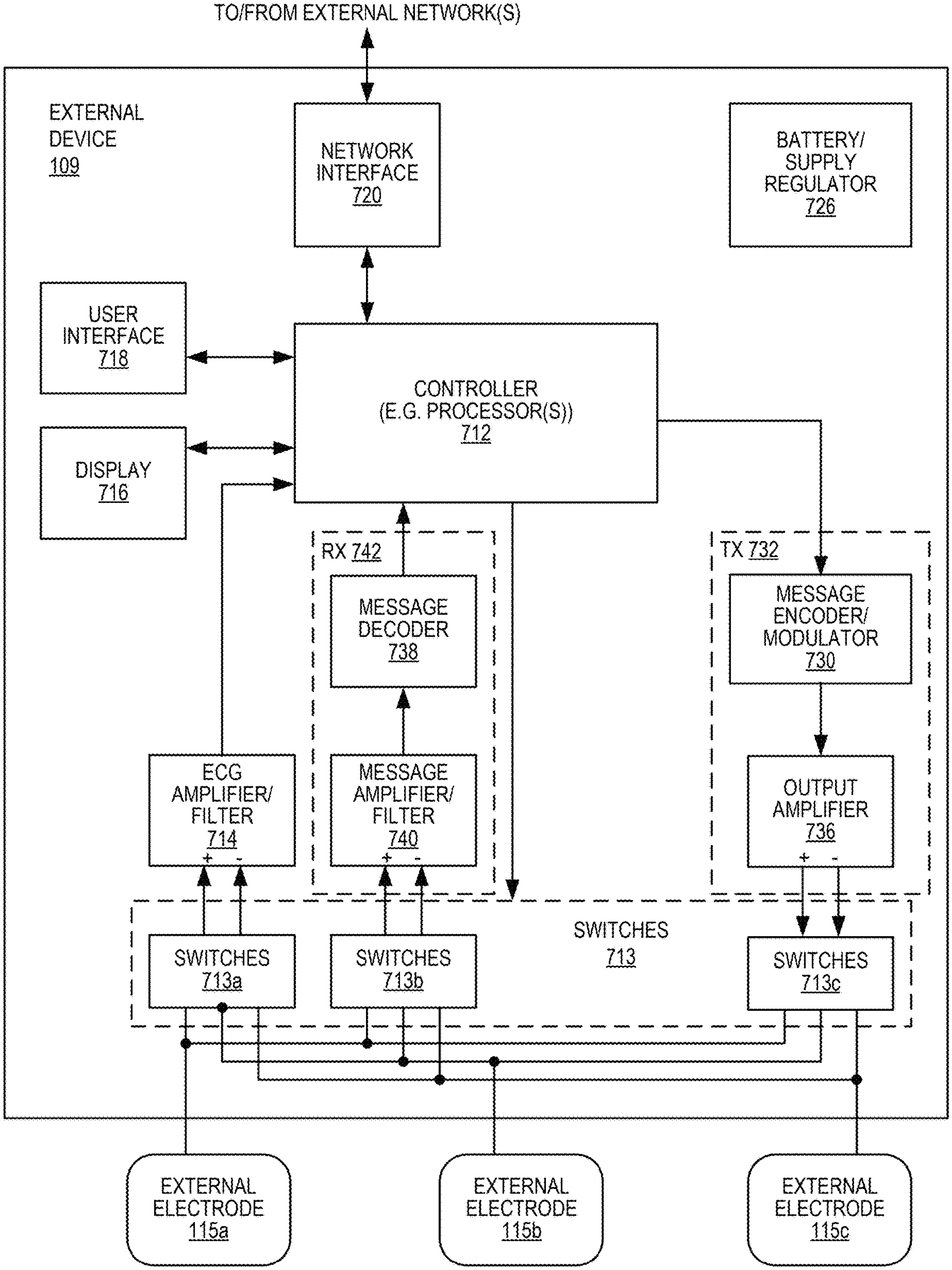
FIG. 7 is a high level block diagram illustrating example details of an external device that is configured to communicate with one or more IMDs implanted within a patient using conductive communication, wherein the external device includes or is communicatively coupled to at least three external electrodes that are in contact with the patient.

Referring to FIG. 7, shown therein is an example block diagram of the external device 109 (e.g., an external programmer, a remote monitor, or a patient link monitor), which is configured to communicate with one or more IMDs (e.g., LPs 102) implanted within a patient using conductive communication, wherein the external device 109 includes or is communicatively coupled to at least three external electrodes 115 that are in contact with the patient.

Where the external device 109 is an external programmer, the external device is capable of programming one or more IMDs, such as one or more LPs 102, an ICM 104 and/or an ICD 106. The external device 109 can also be used to obtain diagnostic information from one or more IMDs. Where the external device 109 is a remote monitor, it may not be capable of programming any IMDs. The external device 109 is shown as including a controller 712, a display 716, a user-interface 718, a network interface 720, and a battery/supply regulator 726. The battery and/or supply regulator 726 provides one or more constant voltages to the various components of the external device 109 during normal operation. The external device 109 is also shown as including an ECG amplifier and/or filter 714, a conductive communication receiver (RX) 742, and a conductive communication transmitter (TX) 732. The receiver 742, in this example embodiment, is shown as including a message amplifier and/or filter 740, and a message decoder 738, and is configured to receive conductive communication signals from one or more LPs (e.g., 102*a* and/or 102*b*). It is also possible that the message decoder 738 is implemented by or within the controller 712. The controller 712, which is used to control the operation of the external device 702, can include, e.g., one or more processors (or equivalent control circuitry), logic and timing circuitry, state machine circuitry, and/or I/O circuitry, but is not limited thereto. The controller 712 can include random access memory (RAM) and/or read only memory (ROM), and/or can be coupled to memory 722. More generally, the memory 722, which can include RAM and/or ROM, can be within the controller 712 and/or external to and coupled to the controller 712. The controller 712 can also include a clock circuit, or a separate clock circuit (not shown) can provide a clock signal to the controller 712.

In the embodiment shown in FIG. 7, the external device 109 is shown as being connected to three external electrodes 115*a*, 115*b*, and 115*c*, which can be referred to collectively as the electrodes 115, or individually as an electrode 115. The electrodes 115 are shown as being connected to switches 713, which are shown as including first, second, and third sets of switches 713*a*, 713*b*, and 713*c*. The external electrodes 115 can be located on a housing of the external device 109, or can be separate from (i.e. remote from) such a housing. Where the electrodes 115 are separate from a housing of the external device 109, each of the electrodes 115 can be attached to a separate respective wire, or the electrodes 115 can be attached to a further housing that is communicatively coupled to the external device 109 via one or more wires, or via a wireless connection, e.g., using Bluetooth or WiFi, but not limited thereto. Other variations are also possible and within the scope of the embodiments described herein. The external electrodes 115, as will be described in more detail below, can be used to transmit and receive conductive communication signals to/from one or more LPs, and/or one or more other types of IMDs, and optionally can also be used to sense an ECG.

The external electrodes 115 are intended to come into contact with the skin of a patient. For example, the external electrodes 115 can be skin electrodes that are configured to be attached to a patient's torso (e.g., chest and/or back) via an adhesive and/or gel. For another example, the external electrodes 115 can be configured to be touched by one or more digits on each hand of a patient, or to come into contact with a patient's wrist, a patient's limb, or a patient's chest, but are not limited thereto. A set of switches 713*a* is connected between the electrodes 115 and the ECG amplifier and/or filter 714, a set of switches 714*b* is connected between the electrodes 115 and the receiver 742, and a further set of switches 713*c* is connected between the electrodes 115 and the transmitter 732. The sets of switches 713*a*, 713*b*, 713*c* can be referred to collectively as sets of switches 713 or as switches 713. The various sets of switches 713 are controlled by the controller 712. In certain embodiments, the amplifiers and/or filters 714, 740, and 736 are each differential circuits that are intended to be connected to a pair of the electrodes 115 by the switches 713 under the control of the controller 712. For an example, the switches 713*b* can be controlled to connect any pair of the electrodes 115*a*, 115*b*, 115*c* to the message amplifier and/or filter 740 (which can also be referred to as the message amplifier/filter 740). For a more specific example, the switches 713*b* can connect the electrode 115*a* to a first input of the message amplifier/filter 740, and connect the electrode 115*b* to a second input of the message amplifier/filter 740, and not connect electrode 115*c* to any input of the message amplifier/filter 740. It is also possible that the switches can connect two electrodes 115 directly to one another. For an example, the switches 713*b* can connect the electrode 115*a* to a first input of the message amplifier/filter 740, and connect the electrodes 115*b* and 115*c* to one another and to a second input of the message amplifier/filter 740. Beneficially, connecting together two or more electrodes (e.g., 115*b* and 115*c*) to a same node (e.g., to the same input node of the message amplifier/filter 740) can effectively average or create a virtual vector which is between the two or more electrode locations, which enables sensing of a signal that is effectively an average of the signals detected at the two separate electrodes. This is an example of where a combination of the three electrodes 115*a*, 115*b*, and 115*c* includes all three of the electrodes, with the electrode 115*a* being separate from the other electrodes, and the electrodes 115*b* and 115*c* being electrically coupled to one another. The inclusion of three (or more) external electrodes 115 enables an ECG to be sensed at multiple vectors and/or enables selection from among the multiple vectors for conductive communication with one or more implanted LPs so that conductive communication quality can be improved or maximized.

As noted above, the conductive communication receiver 742, which is shown as including the message amplifier and/or filter 740, and the message decoder 738, is configured to receive conductive communication signals from one or more LPs (e.g., 102*a* and/or 102*b*). The message amplifier and/or filter 740 is configured to amplify and/or filter conductive communication signals received from an LP (e.g., 102*a* and/or 102*b*). The amplifier portion can be used to increase the relatively small amplitudes of such conductive communication signals. The filter portion can be a high-pass filter or a bandpass filter adapted to separate an ECG signal from conductive communication signals. The message amplifier and/or filter 740 is an example of sense circuitry configured to produce a sensed signal using a sensing vector including at least two electrodes that are configured to be in contact with the patient.

The message decoder 738 can be configured to decode conductive communication signals received from an LP into a format that the controller 712 can understand. The specific type of decoding performed by the message decoder 738 depends upon the specific coding of the conductive communication signals received from an LP, e.g., on-off keying, frequency-shift keying, frequency modulation, or amplitude shift keying, but not limited thereto. It is also possible that the message decoder 738 is implemented within the controller 712, e.g., by a digital signal processor (DSP) of the controller 712.

The conductive communication transmitter 732 is configured to transmit (under the controller of the controller 712) conductive communication signals to one or more IMDs implanted within a patient. One example of a conductive communication signal that may be transmitted by the external device 109, such as an external programmer or a remote monitor, is an acknowledgement (ACK) sequence of conductive communication pulses, which informs one or more LPs that the external device 109 is in proximity to the LP(s) and/or other types of IMD(s) and capable of receiving data (encoded into conducted communicate pulses) from the LP(s) and/or other types of IMD(s). The conductive communication signals can also be used to program, interrogate, and/or obtain notifications and/or other types of diagnostic information from one or more LPs and/or other types of IMD(s).

The transmitter 732, in this example embodiment, is shown as including a message encoder and/or modulator 730 and an amplifier 736. The message encoder and/or modulator 730 can be configured to encode and/or modulate signals that are output from the controller 712 into a format that IMD(s), such as LP(s), can understand. The specific type of encoding performed by the message encoder depends upon the specific type of encoding the IMD(s) can understand, e.g., on-off keying, frequency-shift keying, frequency modulation, or amplitude shift keying, but not limited thereto. The amplifier 736 is coupled to the encoder/modulator 730 to increase amplitudes of pulses included in a conductive communication signals to a level sufficient to enable one or more IMD(s) to receive conductive communication signals from the external device 109. It is also possible that the message encoder and/or modulator 730 is implemented by the controller 712, e.g., by a DSP of the controller 712.

The controller 712 may receive ECG data and optionally displays an ECG using the display 716 and can also display information included in other data acquired from the implanted IMD(s) acquired through the encoded pulses included in conductive communication signals, such as battery voltage, sensed cardiac signal amplitude, and/or other system status information. The controller 712 also can accept input from a user via a user-interface 718, which can include, e.g., a keyboard and/or touch-screen, but is not limited thereto. Where the display 716 is a touch-screen type of display, the display 716 can also provide the user-interface 718, or at least a portion thereof. The controller 712 can also communicate over a network interface 720 to other data entry or display units, such as a handheld computer or laptop/desktop unit. The network interface 720 can be cabled or wireless and can also enable communication to a local area network or the Internet for greater connectivity. More specifically, the network interface 720 can be used to send ECG data, diagnostic data, and other types of data collected from one or more IMD(s) to a patient care network associated with a medical group and/or facility. For more specific examples, the network interface can include a Bluetooth antenna, a WiFi antenna, and/or an Ethernet connection, but is not limited thereto.

The controller 712, which can include one or more processors, and/or the like, can execute operations based on firmware stored in non-volatile memory (Flash), e.g., 118. The non-volatile memory can also be used to store parameters or values that are to be maintained when power is removed. The controller 712 can use volatile memory or random access memory (RAM) as general storage for information such as ECG data, status information, swap memory, and other data.

The external device 109 can include or be coupled to more than three external electrodes 115. For example, the external device 109 can included or be coupled to four, five, six, or seven external electrodes 115, but not limited thereto, wherein the greater the number of external electrodes the greater the number of potential communication vectors to test and select from.

At least some of the external electrodes 115 of the external device 109 can be used to sense ECG signals, as well as sense conductive communication signals output by one or more IMDs. It is also possible for the external electrodes 115 of the external device 109 to be used to receive electrogram (EGM) signal data included in conductive communication signals output by one or more IMDs, which EGM signal data can be received by the external device 109 (using the external electrodes 115) and used to reproduce one or more EGM signals that were sensed by one or more IMDs, wherein an EGM signal can also be referred to as an intracardiac electrogram (IEGM) signal. In addition to being able to communicate with one or more IMDs via conductive communication, the external device 109 can optionally have an antenna and RF communication capabilities that enable the external device 109 to wirelessly communicate with an implantable device, such as the ICM 104, via a wireless communication protocol, examples of which were discussed above. It would also be possible for the external device 109 to also include an inductive coil that enables the external device to perform inductive communication with an IMD that has such a capability.

The external device 109 can take many physical forms, but fundamentally it should be able to establish a conductive communication vector with the patient so that it can detect one or more IMDs' conductively communicated transmissions, decipher the communication protocol utilized by the IMD(s), and upload any acquired follow-up information to a patient care network, such as the Merlin.net™ patient care network operated by Abbott Laboratories (headquartered in the Abbott Park Business Center in Lake Bluff, Illinois).

For example, where the external device 109 has or is communicatively coupled to three external electrodes **115*a*, 115*b* and 115*c*, which can be referred to respectively as first, second, and third external electrodes, the external device can test and select among first, second, and third subsets of the external electrodes, wherein the first subset includes the first and second external electrodes (i.e., 115*a* and 115*b*), the second subset includes the first and third external electrodes (i.e., 115*a* and 115*c*), and the third subset includes the second and third external electrodes (i.e., 115*b* and 115*c*). In accordance with certain embodiments of the present technology, the external device 109** can identify which one of a plurality of the subsets, or more generally, which one of the plurality of possible communication vectors, is a preferred communication vector for communicating with an IMD. Where multiple IMDs are implanted within a patient, the external device can determine that different communication vectors are preferred for different IMDs. However, it is also possible that the external device may determine that a same communication vector is preferred for communicating with two or more different IMDs.

The external device 109 can be used to perform various methods described herein. For example, the external device 109 can perform the steps of a method described below with reference to FIG. 8C, which steps are described as being performed by the EMD. The external device 109 can additionally, or alternatively, be used to perform a method described below with reference to FIG. 11A. The external device 109 can additionally, or alternatively, be used to perform a method described below with reference to FIG. 11B. The external device 109 can additionally, or alternatively, be used to perform a method described below with reference to FIG. 12A or a method described below with reference to FIG. 12B. While in FIG. 7, the external device 109 is shown as including three external electrodes 115, the external device 109 can alternatively include as few as two external electrodes 115, or can alternatively include more than three external electrodes 115, depending upon the specific implementation. For example, in the below discussion of FIGS. 13A through 13D, the external device 109 is shown and described as including seven external electrodes 115.

Advertisement Sequences and Frames

In accordance with certain embodiments of the present technology, an LP 102 periodically outputs an advertisement sequence, using at least two of the two or more implantable electrodes of the LP, when the LP is not in an active conductive telemetry session with an external device 109. When an IMD (e.g., an LP 102) is not in an active conductive telemetry session with an external device, it could also be said that the IMD is in an inactive conductive telemetry session with the external device.

In accordance with certain embodiments, the advertisement sequence is a predetermined sequence (or one of a plurality of predetermined sequences) of conductive communication bit signatures that indicates to an external device 109 that an LP 102 (or other type of IMD) is implanted within a patient, and allows an active conductive telemetry session to be initiated and to take place when an open link command is sent from the external device 109 and received by the LP 102 (or other type of IMD). The advertisement sequence can also be referred to herein as a sniff sequence (or more succinctly as a sniff), an advertising sequence, an advertisement notice, or an advertising notice. The sniff is preferably transmitted relatively infrequently in order to conserve the battery of the LP 102. In accordance with certain embodiments, the sniff is transmitted by an LP 102 during a refractory period once every M cardiac cycles when the LP is not in an active conductive telemetry session with an external device 109, where M is an integer that is preferably greater than 1, e.g., M=6, 7, or 8, but is not limited thereto.

Figure 8A:
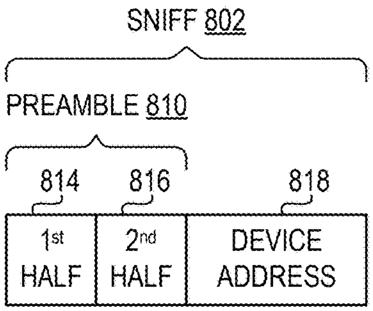
FIG. 8A illustrates an example format of an advertisement sequence transmitted by an IMD to enable an external device to detect the presence of the IMD and establish an active conductive telemetry session with the IMD.

FIG. 8A illustrates an example format of a sniff sequency 802, which as noted above, can also be referred to as a sniff 802, an advertisement sequence 802, an advertising sequence 802, an advertisement notice 802, or an advertising notice 802. Referring to FIG. 8A, the sniff 802 is shown as including a preamble 810, followed by a device address 818. In an embodiment, the preamble 810 is a byte (aka an octet of bits) that includes a first predetermined preamble portion 814 (aka a first nibble of 4 bits) having a first predetermine hex value and a second predetermined preamble portion 816 (aka a second nibble of 4 bits) having a second known hex value. The device address is one of a plurality (e.g., four) possible device addresses that corresponds to the type of IMD and/or the location of the IMD. For example, the LP 102*a* that is configured to be implanted in or on the right atrial chamber may have a first device address, and the LP 102*b* that is configured to be implanted in or on the right ventricular chamber may have a second device address, both of which are known by the external device 109 so that the external device can determine the type and/or location of the IMD that transmitted the sniff 802 based on the device address 818 included in the sniff 802 received by the external device 109. It would also be possible for the LP 102*a* to have one of two possible addresses, depending upon whether the LP 102*a* is a new device that still needs to be configured, or is an old device that has already been configured. Similarly, it would also be possible for the LP 102*b* to have one of two possible addresses, depending upon whether the LP 102*b* is a new device that still needs to be configured, or is an old device that has already been configured.

The external device 109, in response to receiving the sniff 802 from an LP 102, can transmit an open link command to the LP 102 that transmitted the sniff 802 in order to establish an active telemetry session with the IMD. If the LP 102 successfully receives the open link command from the external device 109, an active telemetry session can be established between the external device 109 and the LP 102.

While an active conductive telemetry session is established between the external device 109 and an LP 102 (or other type of IMD), conductive telemetry frames are used to transmit commands, markers and/or payload data between the external device 109 and the LP 102 (or other type of IMD). For much of the remainder of this discussion, it is assumed that the active conductive telemetry session being discussed is between the external device 109 and an LP 102. However, it should be understood that an active conductive telemetry session can alternatively, or additionally, be established between the external device 109 and another type of IMD, such as an ICM or an ICD.

Once an active conductive telemetry session is established between the external device 109 and an LP 102, the active conductive telemetry session can continue until an end telemetry session command is transmitted by the external device 109 to the LP 102 and is successfully received by the LP. When the LP receives and processes the close link command, the LP device will immediately stop all transmission of segments of frames and will revert back to periodically transmitting sniffs. If the external device 109 has established active conductive telemetry sessions with multiple LPs 102 during the same period of time, the external device 109 can transmit the close link command to all of the LPs 102, or the external device 109 can transmit the close link command selectively to one or more LP(s) 102 without changing the existing telemetry session established with one or more other LP(s) 102. An active conductive telemetry session may also be terminated by an LP 102 without the LP receiving the close link command from the external device, e.g., in response to the LP 102 having not received a valid command from the external device for at least a specified period of time (e.g., 6, 8, or 10 seconds, but not limited thereto) or for at least a specified number of cardiac cycles (e.g., 7, 8, 9, or 10 cardiac cycles, but not limited thereto). An example reason that the LP 102 may not receive a valid command from the external device 109 for at least the specified period of time or the specified number of cardiac cycles can be because one or more of the external electrodes 115 is/are no longer in physical contact with the skin of the patient within which the LP 102 is implanted.

Where conductive communication signals are transmitted from an external device 109 to an LP 102 (or other type of IMD), the conductive communication signals can also be referred to as conductive external-to-implant (e2i) communication signals, or more succinctly as conductive e2i signals. Where the external device 109 is a programmer, the conductive e2i signals transmitted by the external programmer to the LP 102 (or other type of IMD) can be referred to more specifically as conductive programmer-to-implant (p2i) communication signals, or more succinctly as conductive p2i signals. In other words, conductive p2i signals are a specific type of conductive e2i signals. Where the conductive communication signals are transmitted from an LP 102 (or other type of IMD) to an external device 109, the conductive communication signals can also be referred to as conductive implant-to-external (i2e) communication signals, or more succinctly as conductive i2e signals. Where the external device 109 is a programmer, the conductive i2e signals transmitted by an LP 102 (or other type of IMD) to the external programmer can be referred to more specifically as conductive implant-to-programmer (i2p) communication signals, or more succinctly as conductive i2p signals. In other words, conductive i2p signals are a specific type of conductive i2e signals. Conductive communication signals are also referred to sometimes as conducted communication signals, and these terms are often used interchangeably.

Frames occur when an LP 102 is in an active conductive telemetry session with an external device 109. As will be appreciated from the following discussion, each frame can include both i2e signals and e2i signals. Accordingly, a frame can be considered a period of time during which conductive communication pulses are transmitted between an LP 102 and an external device 109 in one or both directions. During an active conductive telemetry session, multiple frames can occur during a same refractory period of a same cardiac cycle, and frames can occur during consecutive cardiac cycles (within successive refractory periods).

Figure 8B:
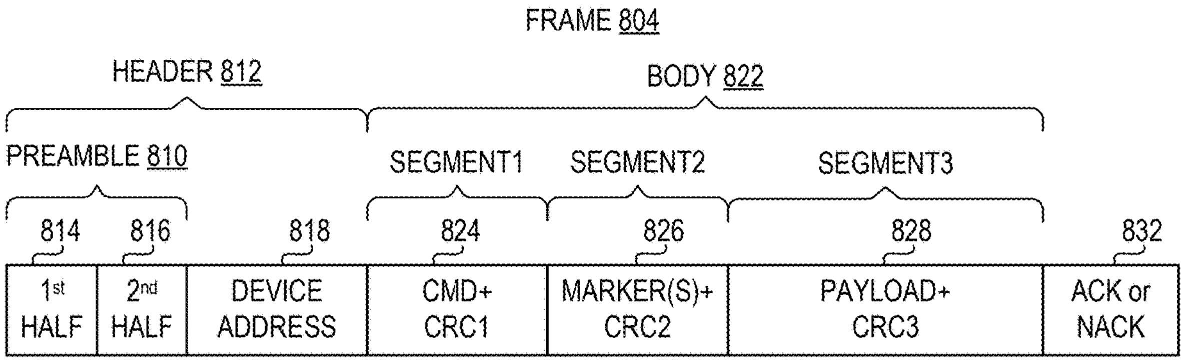
FIG. 8B illustrates an example format of a frame, according to an embodiment of the present technology, which is used for supporting conductive communication between an external device and an IMD during an active conductive telemetry session therebetween.

FIG. 8B illustrates an example format of a frame 804, according to an embodiment of the present technology. The frame is shown as including a header 812 followed by a body 822. An acknowledgement (ACK) or a negative acknowledgement (NACK) 832 can follow the body 822, when a write command is included in a frame, wherein the ACK or NACK may be used to indicate whether a cyclic redundancy check (CRC) code for the data (written to the LP or other type of IMD in response to a write command transmitted by the external device) is valid. More specifically, an IMD that receives a write command from an external device, can use the ACK to indicate that payload data received from an external device is valid as determined based on the associated CRC code, and can use the NACK to indicate that the payload data received from the external device is invalid as determined based on the associated CRC code. Accordingly, it should be appreciated that not all frames will include a ACK or a NACK 832. In certain embodiments, when an IMD issues a NACK, it does not write the payload data to its memory (e.g., 118).

In certain embodiments, the header 812 has the same format as the sniff 802, which was described above with reference to FIG. 8A. Accordingly, the header 812 includes a preamble 810, followed by an IMD address 818. It would also be possible for the header 812 of the frame 804 to have a different format than the sniff 802. However, when discussing the frame 804, unless stated otherwise, it is assumed that the header 812 has the same format as the sniff 802. In an embodiment, the preamble 810 is a byte (aka an octet of bits) that includes a first predetermined preamble portion 814 (aka a first nibble of 4 bits) having a first predetermine hex value and a second predetermined preamble portion 816 (aka a second nibble of 4 bits) having a second known hex value. The IMD address is one of a plurality (e.g., four) possible addresses that corresponds to the type of IMD and/or the location of the IMD.

The body 822 of the frame 804 includes a plurality of segments 824, 826, and 828, which are also labeled segment1, segment2, and segment 3 in FIG. 8B. The first segment 824 (i.e., segment1) includes a command, optionally followed by one or more command arguments, and a first CRC code (i.e., CRC1). The second segment 826 (i.e., segment2) includes marker data and second CRC code (i.e., CRC2). The third segment 828 (i.e., segment3) includes payload data and a third CRC code (CRC3).

The command and argument(s) included in the first segment (i.e., segment1) is transmitted by the external device 109 to the LP 102 (or other type of IMD) to cause the LP 102 (or other type of IMD), to which the command is sent, to perform a specific operation specified by the command. Example types of commands include an open link command (aka a start telemetry session command), a close link command (aka an end telemetry session command), a keep link alive command, a read type command, and a write type command, just to name a few. Each command included within the first segment (i.e., segment1) may also be followed by one or more arguments. The first CRC code (i.e., CRC1) that is included in the first segment (i.e., segment1) is used by the LP 102 (or other type of IMD) that receives the command to determine whether the command included in the first segment (i.e., segment1) has been decoded correctly by the LP 102 (or other type of IMD), and more generally, is used by the receiving LP 102 (or other type of IMD) to determine whether there is an error in the received and decoded command. If there is an error, the command is rejected and thus not executed.

The marker data included in the second segment (i.e., segment2) is used by the LP 102 (or other type of IMD) to inform the external device 109 of cardiac events detected by the LP 102 (or other type of IMD). For example, markers can be used to inform the external device of R-waves, P-waves, tachycardia detections, atrial fibrillation detections, and/or the like. Accordingly, the marker data can also be referred to herein as cardiac event data. The second CRC code (i.e., CRC2) that is included in the second segment (i.e., segment2) is used by the external device 109 that receives the marker data (aka cardiac event data) to determine whether the marker data included in the second segment (i.e., segment2) has been decoded correctly by the external device 109, and more generally, is used by the external device 109 to determine whether there is an error in the received and decoded marker data. If there is an error, the marker data is rejected and thus not used.

The payload data included in the third segment (i.e., segment3) can be, for example, data this is being read by the external device 109 from the LP 102 (or other type of IMD), or data this is being written by the external device 109 to the LP 102 (or other type of IMD), depending upon whether the command included in the segment1 is a read type command or a write type command. The third CRC code (i.e., CRC3) that is included in the third segment (i.e., segment3) is used by the external device 109 that receives data this is read, or by the LP 102 (or other type of IMD) to which data is written, to determine whether there is an error in the data that is read or written, and thus, the data should be reread or rewritten using another frame.

A benefit of each of the segments (segment1, segment2, and segment3) of the body 822 including its own respective CRC code, is that a device that is decoding the frame need not wait until the end of the frame to determine whether or not the frame being decoded, or a portion thereof, is valid or not. Additionally, where each of the segments (segment1, segment2, and segment3) of the body 822 of a frame 804 includes its own respective CRC code, if the external device 109 is only interested certain segment(s) of the frame but not others, the external device 109 can utilize a valid segment that it received even if there was an error in another segment of the same frame. For example, if the external device 109 is only interested in the payload data received from an LP in response to a read type command, but not the marker data (or if the payload data is useful independent of the marker data), the external device 109 can separately determine whether the payload data is valid based on the CRC3 and use that data, even if the marker data is found to be invalid based on the CRC2. More generally, where each of the segments (segment1, segment2, and segment3) of the body 822 of a frame 804 includes its own respective CRC code, the external device 109 can utilize one or more valid segments even if one or more other segments is/are invalid, as determined by the external device based on the CRC codes included in the respective segments.

Figure 8C:
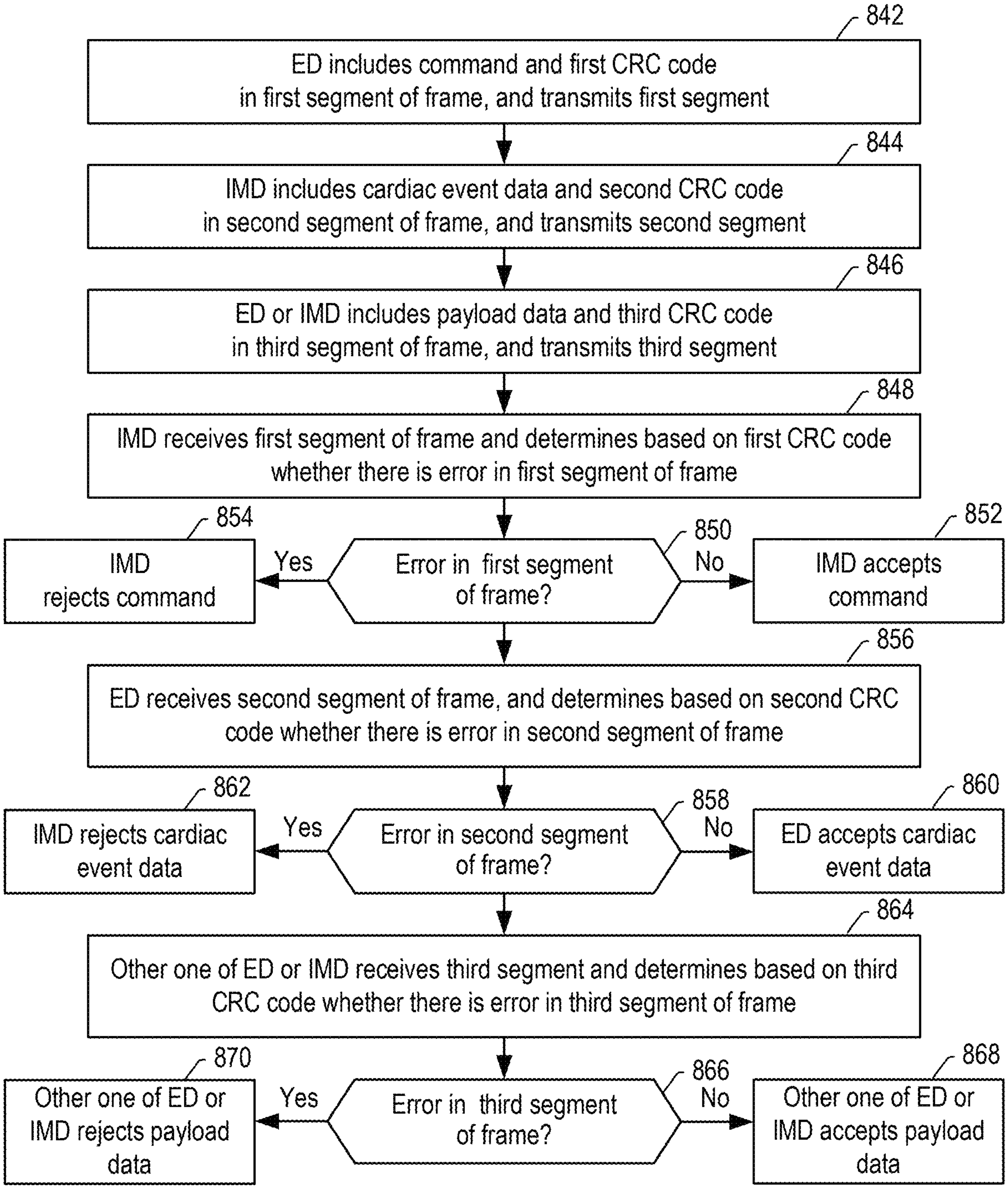
FIG. 8C is a high level flow diagram used to summarize methods, according to certain embodiments of the present technology, used to provide communication between an external device and an IMD using a frame, such as the frame introduced in FIG. 8B.

FIG. 8C is a high level flow diagram used to summarize methods, according to certain embodiments of the present technology, used to provide communication between an external medical device (EMD) and an IMD using a frame, such as the frame 804 introduced in FIG. 8B, wherein the frame comprises a header (e.g., 812) and a body (e.g., 822). In an embodiment, the EMD and the IMD that perform the methods summarized with reference to FIG. 8C can be, respectively, an external device 109 and an LP 102, example details of which were described above with reference to FIGS. 1 through 7. The methods summarized with reference to FIG. 8C can be performed during an active conductive telemetry session between the external device 109 and the LP 102 (or other type of IMD). Referring to FIG. 8C, step 842 involves the EMD including, within a first segment (e.g., 824) of the frame, a command and a first cyclic redundancy check (CRC) code generated by the EMD, and the EMD transmitting the first segment of the body of the frame. Step 844 involves the IMD including, within a second segment (e.g., 826) of the frame, cardiac event data (aka marker data) and a second CRC code generated by the IMD, and the IMD transmitting the second segment of the body of the frame. Step 846 involves one of the EMD and the IMD including, within a third segment (e.g., 826) of the frame, payload data and a third CRC code generated by the one of the EMD and the IMD, and the one of the EMD and the IMD transmitting the third segment of the body of the frame. Which specific one of the EMD or the IMD generates the payload data and the third CRC code to be included in the third segment of the body of the frame can depend on the command included in the first segment (e.g., 824) of the body of the frame. For example, where the command included in the first segment of the body of the frame is a read type of command that is used by the EMD to read data from the memory (e.g., 118) of the IMD, then the payload data will include data read from the IMD, and thus the payload data and the third CRC code will be generated by the IMD responsive to the read type of command received from the EMD in the first segment of the body of the frame. By contrast, where the command included in the first segment of the body of the frame is a write type of command that is used by the EMD to write data to the memory (e.g., 118) of the IMD, then the payload will include data being written by the EMD to the IMD, and thus the payload data and the third CRC code will be generated by the EMD.

Still referring to FIG. 8C, step 848 involves the IMD receiving the first segment of the body of the frame and determining based on the first CRC code whether there is an error in the first segment of the body of the frame. At step 850 there is a determination of whether there was an error in the first segment of the body of the frame. If the answer to the determination at step 852 is No, then flow goes to step 852 and the IMD accepts the command. If the answer to the determination at step 852 is Yes, then flow goes to step 854 and the IMD rejects the command, and thus, does not perform the command. More generally, the IMD either accepts the command included in the first segment in response to determining that the first segment does not include an error, or does not accept (aka rejects) the command included in the first segment in response to determining that the first segment includes an error.

Step 856 involves the EMD receiving the second segment of the body of the frame and the EMD determining based on the second CRC code whether there is an error in the second segment of the body of the frame. At step 858 there is a determination of whether there was an error in the second segment of the body of the frame. If the answer to the determination at step 858 is No, then flow goes to step 860 and the EMD accepts the cardiac event data. If the answer to the determination at step 860 is Yes, then flow goes to step 882 and the EMD rejects the command, and thus, does not perform the command. More generally, the EMD either accepts the cardiac event data included in the second segment in response to determining that the second segment does not include an error, or rejects the cardiac event data included in the second segment in response to determining that the second segment include an error.

Step 864 involves the other one of the IMD or the EMD (i.e., the one that did not transmit the third segment) receiving the third segment of the body of the frame and determining based on the third CRC code whether there is an error in the third segment of the body of the frame. At step 866 there is a determination of whether there was an error in the third segment of the body of the frame. If the answer to the determination at step 866 is No, then flow goes to step 868 and the payload data is accepted by the other one of the IMD or the EMD (i.e., the one that did not transmit the third segment). If the answer to the determination at step 866 is Yes, then flow goes to step 870 and the payload is rejected. More generally, the other one of the IMD or the EMD either accepts the payload data included in the third segment in response to determining that the third segment does not include an error, or rejects the payload data included in the third segment in response to determining that the third segment includes an error.

Referring briefly back to FIG. 8B, in certain embodiments the header (e.g., 812) is always generated by the IMD and includes a preamble (e.g., 810) and a device address (e.g., 818) of the IMD that generated the header. In certain embodiments, the frame also includes one of an acknowledgement (ACK) or a negative acknowledgement (NACK) that specifies, respectively, whether payload data being written to memory (e.g., 118) of the IMD is valid or not, as determined based on the third CRC code. This enables the EMD to know whether or not the EMD should retransmit certain payload data that it is attempting to write to memory of the IMD. In certain embodiments, when an IMD issues a NACK, it does not write the payload data to its memory. By contrast, when an IMD issues an ACK, that is confirmation that the IMD wrote the payload data to its memory.

The benefit of using three different CRC codes is that parts of the frame may be used even if other parts include errors. For example, the command is accepted and performed by the IMD, in response to the IMD determining there is not an error in the first segment of the body of the frame, regardless of whether there is an error in the second segment and/or the third segment of the body of the frame. For another example, the cardiac event data is accepted by the external device, in response to the external device determining that there is not an error in the second segment of the body of the frame, regardless of whether there is an error in the first segment and/or the third segment of the body of the frame. For a further example, the payload data may be accepted by the one of the IMD or the external device (which did not include the third CRC code in the third segment), in response to determining that there is not an error in the third segment, regardless of whether there is an error in the first segment or/or the second segment of the body of the frame.

Referring again to FIG. 8C, the order in which the various steps are actually performed may differ from what is shown in FIG. 8C. Accordingly, the methods summarized with reference to FIG. 8C are not limited to the specific order of the steps shown in FIG. 8C. For example, step 848 (or at least the receiving portion of step 848) can be performed between steps 842 and 844. For another example, step 856 (or at least the receiving portion of step 856) can be performed between steps 844 and 846. Further, it should be appreciated that the boundaries of steps in FIG. 8C have often been defined herein for the convenience of the description. Accordingly, it should be appreciated that some of the steps shown in and described with reference to FIG. 8C can be separated into multiple steps. For example, step 848 could be described as two separate steps, one of which includes receiving the first segment of the frame, and another one of which includes determining based on the first CRC code whether there is an error in the first segment of the frame. For another example, step 856 could be described as two separate steps, one of which includes receiving the second segment of the frame, and another one of which includes determining based on the second CRC code whether there is an error in the second segment of the frame. For still another example, step 864 could be described as two separate steps, one of which includes receiving the third segment of the frame, and another one of which includes determining based on the third CRC code whether there is an error in the third segment of the frame.

Referring briefly back to FIG. 8A, assume for example that the preamble 810 of the sniff 802 includes one byte (i.e., 8 bits), and the IMD address 818 includes another type (i.e., another 8 bits), then the sniff 802 would include a total of 2 bytes (i.e., 16 bits). This could also mean that the header 812 of a frame 804 also includes 2 bytes (i.e., 16 bits), in those embodiments where the sniff 802 and the header 812 of a frame 804 have the same format. The device address 818 can, e.g., also be a byte in length. Each of the segments of the body 822 can, e.g., include multiple bytes, with each CRC being a byte in length. Other variations are also possible and are within the scope of the embodiments described herein. For example, the preamble 810 can alternatively be larger or smaller than one byte, and/or the IMD address 818 can alternatively be larger or smaller than one byte. Each bit in the sniff 802 and the frame 804 is a binary bit that can have a "1" bit value, or a "0" bit value. The "1" bit value can be communicated using a respective conductive communication signature within a temporal window, and the "0" bit value can be communicated using another respective conductive communication signature within a temporal window. Each such temporal window has a specified duration, e.g., about 30 microseconds (us), but is not limited thereto.

Figure 9A:
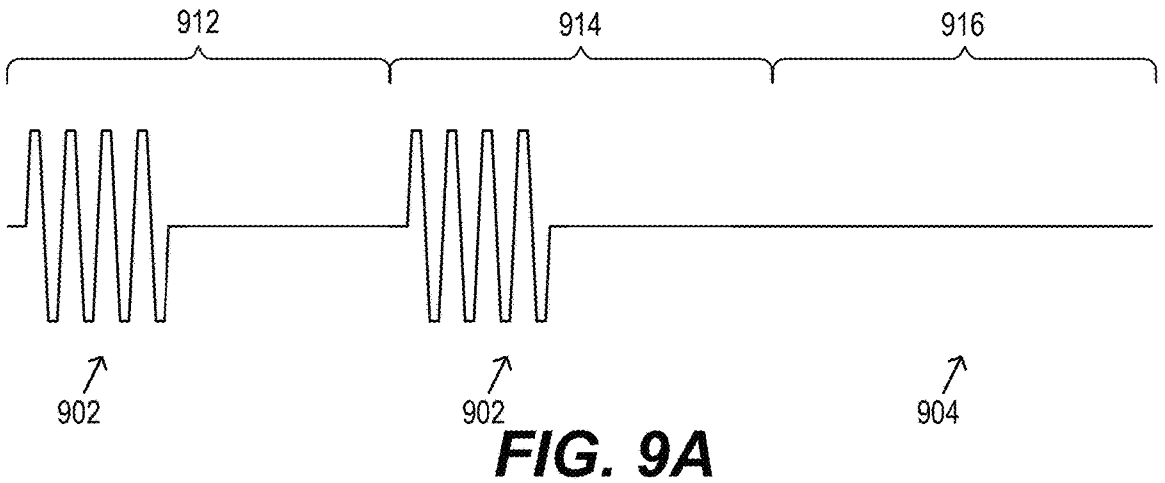
FIG. 9A illustrates example conductive communication signatures used to represent a "1" bit value and to represent a "0" bit value within different temporal windows.
Figure 9B:
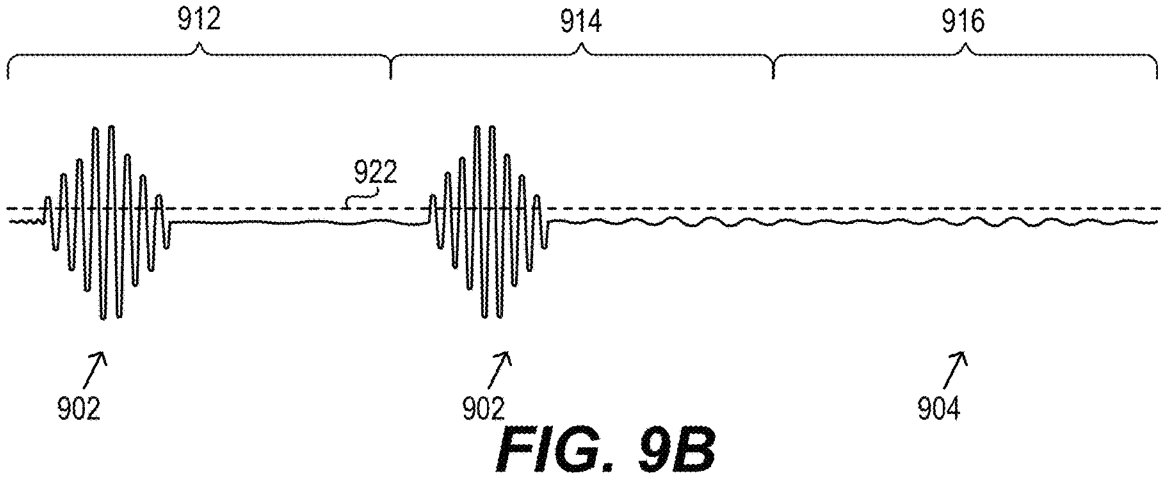
FIG. 9B illustrates a conductive communication signal including instances of the signatures represented in FIG. 9A, after the conductive communication signal has been transmitted by an IMD through patient tissue and received by an external device and amplified and filtered by the external device.

FIG. 9A illustrates an example conductive communication signature 902 that is used to represent a "1" bit value within each of temporal windows 912, and 914, and an example conductive communication signature 904 used to represent a "0" bit value within a further temporal window 916, wherein each of the temporal windows 912, 914, and 916 is, for example, about 30 us. In this example embodiment, the conductive communication signature 902 that is used to represent a "1" bit value includes four bi-phasic pulses within a temporal window, and the conductive communication signature 902 that is used to represent a "0" bit value includes no bi-phasic pulses within a temporal window. For the remainder of this description it is assumed that these signatures 902 and 904 shown in FIG. 9A are what are being used to represent, respectively, a "1" bit value and a "0" bit value. However, it should be understood that it would also be possible for the conductive communication signature 902 to be used to represent a "0" bit value, and the conductive communication signature 904 to be used to represent a "1" bit value, or that a completely different respective conductive communication signature is used to represent a "1" bit value and/or a completely different respective conductive communication signature is used to represent "0" bit value. FIG. 9B illustrates a conductive communication signal including instances of the signatures represented in FIG. 9A, after the conductive communication signal has been transmitted by an IMD through patient tissue and has been received by an external device and amplified and filtered by the external device. FIG. 9B can alternatively illustrate a conductive communication signal including instances of the signatures represented in FIG. 9A, after the conductive communication signal has been transmitted by an external device through patient tissue and has been received by an IMD and amplified and filtered by the IMD. FIG. 9B can alternatively illustrate a conductive communication signal including instances of the signatures represented in FIG. 9A, after the conductive communication signal has been transmitted by a first IMD and received by a second IMD and amplified and filtered by the second IMD.

In certain embodiments, the device (that is receiving a conductive communication signal from another device) decodes a conductive communication signal in part by detecting edges of a received conductive communication signal, i.e., by performing edge detections. More specifically, an edge is detected when a received conductive communication signal, after being amplified and filtered, crosses an edge detection threshold (e.g., transitions from being below the edge detection threshold to being above the edge detection threshold). In order for the edge detections to be accurately detected, the receiving device (e.g., the external device 109) needs to use an appropriate edge detection threshold. This is because if the edge detection threshold is set too low, then noise can cause inappropriate edge detections to be triggered. Conversely, if the edge detection threshold is set too high, then edge detections can be missed when they should have been triggered. In other words, an edge detection threshold that is set too low can result in false positive edge detections, and an edge detection threshold that is set too high can results in false negative edge detections. Such false positive edge detections and/or false negative edge detections can, for example, prevent a device (e.g., an external device or an IMD) from being able to receive and decode valid messages. Certain embodiments of the present technology, which are described below with reference to FIGS. 10 and 11, are used to define and utilize an appropriate edge detection threshold.

Figure 10:
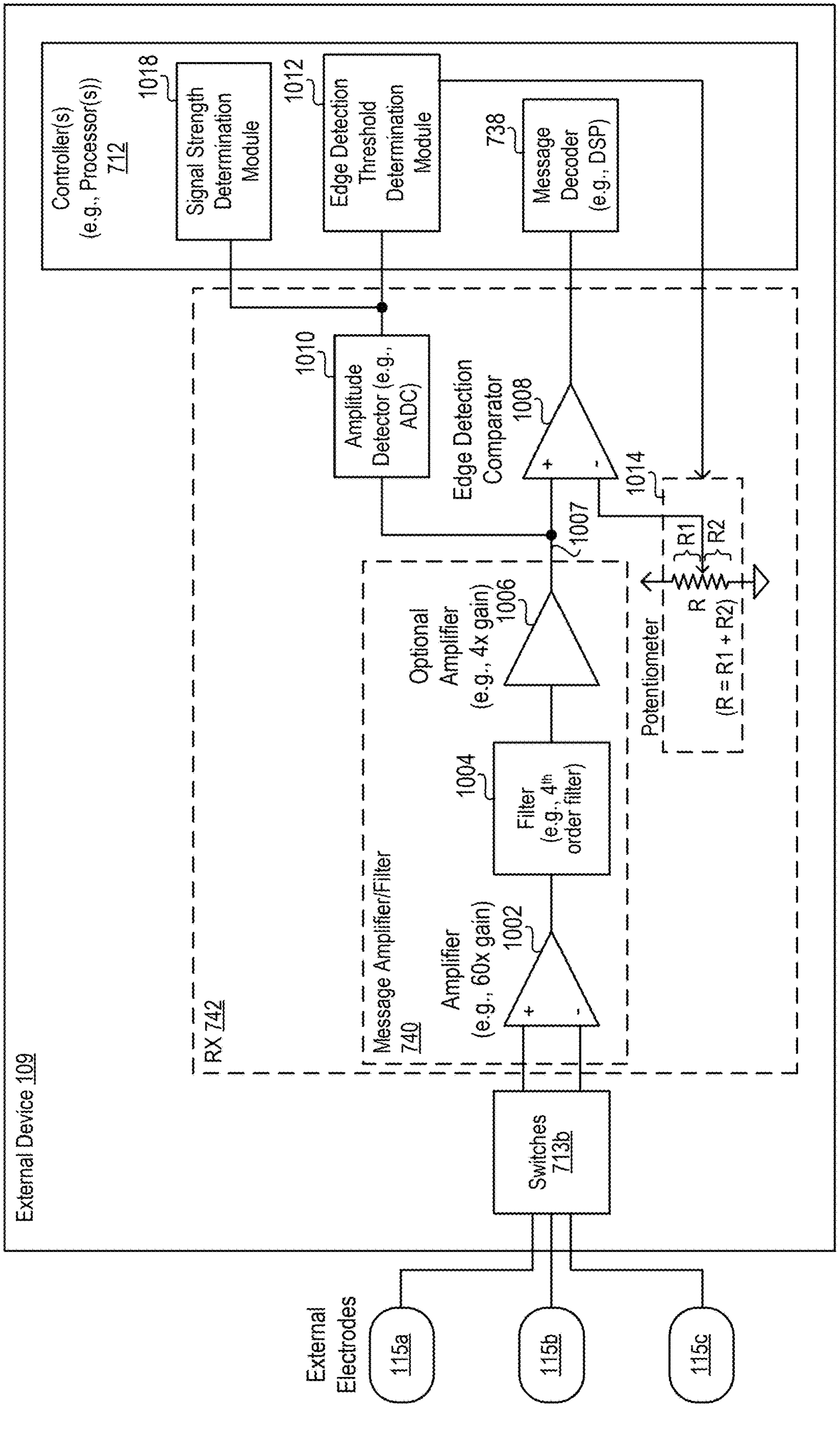
FIG. 10 is a high level block diagram that is used describe how an edge detection threshold may be determined by an external device that is used to perform conductive communication with an IMD, in accordance with an embodiment of the present technology.

FIG. 10 is a high level block diagram that is used describe how an edge detection threshold may be determined by an external device 109 that is used to perform conductive communication with an LP 102 (or other type of IMD). Elements in FIG. 10 that are the same as elements introduced in earlier described FIGS. are labeled the same in FIG. 10, and need not be described in detail again. Referring to FIG. 10, the external device 109 is shown as includes switches 713*b* that are used to electrically connect selected ones of the external electrodes 115 to differential inputs of the message amplifier/filter 740 of the conductive communication receiver (RX) 742. The message amplifier/filter 740 is shown as including an amplifier 1002, followed by a filter 1004, which is optionally followed by another amplifier 1006. The switches 713 may, for example, electrically connect the external electrodes 115*a* and 115*b*, respectively, to the non-inverting (+) and inverting (−) inputs of the amplifier 1002. The amplifier 1002 amplifies a difference between the voltages sensed by the external electrodes 115*a* and 115*b* (or some other electrode sensing vector) and provides an amplified signal to the filter 1004. The filter 1004 can be, e.g., a fourth order bandpass filter, but is not limited thereto. The filtered signal output by the filter 1004 is then optionally amplified by another amplifier 1006, which may be used to compensate for attenuation caused by the filter 1004. The amplifier 1002 may have a relatively high gain (e.g., 60×) to amplify the relatively low amplitude signals received by the external device 109 from an LP 102 (or other type of IMD). The optional amplifier 1006 will likely have a relatively low gain (e.g., 4×) compared to the gain of the amplifier 1002. The signal 1007 that is output by the message amplifier/filter 740 can be referred to as an amplified and filtered received conductive communication signal 1007, or more succinctly as a received conductive communication signal. The received conductive communication signal 1007 is shown as being provided to an edge detection comparator 1008. The edge detection comparator 1008 compares the received conductive communication signal 1007 to an edge detection threshold, which is determined in accordance with an embodiment of the present technology, as will be described below. The edge detection comparator 1008 can also be referred to herein as comparator circuitry 1008 configured to produce edge detections.

Still referring to FIG. 10, the received conductive communication signal 1007 is also provided to an amplitude detector 1010. In an embodiment, the amplitude detector 1010 is implemented using an analog-to-digital converter (ADC). Outputs of the amplitude detector 1010 are provided to an edge detection threshold determination module 1012, which can be implemented by the controller 712, using hardware, firmware, and/or software thereof, or alternatively can be implemented external to the controller 712. The edge detection threshold determination module 1012, or more generally the controller 712, determines a noise baseline of signals received by the RX 742, and sets the edge detection threshold at an appropriate level slightly above the noise baseline. The purpose of setting the edge detection threshold slightly above the noise baseline is to prevent noise from inappropriately triggering edge detections. However, as noted above, the edge detection threshold should not be set too high, because doing so can cause edge detections to be missed when they should have been triggered.

In accordance with an embodiment, the noise baseline is determined by determining an average of a plurality of (e.g., 2, 3, 5 or 10) amplitude values (e.g., ADC count values) output by the amplitude detector 1010, when such amplitude values are not samples of pulses included in a sniff or a frame. In accordance with another embodiment, the noise baseline is determined by determining a maximum (aka peak) value of a plurality (e.g., 2, 3, 5 or 10) amplitude values (e.g., ADC count values) output by the amplitude detector 1010, when such amplitude values are not samples of pulses included in a sniff or a frame. In accordance with an embodiment, where the amplitude detector 1010 is implemented as an ADC, the count values output by the ADC may optionally be multiplied by a conversion factor, to convert count values to voltage amplitude values. Other variations are also possible and within the scope of the embodiments described herein.

One or more equations, lookup tables, or the like, can be used to specify an edge detection threshold based on the noise baseline such that the edge detection threshold is above the noise baseline. In an embodiment, the equation Edge Detection Threshold=Scaling Multiplier*Noise Baseline is used, wherein the Noise Baseline is determined based on signal amplitude measurements produced by the Amplitude Detector 1010, which as noted above can be implemented as an ADC, and the Scaling Multiplier is determined using empirical data and/or simulations. The same Scaling Multiplier can be used regardless of the Noise Baseline, or different Scaling Multipliers can be used for different ranges of values for the Noise Baseline, e.g., a first Scaling Multiplier can be used when the Noise Baseline is within a first range, and a second Scaling Multiplier can be used when the Noise Baseline is within a second range, etc., depending upon how many ranges are defined.

In another embodiment, the equation Edge Detection Threshold=Noise Baseline+Offset is used, wherein the Noise Baseline is determined based on signal amplitude measurements produced by the Amplitude Detector 1010, which as noted above can be implemented as an ADC, and the Offset is determined using empirical data and/or simulations. The same Offset can be used regardless of the Noise Baseline, or different Offsets can be used for different ranges of values for the Noise Baseline, e.g., a first Offset can be used when the Noise Baseline is within a first range, and a second Offset can be used when the Noise Baseline is within a second range, etc., depending upon how many ranges are defined.

In an embodiment, the equation Edge Detection Threshold=Scaling Multiplier*Noise Baseline+Offset is used, wherein the Noise Baseline is determined based on signal amplitude measurements produced by the Amplitude Detector 1010, which as noted above can be implemented as an ADC, and the Scaling Multiplier and the Offset are determined using empirical data and/or simulations. The same Scaling Multiplier and Offset can be used regardless of the Noise Baseline, or different Scaling Multipliers and/or Offsets can be used for different ranges of values for the Noise Baseline, e.g., a first Scaling Multiplier and a first Offset can be used when the Noise Baseline is within a first range, and a second Scaling Multiplier and a second Offset can be used when the Noise Baseline is within a second range, etc., depending upon how many ranges are defined. Use of different scaling multipliers and/or offsets, based on whether the noise baseline is within a first range, second range, etc., is one way that different equations are used depending upon which range the noise baseline is within.

It should also be appreciated that other equations, besides those described above, can alternatively be used to determine the Edged Detection Threshold based on the determined Noise Baseline, such that the Edged Detection Threshold is above the Noise Baseline, while still being within the scope of the embodiments describe herein. In still other embodiments, one or more look up tables (LUTs) can be used, instead of one or more Equation(s), to determine the Edge Detection Threshold based on the Noise Baseline, such that the Edge Detection Threshold is above the Noise Baseline.

Once the edge detection threshold is determined by the controller 712, or the edge detection threshold determination module 1012 thereof, the controller 712 can control a potentiometer 1014, or the like, to set the edge detection threshold that is used by the edge detection comparator 1008. It would also be possible to use other circuitry, in place of the potentiometer 1014, to set the edge detection threshold that is used by the edge detection comparator 1008. For example, a digital-to-analog converter (DAC) can be used in place of the potentiometer 1014. Other variations are also possible and within the scope of the embodiments of the present technology.

Still referring to FIG. 10, the outputs of the amplitude detector 1010 are also shown as being provided to a signal strength determination module 1018, which can be implemented by the controller 712. The signal strength determination module 1018 can be used to monitor conductive communication quality, which in turn can be used in various different manners, such as to test different combinations of electrodes 115 that may be used to receive conductive communication signals from an LP 102 (or other type of IMD), and select a preferred combination of external electrodes 115 to use for receiving conductive communication signals from the LP 102 (or other type of IMD).

The edges detection outputs produced by the edge detection comparator 1008, which outputs can also be referred to as edge detections, or edge detection triggers, are provided to the message decoder 738, as shown in FIG. 10. The message decoder 738 converts edge detections (received from the edge detection comparator 1008) to bits, each of which bits can have a "1" bit value or a "0" bit value. Based on the decoded bits, the message decoder 738 can detect sniffs 802, or portions thereof, such as the preamble 810, and the device address 818, described above with reference to FIG. 8A. Based on the decoded bits, the message decoder 738 can also detects portions of a frame 804, described above with reference to FIG. 8B, such as the preamble 810, the device address 818, and one or more segments of the body 822 of the frame 804.

As explained above, FIG. 9A illustrates an example conductive communication signature 902 that is used to represent a "1" bit value within each of temporal windows 912, and 914, and an example conductive communication signature 904 used to represent a "0" bit value within a further temporal window 916, wherein each of the temporal windows 912, 914, and 916 have a same duration, e.g., about 30 usec, but not limited thereto. FIG. 9B, by contrast, illustrates a conductive communication signal including these instances of the signatures, after the conductive communication signal has been transmitted by an LP 102 through patient tissue and received by an external device 109, and amplified and filtered by the external device (e.g., using the amplifier 1002, the filter 1004, and optionally also the amplifier 1006). In other words, the conductive communication signal shown in FIG. 9B illustrates an example of the conductive communication signal 1007 in FIG. 10 that is provided to the edge detection comparator 1008. Also shown in FIG. 9B is an example of the edge detection threshold 922 determined by the controller 712 (or more specifically the edge detection threshold determination module 1012 thereof) and is provided by the potentiometer 1014 in FIG. 10 (or some other circuitry, such as a DAC) to the reference input of the edge detection comparator 1008 in FIG. 10.

Figure 11A:
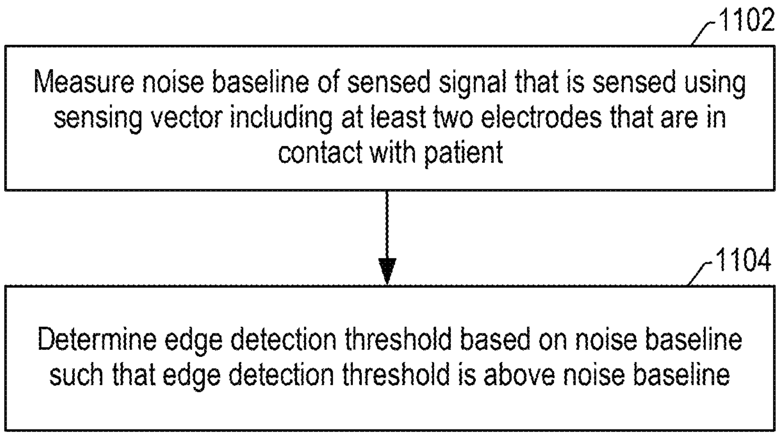
FIG. 11A is a high level flow diagram used to summarize methods, according to certain embodiments of the present technology, used to determine an edge detection threshold for use when performing conductive communication.
Figure 11B:
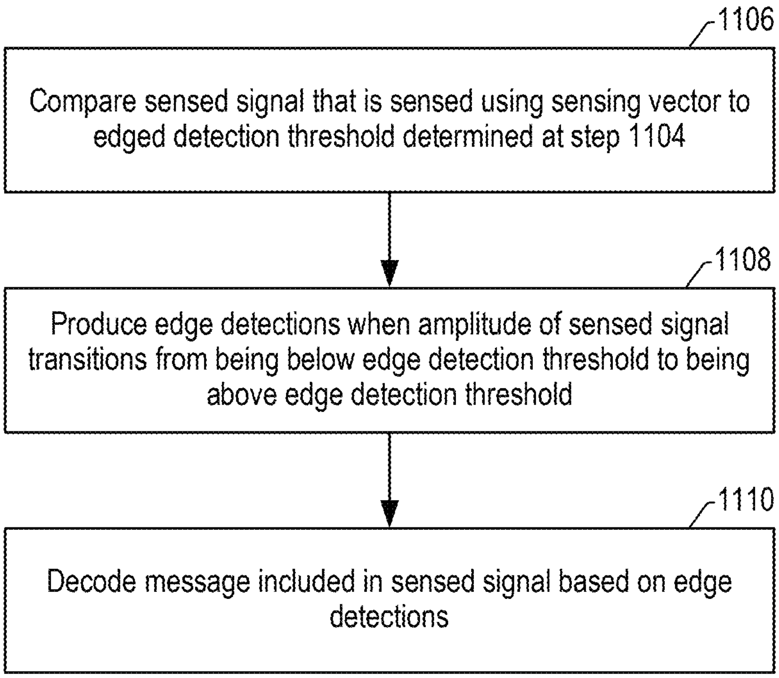
FIG. 11B is a high level flow diagram used to summarize methods, according to certain embodiments of the present technology, for using an edge detection threshold to produce edge detections and decode a received conductive communication signal.

The high level flow diagrams described with reference to FIGS. 11A and 11B will now be used to summarize methods according to certain embodiments of the present technology. More specifically, FIG. 11A is a high level flow diagram used to summarize methods, according to certain embodiments of the present technology, used to determine an edge detection threshold for use when performing conductive communication. FIG. 11B is a high level flow diagram used to summarize methods, according to certain embodiments of the present technology, for using an edge detection threshold to produce edge detections and decode a received conductive communication signal. Such methods can be used, for example, by the external device 109 to receive and decode a sniff 802 or a portion of a frame 804 that is transmitted by an LP 102 implanted in a patient, wherein the external device 109 includes or is communicatively coupled to two or more external electrodes 115 that are in contact with skin of the patient. More generally, such methods can be used by an external device 109 to receive and decode i2e communications. It would also be possible for such methods to be used by an LP 102 (or other type of IMD) during i2i communications. In an embodiment where an IMD (e.g., 102, 104, 106) performs one or more of the methods described below with reference to FIGS. 11A and 11B, such an IMD can include a conductive communication receiver similar to the conductive communication receiver 742 described above with reference to FIG. 10, and more specifically, can include a message amplifier/filter (similar to 740 shown in FIG. 10), an edge detector comparator (similar to 1008 in FIG. 10), an amplitude detector (similar to 1010 in FIG. 10), and the controller (e.g., 112) of the IMD can include modules (e.g., 1012 and 1018 in FIG. 10) and a message decoder (similar to 728 in FIG. 10) that are used to implement such method(s).

Referring to FIG. 11A, step 1102 involves measuring a noise baseline of a sensed signal that is sensed using a sensing vector including at least two electrodes (e.g., 115) that are in contact with a patient. Step 1104 involves determining an edge detection threshold based on the noise baseline, measured at step 1102, such that the edge detection threshold is above the noise baseline. Referring briefly back to FIG. 10, in accordance with certain embodiments, the measuring of the noise baseline of the sensed signal at step 1102 can be performed by the controller 712. More specifically, the controller 712 can determine an average or a maximum (aka peak) of a plurality of amplitude measurement (e.g., count values) of the sensed signal produced by the amplitude detector 1010, which as noted above, can be implanted using an ADC. The sensing vector used to sense the sensing signal can be any combination of the external electrodes 115, selecting using the switches 713*b*. Further, as explained above, the sensed signal can be amplified and filtered, by the amplifier 1002 and the filter 1004 (and optionally also the amplifier 1006) before the noise baseline of the sensed signal is measured at step 1102. In certain embodiments the measuring of the noise baseline is achieved by providing the sensed signal to an ADC, after the sensed signal has been amplified and filtered, to thereby producing a plurality of ADC count values. The noise baseline can then be determined based on one or more of the ADC count values produced using the ADC.

Step 1104 can then be performed by the controller 712 using one or more equations or one or more look up tables to define the edge detection threshold above the noise baseline determined at step 1102. Examples of such equations were described above, and thus, need not be described again. In an embodiment, a same equation is used to specify the edge detection threshold based on the noise baseline regardless of a value of the noise baseline. In another embodiment, a first equation is used to specify the edge detection threshold based on the noise baseline when the noise baseline is within a first range of values, and a second equation is used to specify the edge detection threshold based on the noise baseline when the noise baseline is within a second range of values. One or more additional equations may also be used when the noise baseline is within one or more further ranges of values, as was explained above.

The noise baseline, and the edged detection threshold that is determined such that it is greater than the noise baseline, can be updated by the external device 109 from time to time. In an embodiment, the noise baseline, and the edged detection threshold that is determined such that it is greater than the noise baseline, is determined by the external device 109 periodically (e.g., once per second, once per N seconds, once per cardiac cycle, once per N cardiac cycles, or other period of time) while the external device 109 is not in an active conductive telemetry session. In other words, the method described above with reference to FIG. 11A can be performed periodically by the external device when the external device 109 is not in an active conductive telemetry session with an LP 102 (or other type of IMD). Additionally, the noise baseline, and the edged detection threshold that is determined such that it is greater than the noise baseline, can be updated by the external device 109 following the end of each frame while the external device 109 is in an active conductive telemetry session with an LP 102 (or other type of IMD). In other words, the method described above with reference to FIG. 11A can be performed following the end of each frame (or following the end of each N frames, i.e., following each of a plurality of frames), before the next frame starts, while the external device 109 is in an active conductive telemetry session with an LP 102 (or other type of IMD).

Referring now to FIG. 11B, step 1106 involves producing edge detections by comparing a sensed signal that is sensed using the sensing vector to the edge detection threshold (determined at the most recent instance of step 1104) to thereby produce a respective one of the edge detections when an amplitude of the sensed signal transitions from being below the edge detection threshold to being above the edge detection threshold. Step 1108 involves decoding a message encoded in the sensed signal based on the edge detections.

Step 1106 can be performed by the edge detection comparator 1008, after the controller 712 controls the potentiometer 1014 (or some other circuit, such as a DAC) to provide the edge detection threshold (most recently determined) to the reference input of the edge detection comparator 1008. The decoding at step 1108 can then be performed by the message decoder 738, which can be implemented by the controller 712, as shown in FIG. 10.

Referring briefly back to FIG. 9B, the dashed line labeled 922 is an example of the edge detection threshold determined at step 1104, and thereafter used at steps 1106 and 1108 to produce edge detections, which are used at step 1110 to decode a message included in the sensed signal based on the edge detections. Still referring to FIG. 9B, in accordance with an embodiment, a "1" bit value is detected (aka decoded) when there are at least a specified number N of edge detections within a temporal window, examples of which are the temporal windows 912, 914, and 916. The specified number N is an integer that can be, for example, 4, but can alternatively be higher or lower, but is at least 2, so as to prevent brief spurious noise from being detected as a "1" bit value. In an embodiment, each temporal window is divided into two or more sub-windows, and a "1" bit value is detected (aka decoded) when there is at least one edge detected in at least two consecutive (or some other number of consecutive) sub-windows. For example, a 30 microsecond temporal window can be divided into up to fifteen 2 microsecond sub-windows, and a "1" bit value is detected (aka decoded) when there is at least one edge detection in two consecutive 2 microsecond sub-windows. Each temporal window can alternatively be separated into more or less than fifteen sub-windows, e.g., into five sub-windows, and a "1" bit value may be detected when there is at least one edge detection in two (or some other specified number of) consecutive sub-windows, depending upon the specific implementation.

In an embodiment, an interrupt is issued in response to a first edge detection within a temporal window (e.g., a 30 microsecond temporal window), and an interrupt blanking period is triggered in response to the first edge detection, wherein the interrupt blanking period has a shorter duration than the temporal window. For example, where the duration of the temporal window is 30 microseconds, the interrupt blanking period can be about 25 microseconds, or more generally in the range of 18 to 26 microseconds, but is not limited thereto. The interrupt that is generated in response to the first edge detection within a temporal window can begin the determination of whether the conductive communication signature for a "1" bit value is detected. Accordingly, during the interrupt blanking period, edge detections are still triggered for the purpose of determining whether the conductive communication signature for a "1" bit value is detected. The interrupt blanking period can timeout, or it can be terminated, e.g., in response to a determination that the first edge detection was likely due to noise, and/or the like. A blanking period timer, that can be implemented in hardware, firmware, and/or software, can be used to keep track of the interrupt blanking period.

Figure 9C:
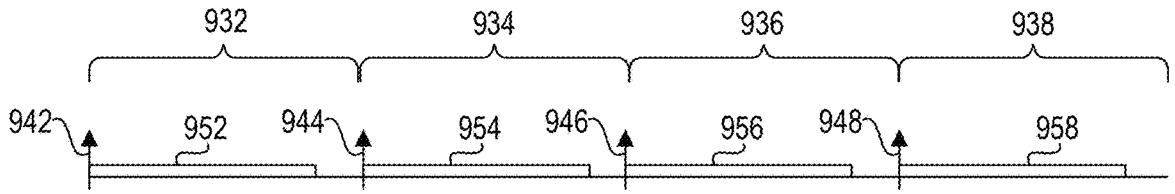
FIG. 9C illustrates interrupt blanking periods that are triggered in response to initial edge detections within temporal windows that are used to determine whether the temporal windows include a bit value "1" or a bit value "0" in accordance with certain embodiments of the present technology.

FIG. 9C illustrates four example temporal windows 932, 934, 936, and 938. The initial or first edge detection within each of the windows 932, 934, 936, and 938 are represented, respectively, by the upward pointing arrows 942, 944, 946, and 948. Additionally, FIG. 9C illustrates an interrupt blanking period 952 triggered by the edge detection represented by the arrow 942, an interrupt blanking period 954 triggered by the edge detection represented by the arrow 944, an interrupt blanking period 956 triggered by the edge detection represented by the arrow 946, and an interrupt blanking period 958 triggered by the edge detection represented by the arrow 948. During each of the interrupt blanking periods bit processing is performed to determine whether a "1" bit value or a "0" bit value is detected within a respective window that includes the interrupt blanking period.

Figure 12A:
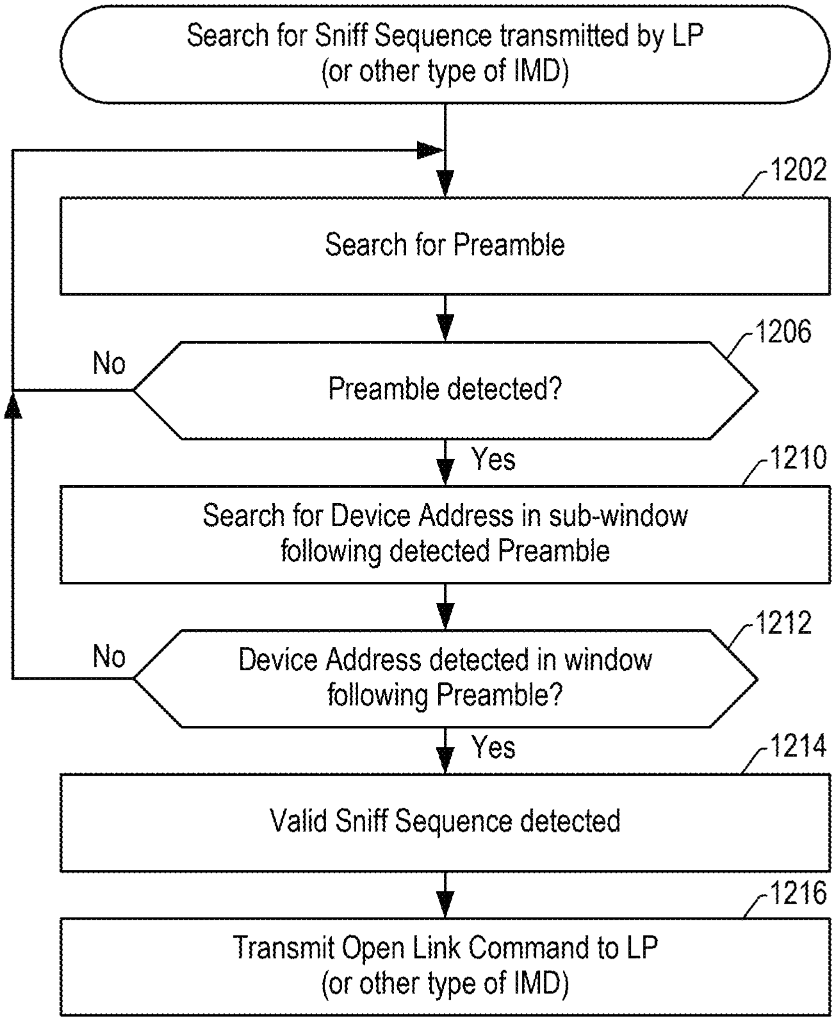
FIG. 12A is a high level flow diagram used to summarize a method according to an embodiment of the present technology for performing a tiered search for an advertisement sequence transmitted by an IMD to enable an external device to detect the presence of the IMD and establish an active conductive telemetry session with the IMD.
Figure 12B:
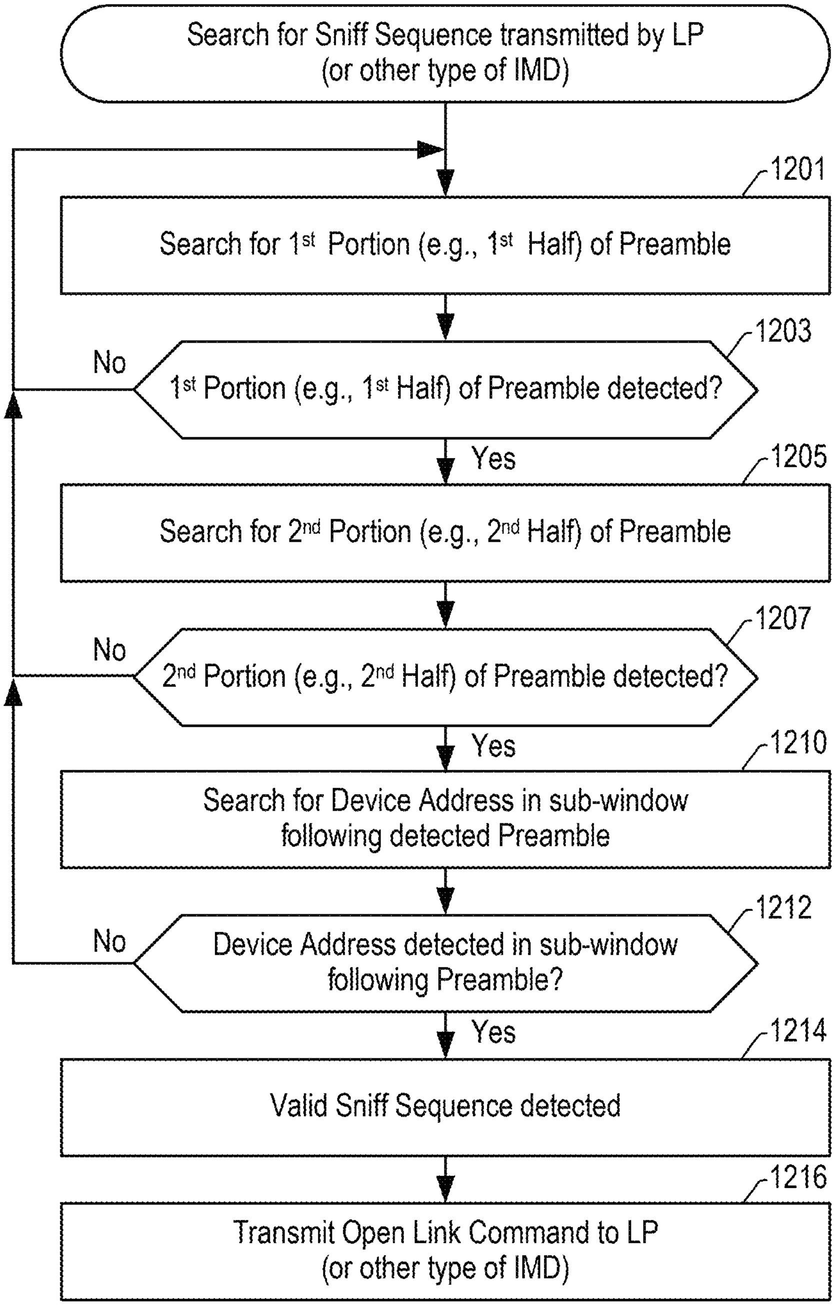
FIG. 12B is a high level flow diagram used to summarize a method according to another embodiment of the present technology for performing a tiered search for an advertisement sequence transmitted by an IMD to enable an external device to detect the presence of the IMD and establish an active conductive telemetry session with the IMD.

When the external device 109 is not in an active conductive telemetry session with an LP 102 (i.e., is in an inactive conductive telemetry session with the LP 102), but wants to enter into an active conductive telemetry session with the LP 102, the external device can monitor for (aka search for) a sniff 802. As noted above, the sniff 802 can also be referred to as a sniff sequence, an advertisement sequence, an advertising sequence, an advertisement notice, or an advertising notice. Referring briefly back to FIG. 8A, in the embodiment shown therein, the sniff 802 includes preamble 810, which is known by the external device 109, followed by a device address 818, which can be any one of one or more device addresses known by the external device 109. The high level flow diagrams of FIGS. 12A and 12B will now be used to describe how the external device 109 can search for a sniff 802, using a tiered search algorithm, in accordance with certain embodiments of the present technology. More specifically, FIG. 12A is used to describe a first embodiment of a tiered search algorithm, and FIG. 12B is used to describe a second embodiment of a tiered search algorithm. Where such algorithms are being used to search for a sniff 802, they can be referred to more specifically as tiered sniff search algorithms. As will be appreciated from the following discussion, such tiered sniff search algorithms can be used to check whether one or more initial portions of a sniff sequence are detected before continued processing of the sniff sequence. This allows for a quick restart of the searching for a valid sniff sequence, while terminating processing of an invalid sniff sequence. The tiered search algorithm may also be used to search for a header 812 of a frame 804.

Referring initially to FIG. 12A, step 1202 involves searching for the preamble, wherein the preamble is a known sequence of bits (e.g., a predetermined byte), and thus, is a known sequence of conductive communication signature.

For example, the preamble can be a 11001101 sequence of bits, but is not limited thereto. At step 1206 there is a determination of whether the preamble was detected. If the answer to the determination at step 1206 is Yes, then flow goes to step 1210. If the answer to the determination at step 1206 is No, then flow returns to step 1202 and the external device 109 restarts searching for the preamble. Assuming each conductive communication signature corresponding to a bit is transmitted within a 30 microsecond window, and the known preamble is eight bits (i.e., a byte) in length, then it would take the external device 109 about 240 microseconds (i.e., 30 microseconds*8=240 microseconds) to collectively perform instances of steps 1202 and 1206. In other words, assuming each conductive communication signature corresponding to a bit is transmitted within a 30 microsecond window, and the known preamble is eight bits (i.e., a byte) in length, then it would take the external device 109 about 240 microseconds to determine whether or not it has received a preamble 810 of a sniff 802. Accordingly, continuing with this example, the external device 109 can repeatedly restart searching for the sniff 802 about every 240 microseconds, until the external device 109 detects the preamble.

Still referring to FIG. 12A, after the preamble of the sniff 802 is detected, the external device 109 searches for one of a plurality of possible device addresses in a further temporal window following the temporal window within which the preamble was detected. At step 1212 there is a determination of whether a valid device address (i.e., one of the plurality of known devices addresses) was detected. If the answer to the determination at step 1212 is Yes, then flow goes to step 1214, at which there is the determination that a valid sniff 802 has been detected. If the answer to the determination at step 1212 is No, then flow returns to step 1202 and the external device 109 restarts searching for the preamble. Assuming each conductive communication signature corresponding to a bit is transmitted within a 30 microsecond window, and each known device address is eight bits (i.e., a byte) in length, then it would take the external device 109 about an additional 240 microseconds to collectively perform instances of steps 1210, 1212. In other words, assuming each conductive communication signature corresponding to a bit is transmitted within a 30 microsecond window, and the known device address is eight bits (i.e., a byte) in length, then it would take the external device 109 about an additional 240 microseconds to determine whether or not it has received a valid device address.

In accordance with an embodiment, assuming the external device 109 wants to start a conductive telemetry session, once a valid sniff sequence is detected by the external device, the external device can transmit an open link command at step 1216, as shown in FIG. 12A. Referring briefly back to FIG. 8B, such an open link command can be included in the segment 824 of the body 822 of a frame 804 that occurs after the valid sniff 802 was detected at an instance of step 1214.

An alternative to the embodiment described above with reference to FIG. 12A will now be described below with reference to FIG. 12B. Referring to FIG. 12B, step 1201 involves searching for a first portion (e.g., a first half) of the preamble, wherein the preamble (and thus, its first portion) is a known sequence of bits (e.g., a predetermined nibble), and thus, is a known sequence of conductive communication signatures. For example, if the preamble is the 11001101 sequence of bits, then the known first half of the preamble is the 1100 sequence of bits. At step 1203 there is a determination of whether the first portion of the preamble was detected. If the answer to the determination at step 1203 is Yes, then flow goes to step 1205. If the answer to the determination at step 1203 is No, then flow returns to step 1201 and the external device 109 restarts searching for the first portion (e.g., first half) of the preamble. Assuming again that each conductive communication signature corresponding to a bit is transmitted within a 30 microsecond window, and the known first portion of the preamble is four bits (i.e., a nibble) in length, then it would take the external device 109 about 120 microseconds (i.e., 30 microseconds*4=120 microseconds) to collectively perform instances of steps 1201 and 1203. In other words, assuming each conductive communication signature corresponding to a bit is transmitted within a 30 microsecond window, and the known first half of the preamble is four bits (i.e., a nibble) in length, then it would take the external device 109 about 120 microseconds to determine whether or not it has received the first portion of the preamble 810 of a sniff 802. Accordingly, continuing with this example, the external device 109 can repeatedly restart searching for the sniff 802 about every 120 microseconds, until the external device 109 detects the preamble, which is half the time than it took in the embodiment described above with reference to FIG. 12A.

Referring briefly back to FIG. 8A, the first portion (e.g., the first half) of the preamble 810 is labeled 814, and the second portion (e.g., the second half) of the preamble is labeled 816. Referring again to FIG. 12B, once the first portion (e.g., first half) 814 of the preamble 810 is detected, and the answer to the determination at step 1207 is Yes, then flow goes to step 1205. Step 1205 involves searching for a second portion (e.g., a second half) of the preamble, which is a known sequence of conductive communication signature. For example, if the preamble is the 11001101 sequence of bits, then the known second half of the preamble is the 1101 sequence of bits. At step 1207 there is a determination of whether the second portion of the preamble was detected. If the answer to the determination at step 1207 is Yes, then flow goes to step 1210. If the answer to the determination at step 1207 is No, then flow returns to step 1201 and the external device 109 restarts searching for the first portion (e.g., first half) of the preamble. Steps 1210, 1212, 1214, and 1216 are the same as in FIG. 12A, and thus, need not be described again.

Once the external device 109 has detected a valid sniff from an LP 102 (or another type of IMD) at an instance of step 1214, the external device 109 can transmit an open link command to the LP 102. Referring briefly back to FIG. 8B, such an open link command is transmitted within a segment 824 of a frame 804, wherein the frame 804 includes both a header 812 and a body 822 and is utilized for conductive communication between an external device (e.g., 109) and an IMD (e.g., an LP 102). Once an open link command is transmitted by the external device 109 to the LP 102 (or other type of IMD) and received and acknowledged by the LP 102, an active conductive telemetry session is established between the external device 109 and the LP 102 (or other type of IMD). In accordance with certain embodiments, during the active telemetry session it is the LP 102 (or other type of IMD) that transmits the header 812, and it is the external device 109 that transmits the command within the segment 824. If marker data (aka cardiac data) is sent within the frame, then it is the LP 102 (or other type of IMD) that transmits the marker data within the segment 826. Depending upon the type of command included within the segment 824, it could either be the external device 109 that transmits the payload data within the segment 828 (e.g., if the command transmitted by the external device 109 was a write type command), or the LP 102 (or other type of IMD) that transmits the payload data within the segment 828 (e.g., if the command transmitted by the external device 109 was a read type command).

The embodiments described with reference to FIGS. 12A and 12B can also be used to search for the header of a frame for the purpose of attempting to generally synchronize or generally lock the timing of the external device 109 to that of the LP 102 (or other type of IMD). Once the external device 109 detects a header 812 of a frame, then it can detect a device address 818 of the frame, and then send a command, receive marker data (aka cardiac event data), and transmit or receive payload data, at appropriate times (i.e., within appropriate temporal windows) using various techniques described above.

Figure 13A:
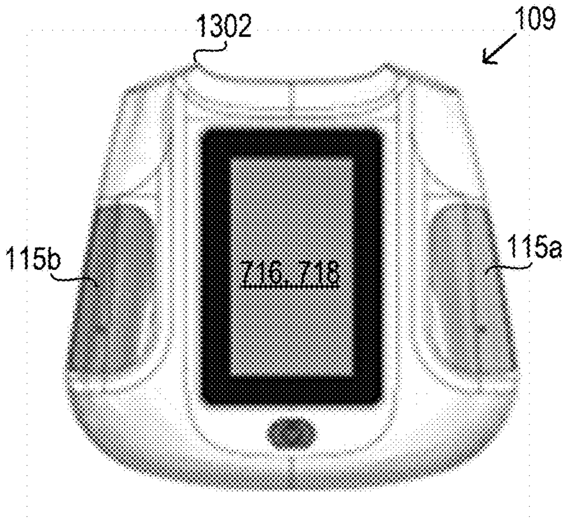
FIGS. 13A, 13B, 13C, and 13D illustrates, respectively, front, back, right side, and left side views of a formfactor of an external device according to an embodiment of the present technology.
Figure 13B:
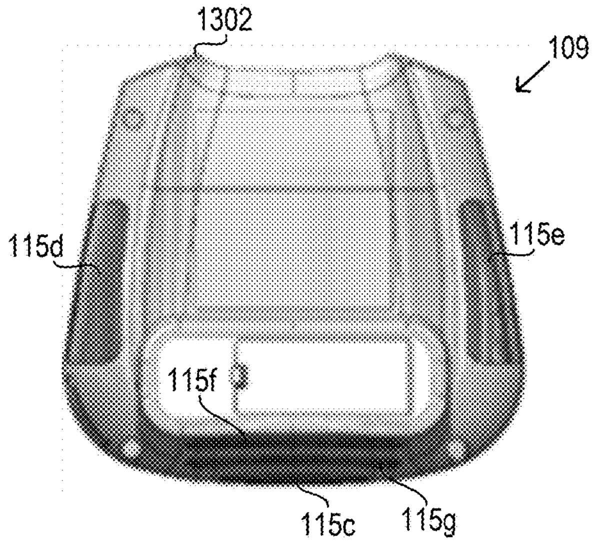
Figure 13C:
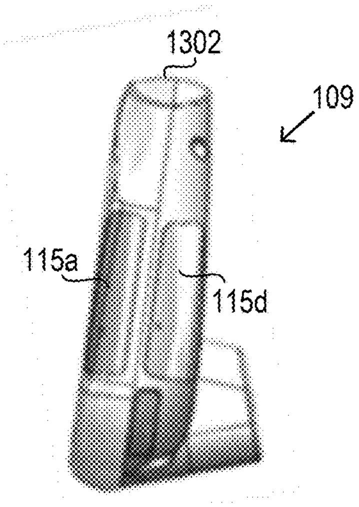
Figure 13D:
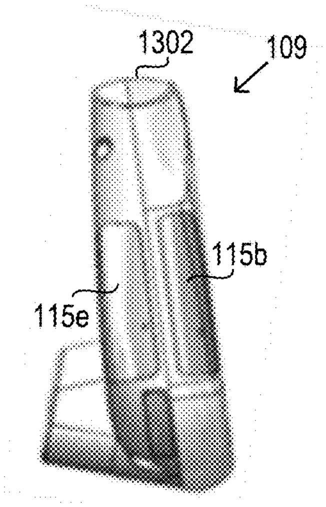

While only three external electrodes 115 are shown in many of the FIGS. described above, the external device 109 (aka, external medical device (EMD)) can include and/or be communicatively coupled to more than three external electrodes 115. For example, in certain embodiments, the external device 109 includes or is communicatively coupled to seven external electrodes 115. In certain such embodiments, the seven external electrodes 115 are attached to the housing of the external device 109 and include a right front electrode, a right back electrode, a left front electrode, a left back electrode, a bottom upper electrode, a bottom middle electrode, and a bottom lower electrode. An example formfactor of such an external device 109 is shown in FIGS. 13A, 13B, 13C, and 13D, which respectively show front, back, right side, and left side views of the external device 109 according to an embodiment. The external device 109 in FIGS. 13A-13D is shown as including a housing 1302 to which are attached a right front electrode 115*a*, a right back electrode 115*d*, a left front electrode 115*b*, a left back electrode 115*e*, a bottom upper electrode 115*c*, a bottom lower electrode 115*f*, and a bottom middle electrode 115*g*. Also shown in FIG. 13A is a display 716, which is a touch-screen type of display, and thus can also provide a user-interface 718, or at least a portion thereof. In certain such embodiments, the external device 109 is configured such that when in use the patient should hold the external device 109 by grasping the right front electrode 115*a* and the right back electrode 115*d* with their right hand, grasping the left front electrode 115*b* and the left back electrode 115*e* with their left hand, and resting the bottom of the external device on their lower torso or a lower extremity (and more specifically, on a body region below the heart, such as their stomach, one of their left or right thighs, or one of their left or right ankles) so that each the bottom upper electrode 115*c*, the bottom lower electrode 115*f*, and the bottom middle electrode 115*g* is simultaneously in contact with the patient's skin of their lower torso/extremity. The right front electrode 115*a*, the left front electrode 115*b*, and the bottom upper electrode 115*c* are used for conductive communication transmission between the external device and one or more IMDs, e.g., one of more LPs. The right back electrode 115*d*, the left back electrode 115*e*, and the bottom lower electrode 115*f* are used for conductive communication reception from one or more IMDs, e.g., one or more LPs. The right back electrode 115*d* and the left back electrode 115*e* are also used to sense a common mode rejection signal, and the bottom middle electrode 115*g* is used to inject the common mode rejection signal into the patient. The right back electrode 115*d* and the left back electrode 115*e* of the external device are also used to sense an electrocardiogram (ECG) signal. The bottom lower electrode 115*f* may additionally, or alternatively, be used to sense the ECG signal and/or to sense the common mode rejection signal, along with one or both of the right back electrode 115*d* and the left back electrode 115*e*. The specific uses of the various electrodes described above can be modified while still being within the scope of the embodiments of the present technology described herein. For example, alternatively the right front electrode 115*a*, the left front electrode 115*b*, and the bottom upper electrode 115*c* can be used by the external device for conductive communication reception from one or more IMDs; and the right back electrode 115*d*, the left back electrode 115*e*, and the bottom lower electrode 115*f* can be used for conductive communication transmission between the external device and one or more IMDs. Other variations are also possible and within the scope of the embodiments described herein.

The right front electrode 115*a* and the right back electrode 115*d* can be referred to herein as a right electrode pair, the left front electrode 115*b* and the left back electrode 115*e* can be referred to herein as a left electrode pair, and the bottom upper electrode 115*c* and the bottom lower electrode 115*f* can be referred to herein as a bottom electrode pair. In accordance with certain embodiments, the external device 109 is configured to test different combinations of its external electrodes 115 to determine which electrode combination (aka electrode vector) provides for the best conductive communication quality, and to thereafter utilize the combination that provides for the best conductive communication quality during a communication session with one or more IMDs, e.g., one or more LPs. For example, a first electrode vector can be between the left and right electrode pairs, a second electrode vector can be between the right and bottom electrode pairs, and a third electrode vector can be between the left and bottom electrode pairs. Continuing with the above example, when the first electrode vector is being tested or otherwise used, the right front electrode 115*a* and the left front electrode 115*b* are used to transmit conductive communication pulses from the external device to one or more IMDs (e.g., one of more LPs), and the right back electrode 115*d* and the left back electrode 115*e* are used for receiving conductive communication pulses from the one or more IMDs. When the second electrode vector is being tested or otherwise used, the right front electrode 115*a* and the bottom upper electrode 115*c* are used to transmit conductive communication pulses from the external device to the one or more IMDs, and the right back electrode 115*d* and the bottom lower electrode 115*f* and used for receiving conductive communication pulses from the one or more IMDs. When the third electrode vector is being tested or otherwise used, the left front electrode 115*b* and the bottom upper electrode 115*c* are used to transmit conductive communication pulses from the external device to one or more IMDs (e.g., one of more LPs), and the left back electrode 115*e* and the bottom lower electrode 115*f* and used for receiving conductive communication pulses from the one or more IMDs. A benefit of there being a right electrode pair, a left electrode pair, and bottom electrode pair (compared to there being just one right electrode, one left electrode, and one bottom electrode) is that while a specific electrode vector is being tested or otherwise used, one subset of the external electrodes (e.g., the right front electrode 115*a* and the left front electrode 115*b*) can be connected by the switches 713 to the conductive communication transmitter 732, while another subset of the external electrodes (e.g., the right back electrode 115*d* and the left back electrode 115*e*) can be connected by the switches 713 to the conductive communication receiver 742. However, in alternative embodiments, there can be a single right electrode, a single left electrode, and a single bottom electrode, in which case while a specific subset of electrodes (e.g., the single right electrode and the single left electrode) is being tested or otherwise used, during a same frame the switches 713 may need to quickly switch between when the specific subset of electrodes is connected to the conductive communication transmitter 732, and when the specific subset of electrodes is connected to the conductive communication receiver 742.

In the above described embodiment, different combinations of six external electrodes can be used by the external device to perform conductive communication with one or more IMDs, wherein the six external electrodes include a right electrode pair, a left electrode pair, and a bottom electrode pair. Accordingly, in the above described embodiment, three electrode pairs (aka first, second, and third electrode pairs) are available to the external device to perform conductive communication with one or more IMDs. Within each of the electrode pairs, one of the electrodes can be used by the external device for transmitting conductive communication signals to IMD(s), and another one of the electrodes can be used by the external device for receiving conductive communication signals from IMD(s). Explained another way, in the above described embodiment, three external electrodes can be used by the external device for transmitting conductive communication signals to IMD(s), and another three external electrodes can be used for receiving conductive communication signals from IMD(s). The combination of external electrodes that the external device is using at any given time to attempt to receive conductive communication signals from IMD(s) can be referred to as a sensing vector. The combination of external electrodes 115 that the external device 109 is using at any given time to transmit conductive communication signals to IMD(s) can be referred to as a transmitting vector. Sensing vectors and transmitting vectors can be referred to generally as conductive communication vectors, or more succinctly as communication vectors.

In accordance with certain embodiments, the example external device 109 described with reference to FIGS. 13A-13D can include one or more ports to which two wrist bands and an ankle band can electrically connected to the external device 109. One of the wrist bands can be configured to be attached to the right wrist of a patient and can include a pair of electrodes that can be used in a same or similar manner as the electrodes 115*a* and 115*d*; the other one of the wrist bands can be configured to be attached to the left wrist of a patient and can include a pair of electrodes that can be used in a same or similar manner as the electrodes 115*b* and 115*e*; and the ankle band can be configured to be attached to either one of the left or right ankles of the patient and can include three electrodes that can be used in the same or similar manners as the electrodes 115*c*, 115*f*, and 115*g*. Other variations are also possible and within the scope of the embodiments described herein. For example, the wrist bands can instead be arm bands, and/or the ankle band can instead be calf band or a thigh band.

In accordance with certain embodiments, the example external device 109 described with reference to FIGS. 13A-13D can include the various circuits and other components described above with reference to FIGS. 7 and 10.

Figure 14:
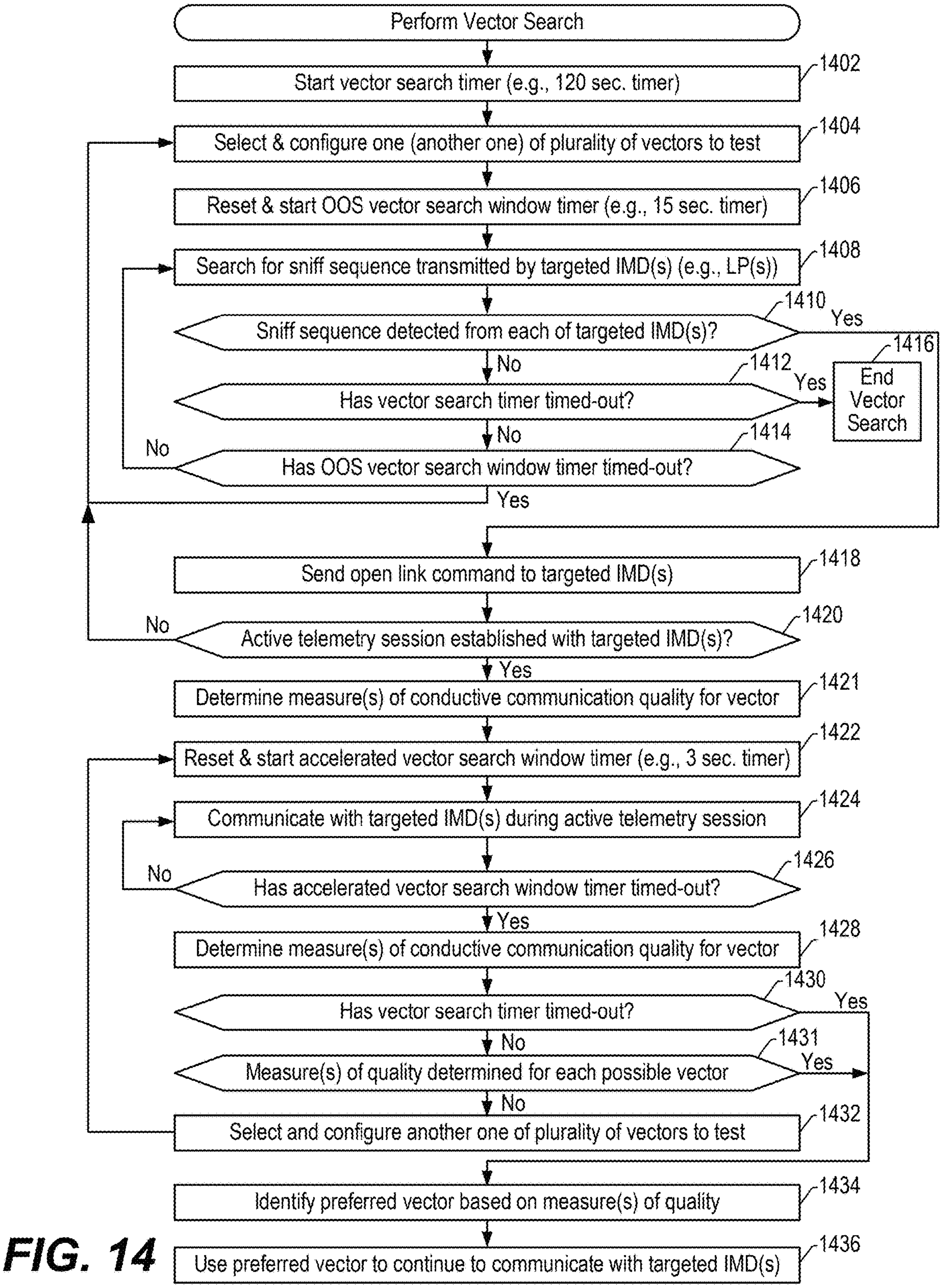
FIG. 14 is a high level flow diagram used to summarize methods, according to certain embodiments of the present technology, for an external device performing a vector search when attempting to establish a conductive communication session with one or more IMDs.

As can be appreciated from the above discussion, when an external device 109 includes or is communicatively coupled to at least three electrodes 115 (e.g., as was described above with reference to FIGS. 6, 7, 10, and 13A-13D), the external device 109 can identify which one of a plurality of the subsets of the electrodes, or more generally, which one of the plurality of possible conductive communication vectors, is a preferred conductive communication vector for communicating with one or more targeted IMD(s). The process used by the external device 109 to identify the preferred conductive communication vector can be referred to herein as a vector search. The high level flow diagram in FIG. 14 will now be used to describe a vector search that can be performed by an external device 109, according to an embodiment of the present invention. Referring to FIG. 14, step 1402 involves starting a vector search timer, which specifies how long the vector search is performed (e.g., 120 seconds) before it either times out and ends, or times out and selects a preferred vector. Depending upon the specific implementation, the vector search timer can be configured to start at zero and count up to a programmed time value (e.g., 120 seconds), or alternatively can be configured to start at the programmed time value (e.g., 120 seconds) and then count down to zero. The other timers mentioned herein can be implemented in similar manners. The vector search timer, and other timers mentioned herein, can be implemented in hardware, firmware, and/or software.

Step 1404 involves selecting one of the communication vectors to test and configuring the external device (e.g., using switches 713), to utilize the selected vector, by connecting electrodes of the selected vector to appropriate circuitry of the external device. For example, this can involve using switches to connect one subset of the external electrodes to the conductive communication transmitter 732, and using switches to connect another subset of the external electrodes to the conductive communication receiver 742. In other words, when one of the plurality of different combinations of the at least three external electrodes is selected as the test vector, a first subset of the at least three external electrodes that is used by the external device to transmit conductive communication pulses to the IMD can differ from a second subset of the at least three external electrodes that is used by the external device to receive conductive communication pulses from the IMD. Alternatively, depending upon implementation, a same subset of the at least three external electrodes that is used by the external device to transmit conductive communication pulses to the IMD may also be used by the external device to receive conductive communication pulses from the IMD. The communication vector selected to test at an instance of step 1404 can also be referred to herein as the test vector.

Step 1406 involves resetting and starting an out-of-session (OOS) vector search window timer that is used to track how long a vector has been used during the vector search, while the external device is not in an active conductive communication session with any IMD. Explained another way, the OOS vector search window timer specifies how long (e.g., 15 seconds) the vector search is performed using the test vector selected and configured at step 1402, while the external device is not in an active conductive communication session with any IMD, before the external device moves onto testing another vector. An active conductive communication session can also be referred to herein as an active conductive telemetry session, or more succinctly as an active telemetry session, or the like.

Step 1408 involves searching for a sniff sequence (aka an advertisement sequence of pulses) transmitted by one or more targeted IMD(s) with which the external device is attempting to communicate. An example of such a sniff sequence was described above with reference to FIG. 8A.

At step 1410 there is a determination of whether the sniff sequence was detected from each of the targeted IMD(s). The sniff sequence can be considered detected from a targeted IMD when the sniff sequence has been successfully received and decoded by the external device. If the answer to the determination at step 1410 is No, then flow goes to step 1412. At step 1412 there is a determination of whether the vector search timer has timed out. If the answer to the determination at step 1412 is No, then flow returns to step 1408 and the external device continues to search for the respective sniff sequence from each of the targeted IMD(s). If the answer to the determination at step 1412 is Yes, then flow goes to step 1416 and the vector search is ended, i.e., it times out. After a vector search is ended at an instance of step 1416, a new vector search can be initiated by the external device at a later time, as controlled by the external device. Returning to step 1410, if the answer to step 1410 is Yes, meaning the sniff sequence(s) was/were detected from each of the targeted IMD(s), then flow goes to 1418. Example details of how the external device can search for and detect the sniff sequence were described above with reference to the flow diagrams of FIGS. 12A and 12B, and thus need not be described again.

At step 1418 the external device 109 sends an open link command to each of the targeted IMD(s). Such an open link command can be part of a frame 804 described above with reference to FIG. 8B. If there are multiple targeted IMDs with which the external device 109 wants to communicate, each with its own device address, then a separate open link command is sent for each of the targeted IMDs. In accordance with certain embodiments, each targeted IMD, in response to successfully receiving an open link command, is configured to send an ACK back to the external device. If the ACK sent by a targeted IMD is successfully received by the external device, then an active conductive telemetry session is established between the external device and the IMD. However, if a targeted IMD does not successfully receive the open link command, or the external device does not successfully receive the ACK sent by the IMD, then an active telemetry session is not established between the external device and the IMD. In accordance with other embodiments, targeted IMD(s) are not configured to send an ACK in response to successfully receiving an open link command, but rather, are configured to respond to an open link command in the same manner as a read type command. More specifically, in such embodiments, a targeted IMD that successfully receives an open link command will include payload data and a third CRC code in the first segment of the body of the frame that included the open link command, and the external device will determine that an active telemetry session is established between the external device and the targeted IMD in response to receiving the payload data and a valid third CRC code. In certain embodiments, whenever a sniff sequence is detected from a targeted IMD, an open link command is sent to that targeted IMD.

At step 1420 there is a determination of whether active telemetry session(s) is/are established between the external device and the targeted IMD(s). If the answer to the determination at step 1420 is No, then flow returns to step 1404, and another vector to test is selected and configured. However, if the answer to the determination at step 1420 is Yes, then flow goes to step 1421, and one or more measures of conductive communication quality are determined (and saved) for the vector that was just tested. Examples of such measures are discussed below, when discussing step 1431. Following step 1421, flow goes to step 1422, which begins an accelerated portion of the vector search. The steps that occur prior to the answer to the determination at step 420 being yes, which occur while an active telemetry session has not yet been established between the external device and the targeted IMD(s), can be referred to as an out-of-session (OOS) portion of vector search. During the OOS portion of the vector search, each of the IMD(s) separately transmits the sniff sequence (e.g., 802) relatively infrequently, e.g., once every N cardiac cycles, where N is at least two (e.g., N=6, 7, 8, or 9, but is not limited thereto). That is why a duration of the OOS vector search window, used to determine how long each vector is to be tested (referred to in steps 1406 and 1414), is relatively long (e.g., 15 seconds). By contrast, when step 1422 is reached, an active telemetry session has already been established between the external device and the targeted IMD(s), during which frames (e.g., 804) are communicated relatively frequently, e.g., anywhere between one and four frames (but not limited thereto) may be communicated per cardiac cycle. Accordingly, while the active telemetry session(s) is/are established between the external device 109 and the targeted IMD(s), each of the test vectors being tested can be tested for a shorter time window (e.g., 3 seconds), compared to when the active telemetry session(s) is/are not established, because there is more frequent communication between the external device 109 and the targeted IMD(s) during the active telemetry session(s) between the external device and the targeted IMD(s), compared to when there is/are not active telemetry session(s) between the external device and the targeted IMD(s). The shorter time window (e.g., 3 seconds) introduced above can be referred to herein as an accelerated vector search window. In accordance with certain embodiments, a duration of the accelerated vector search window is at least one-half of a duration OOS vector search window, but is not limited thereto. In specific embodiments, the duration of the accelerated vector search window is at least one-third of the duration OOS vector search window. In specific embodiments, the duration of the accelerated vector search window is about one-fifth of the duration OOS vector search window, e.g., the OOS vector search window has a duration of 15 seconds, and the accelerated vector search window has a duration of 3 seconds.

At step 1424 the external device communicates with the targeted IMD(s) with which active telemetry session(s) has/have been established, e.g., utilizing the frames 804 described above with reference to FIG. 8B, but not limited thereto. While the external device communicates with the targeted IMD(s), one or more measurements and/or other types of determinations can be made and tracked to thereby enable the external device to determine one or more metric(s) of conductive communication quality achieved between the external device and each of the targeted IMD(s). Where the external device wants to read or write data to or from a targeted IMD during an active telemetry session with the targeted IMD, the external device can include read or write commands within the frames. Where the external device does not want to read or write data to or from a targeted IMD during an active telemetry session with the targeted IMD, the external device can include an open link command or a keep link alive command within the frames, so that the one or more measurements and/or other types of determinations can be made and tracked to enable the external device to determine the one or more metric(s) of conductive communication quality achieved between the external device and each of the targeted IMD(s).

At step 1422, there is a determination of whether the accelerated vector search window (e.g., the 3 second window) has timed-out. If the answer to the determination at step 1426 is No, the flow returns to step 1424 and the external device continues to communicate with the targeted IMD(s). If the answer to the determination at step 1426 is Yes, then flow goes to step 1428.

At step 1428, the external device determines one or more measures of conductive communication signal quality, which can include surrogates thereof. Examples of such measures of conductive communication signal quality (which can include surrogates thereof) which can be determined at each instance of step 1428 (as well as at each instance of step 1421 mentioned above) include: a noise floor associated with the communication vector; a measure of amplitude of at least a portion of a conductive communication signal received by the external device from a targeted IMD using the communication vector; a measure of amplitude of at least a portion of a conductive communication signal received by the targeted IMD from the external device; a magnitude of at least a portion of a conductive communication signal received by the external device from the targeted IMD after rectification and integration thereof; a magnitude of at least a portion of a conductive communication signal received by the targeted IMD from the external device after rectification and integration thereof; a signal-to-noise ratio (SNR) of at least a portion of a conductive communication signal received by the external device from the targeted IMD; a SNR of at least a portion of a conductive communication signal received by the targeted IMD from the external device; a total energy of at least a portion of a conductive communication signal received by the external device from the targeted IMD, after rectification and integration thereof; a total energy of at least a portion of a conductive communication signal received by the targeted IMD from the external device, after rectification and integration thereof; a bit-error-rate (BER) associated with at least a portion of a conductive communication signal received by the external device from the targeted IMD; and a BER associated with at least a portion of a conductive communication signal received by the targeted IMD from the external device. One of the above measures can be used as a score for a test vector, or if multiple ones of the above measures is determined the various measures can be combined into a score for the test vector. The use of additional and/or alternative measures of conductive communication signal quality and/or the surrogates thereof are also possible and within the scope of the embodiments described herein. Some examples of such additional and/or alternative measures of conductive communication signal quality are described further below. More generally, at each instance of step 1428 (as well as at each instance of step 1421), a respective score is determined for a test vector, so that at a later step (i.e., step 1434) scores determined for different test vectors can be compared to one another and used to identify a preferred vector.

Returning to the discussion of FIG. 14, at step 1430, there is a determination of whether the vector search timer (e.g., 120 second timer), which had been started at step 1402, has timed out. If the answer to the determination at step 1430 is No, then flow goes to step 1431. At step 1431 there is a determination of whether measure(s) of conductive communication quality, or more generally a score, has been determined for each of the possible vectors to be tested. If the answer to the determination at step 1431 is No, then flow goes to step 1432.

Step 1432 involves selecting another one of the communication vectors to test and configuring the external device (e.g., using switches 713), to utilize the selected vector, by connecting electrodes of the selected vector to appropriate circuitry of the external device. For example, this can involve using switches to connect another subset of the external electrodes to the conductive communication transmitter 732, and using switches to connect a further subset of the external electrodes to the conductive communication receiver 742. Step 1432 is similar to step 1404 in that another vector is selected for testing, i.e., another test vector is selected. However, step 1432 differs from step 1404 in that step 1432 is performed while active conductive communication session(s) is/are established between the external device and the targeted IMD(s), and step 1404 was performed while active conductive communication session(s) was/were not yet established between the external device and the targeted IMD(s). After step 1432, flow returns to step 1422, so that at the next instance of step 1428 the external device can determine one or more metrics of conductive communication quality for the other vector just tested, and save the metric(s).

Eventually, the answer to the determination at one of steps 1430 or 1431 will be Yes, at which time flow will go to step 1434. At step 1434 the external devices identifies a preferred conductive communication vector, based on the metrics of conductive communication quality that were determined at step 1421 and instances of step 1428 for the various conductive communication vectors that were tested. In accordance with certain embodiments, where there are multiple target IMDs (e.g., multiple LPs) with which the external device 109 wants to communicate, the external device 109 selects as a preferred vector, a vector that can be used to communicate with all of the target IMDs with acceptable quality, if such a vector is available. More generally, at step 1434 the external device selects a preferred vector, based on scores determined at step 1421 and instances of step 1428. Additional details of step 1434, according to certain embodiments of the present technology, are described further below.

At step 1436 the external device uses the preferred vector, identified at step 1434, to continue to communicate with the targeted IMD(s). Eventually, when the external device no longer needs to communicate with the targeted IMD(s), e.g., because it has completed programming and/or interrogating the targeted IMD(s), the external device will send a close link command to the targeted IMD(s), and the active telemetry session(s) will be dropped. The close link command can be sent to all targeted IMD(s) or can be selectively sent to one or more IMD(s) without changing the existing active conductive session with one or more other IMD(s).

The external device 109 can save (e.g., in memory or a register of, or accessible by, its controller 712) information about the vector that had the best score and was identified as the preferred vector at step 1434, and was selected to use for continued communication at step 1436, so that the next time the external device performs a new vector search (when not in an active telemetry session) the external device can start its search using the most recently identified preferred vector. This should increase a probability that the next time a vector search is started by the external device 109, that the sniff sequence(s) will be quickly detected at an instance of step 1410, since it will often be the case that the preferred vector for a new telemetry session will be the same as the preferred vector for the previous telemetry session.

When discussing step 1428 above, it was noted that the use of additional and/or alternative measures of conductive communication signal quality are also possible and within the scope of the embodiments described herein. Such additional and/or alternative measures of conductive communication signal quality, according to certain embodiments of the present technology, will now be described.

Referring back to FIG. 9B, assume that the conductive communication signature 902 shown therein, or a similar signature, is what used to represent a “1” bit value within a temporal window (e.g., 912, or 914), and thus, the signature

902 can be referred to as a bit 1 signature. In accordance with certain embodiments, each time a bit 1 signature is received by the external device from a targeted IMD, the external device produces multiple (e.g., five) samples of the bit 1 signature using an ADC (e.g., the ADC 1010 in FIG. 10), and uses the samples to produce a score indicative of conductive communication quality. Referring back to FIG. 8B, also assume that each header (e.g., 812) of a frame (e.g., 804) includes the known preamble (e.g., 810) and one of the plurality of known device addresses (e.g., 818). Also assume that the preamble is one byte, and each of the device addresses is one byte, in which case each header (e.g., 812) of a frame (e.g., 804) includes two bytes.

In accordance with certain embodiments, for each frame (e.g., 804) that is received by the external device 109 from a targeted IMD using a specific test vector, during an active telemetry session with the targeted IMD, the external device determines a score, and over time determines a running average of the scores for the specific test vector. If there are two targeted IMDs, a separate respective score is determined for each targeted IMD. If one vector provides that highest score for each targeted IMD, then that vector will be identified as the preferred vector at step 1434. However, if a first vector provides the highest score for a first targeted IMD but not for a second targeted IMD, and a second vector provides the highest score for the second targeted IMD but not for the first targeted IMD, then there are various options for identifying the preferred vector. For example, in one embodiment, the vector that provides for the highest average of the scores for the multiple targeted IMDs can be identified as the preferred vector, so long as each score is at least as a high as a minimal acceptable score. In another embodiment, the vector used to initially establish active telemetry sessions with all targeted IMDs, for which the score was determined at step 1421, is used as the gold standard by which to compare scores for all of the vectors tested, and the only way one of the other vectors is selected as the preferred vector is if one of the other vectors provides for higher scores for each of the targeted IMDs. In still another embodiment, the vector used to initially establish active telemetry sessions with all targeted IMDs, for which the score was determined at step 1421 is again used as the gold standard by which to compare scores for all of the vectors tested, and another vector may be selected as the preferred vector if there is a significant increase in the score (e.g., beyond some specified percentage) corresponding one of the targeted IMDs while there was only some minimal reduction in the score (e.g., less than some specified further percentage) corresponding to another one of the targeted IMDs. Other variations are also possible and within the scope of the embodiments described herein.

In accordance with certain embodiments, in order for a tested vector to be considered as a candidate for being selected as the preferred vector (at an instance of step 1434 described above), the tested vector must satisfy certain specified criteria. Such criteria can include, for example: at least a threshold number of valid headers (i.e., valid preambles plus valid device addresses) were received by the external device from each of the targeted IMDs using the test vector; at least a threshold number of valid CRCs were determined for each of one or more segments of frames (e.g., segments 824, 826 and/or 828 of frames 804, discussed above with reference to FIG. 8B) communicated using the test vector; and/or at least a threshold number of ACKs were received from the targeted IMDs in response to write commands being sent to the targeted IMDs. These are just a few examples, which are not intended to be all encompassing. In such embodiments, if a tested vector does not satisfy the specified criteria then the tested vector cannot be selected as the preferred vector.

As was described above with reference to FIG. 8A, each advertisement sequence (e.g., 802), which can also be referred to as a sniff sequence or sniff, includes a known preamble (e.g., 810) and one of a plurality of known device addresses (e.g., 818). Similarly, each header (e.g., 812) of a frame (e.g., 804) includes the known preamble (e.g., 810) and one of the plurality of known device addresses (e.g., 818). As was also described above, in certain embodiments the preamble is one byte, and each of the device addresses is one byte, in which case each sniff is two bytes, and similarly each header of each frame is two bytes. However, embodiments of the present technology are not limited to such lengths.

Each bit in a sniff 802 and each bit in a frame 804 (including a header 812 of the frame 810) is a binary bit that can have a "1" bit value, or a "0" bit value. Since the preamble is a known sequence of bits, all of the preambles will have a same number of bits having a "1" bit value, and a same number of bits having a "0" bit value. For example, all preambles can have four bits having a "1" bit value and four bits having a "0" bit value. Alternatively, all preambles can have five bits having a "1" bit value and three bits having a "0" bit value. These are just two examples, which are not intended to be all encompassing.

In certain embodiments, the score determined for a test vector used to receive a sniff from an IMD is based measurements of bits of a certain value (e.g., a "1" bit value) within the sniff. Since a device address portion 818 of a sniff 802 (and a device address portion 818 of a header 812 of a frame 810) can be one of a plurality of different device addresses, it would be possible that different device addresses can have different numbers (i.e., quantities) of bits having a "1" bit value, and different numbers of bits having a "0" bit value. If that were the case, a vector search described herein can be inadvertently biased by the address of an IMD, where scoring during the vector search relates to how many and how well "1" bit values are detected. In order to avoid such an inadvertent bias, in accordance with certain embodiments of the present technology, the different device addresses are selected such that while they each have a different sequence of "1" and "O" bit values (so that each device address is unique), they all have the same number (i.e., quantity) of "1" bit values, and the same number of "0" bit values. For example, all of the different device addresses can have four bits having a "1" bit value and four bits having a "0" bit value. Alternatively, all of device addresses can have five bits having a "1" bit value and three bits having a "0" bit value. These are just two examples, which are not intended to be all encompassing.

Referring briefly back to FIG. 9B, illustrates therein, as explained above, is a portion of a conductive communication signal including two instances of a conductive communication signature 904 used to represent a "1" bit value, and one instance of a conductive communication signature 902 to be used to represent a "0" bit value, after the conductive communication signal has been transmitted by an IMD through patient tissue and received by an external device and amplified and filtered by the external device. Also shown in FIG. 9B was an example of the edge detection threshold 922. As explained above, in accordance with an embodiment, a "1" bit value is detected (aka decoded) when there are at least a specified number N of edge detections within a temporal window, examples of which are the temporal windows 912, 914, and 916 in FIG. 9B. The specified number N is in integer that can be, for example, 4, but can alternatively be higher or lower, but is at least 2, so at to prevent brief spurious noise from being detected as a "1" bit value. In an embodiment, each temporal window is divided into two or more sub-windows, and a "1" bit value is detected (aka decoded) when there is at least one edge detected in at least two consecutive (or some other number of consecutive) sub-windows.

Referring now briefly back to FIG. 10, outputs of an amplitude detector 1010 are provided to a signal strength determination module 1018, and can be used by the signal strength determination module 1018 to monitor conductive communication quality, which as noted above, can be used to determine scores that are used to identify and select a preferred combination of external electrodes 115 to use for performing conductive communication with one or more targeted IMDs. More generally, outputs of the signal strength determination module 1018 can be used to determine a respective score for a test vector, so that scores determined for different test vectors can be compared to one another and used to identify a preferred vector.

In accordance with certain embodiments, for each "1" bit in the header of a frame received using a specific external electrode vector, during a vector search, a plurality of M (e.g., M=5) amplitude values are produced using the amplitude detector 1010 (e.g., an ADC), e.g., by sampling an accumulated voltage stored on a capacitor that integrates a charge of a "1" bit over the period of the "1" bit. Accordingly, where M=5, for each "1" bit in the header there is a 1st amplitude value, a 2nd amplitude value, a 3rd amplitude value, a 4th amplitude value, and a 5th amplitude value. In an embodiment, the 1st amplitude value can be determined by the ADC at a specified delay (e.g., 5 microseconds) following an initial edge detection (i.e., following an initial crossing of the edge detection threshold 922), and each of the $2^{nd}$, $3^{rd}$, $4^{th}$, and $5^{th}$ amplitude values can be determined at fixed delays thereafter, e.g., spaced about 2 microseconds apart.

Assuming that there are eight "1" bits in the header of the frame, then this would results in eight sets of M (e.g., M=5) amplitude values. For example, a 1st set of 5 amplitude values would include a respective 1st amplitude value, a 2nd amplitude value, a 3rd amplitude value, a 4th amplitude value, and a 5th amplitude value; a 2nd set of 5 amplitude values would include a respective 1st amplitude value, a 2nd amplitude value, a 3rd amplitude value, a 4th amplitude value, and a 5th amplitude value; . . . an 8th set of 5 amplitude values would include a respective 1st amplitude value, a 2nd amplitude value, a 3rd amplitude value, a 4th amplitude value, and a 5th amplitude value. In an embodiment, the $1^{st}$ amplitude values each of the 8 sets are summed to produce a 1st amplitudes score, the $2^{nd}$ amplitude values of each of the 8 sets are summed to produce a $2^{nd}$ amplitudes score, the $3^{rd}$ amplitude values of each of the 8 sets are summed to produce a $3^{rd}$ amplitudes score, the $4^{th}$ amplitude values of each of the 8 sets are summed to produce a $4^{th}$ amplitudes score, and the $5^{th}$ amplitude values of each of the 8 sets are summed to produce a $5^{th}$ amplitudes score. The $1^{st}$, $2^{nd}$, $3^{rd}$, $4^{th}$, and $5^{th}$ amplitudes scores determined for a tested vector can then be average (or added) to produce the bit 1 score for that tested vector, which can be compared to similarly determined scores determined for other tested vectors in order to identify the preferred vector at an instance of step 1434. Other variations are also possible and within the scope of the embodiments described herein.

In accordance with an embodiment, for each frame that is conductively communicated using a specific electrode vector that is tested during a vector search, a combined bit 1 score for the vector can be determined, and it is that score that is compared to similar scores determined for other vectors that are also tested during the vector search, for the purpose of determining which of the tested vectors is the preferred electrode vector to use for further conductive communication within one or more targeted IMDs. For example, assume there are four frames communicated per cardiac cycle (within its refractory period), such that four frames are communicated during three consecutive cardiac cycles using the same specific electrode vector, then that means that there would be twelve bit 1 scores for the specific electrode vector. Those twelve (or other number) of bit 1 scores can be averaged (or added) to produce a combined bit 1 score for the specific electrode vector, which is saved and then used in a comparison to other test vectors that are tested during the vector search, for the purpose of determining which of the tested vectors is the preferred electrode vector to use for further conductive communication within one or more targeted IMDs. The bit 1 scores described above, and the combined bit 1 score described above, are examples of a score that is indicative of how well a certain type of bit (in this example, a "1" bit) is conductively communicated using a specific electrode vector. Rather than, or in addition to determining bit 1 scores, it would also be possible to determine bit 0 scores, which can alternatively or additionally be used to for determining which of the tested vectors is the preferred electrode vector to use for conductive communication within one or more targeted IMDs.

The respective score, determined for each of the plurality of different test vectors, can alternatively, or additionally, be based on various other factors, such as how many valid frame headers were conductively communicated using the test vector, how many valid frame segments were conductively communicated using the test vector, and/or how many write acknowledgements were conductively communicated using the test vector. These are just a few examples, which are not intended to be all encompassing.

An external device (e.g., 109) that implements an embodiment involving determining an edge detection threshold based on a noise baseline such that the edge detection threshold is above the noise baseline, as was described above with reference to FIGS. 11A and 11B, can optionally also be used to implement one or more other embodiments described herein, such as an embodiment involving a tiered search for an advertisement sequence transmitted by an IMD, as was described above with reference to FIGS. 12A and 12B. Such an external device (e.g., 109) can additionally or alternatively also be used to implement an embodiment involving performing a vector search during one or more out of session (OOS) vector search windows when attempting to establish a conductive communication session with one or more IMDs, and performing a vector search during one or more accelerated search windows following an active telemetry session being established with one or more IMDs, as was described in more detail above with reference to FIG. 14. Such an external device (e.g., 109) can additionally or alternatively also be used to implement an embodiment where first, second, and third segments of a frame include respective first, second, and third CRC codes, as was described in more detail above with reference to FIGS. 8B and 8C.

An external device (e.g., 109) that implements an embodiment involving a tiered search for an advertisement sequence transmitted by an IMD, as was described above with reference to FIGS. 12A and 12B, can optionally also be used to implement one or more other embodiments described herein, such an embodiment involving performing a vector search during one or more OOS vector search windows when attempting to establish a conductive communication session with one or more IMDs, and performing a vector search during one or more accelerated search windows following an active telemetry session being established with one or more IMDs, as was described in more detail above with reference to FIG. 14. Such an external device (e.g., 109) can additionally or alternatively also be used to implement an embodiment where first, second, and third segments of a frame include respective first, second, and third CRC codes, as was described in more detail above with reference to FIGS. 8B and 8C. Such an external device (e.g., 109) can additionally or alternatively also be used to implement an embodiment involving determining an edge detection threshold based on a noise baseline such that the edge detection threshold is above the noise baseline, as was described above with reference to FIGS. 11A and 11B An external device (e.g., 109) that implements an embodiment involving performing a vector search during one or more OOS vector search windows when attempting to establish a conductive communication session with one or more IMDs, and performing a vector search during one or more accelerated search windows following an active telemetry session being established with one or more IMDs, as was described in more detail above with reference to FIG. 14, can optionally also be used to implement one or more other embodiments described herein, such as an embodiment where a tiered search for an advertisement sequence transmitted by an IMD, as was described above with reference to FIGS. 12A and 12B. Such an external device (e.g., 109) can additionally or alternatively also be used to implement an embodiment involving determining an edge detection threshold based on a noise baseline such that the edge detection threshold is above the noise baseline, as was described above with reference to FIGS. 11A and 11B. Such an external device (e.g., 109) can additionally or alternatively also be used to implement an embodiment where first, second, and third segments of a frame include respective first, second, and third CRC codes, as was described in more detail above with reference to FIGS. 8B and 8C.

An external device (e.g., 109) that implements an embodiment involving determining an edge detection threshold based on a noise baseline such that the edge detection threshold is above the noise baseline, as described above with reference to FIGS. 11A and 11B, can optionally also be used to implement an embodiment where first, second, and third segments of a frame include respective first, second, and third CRC codes, as was described in more detail above with reference to FIGS. 8B and 8C. Such an external device can additionally or alternatively also be used to implement a tiered search for an advertisement sequence transmitted by an IMD, as was described above with reference to FIGS. 12A and 12B. Such an external device (e.g., 109) can additionally or alternatively also be used to implement an embodiment where a vector search is performed during one or more OOS vector search windows when attempting to establish a conductive communication session with one or more IMDs, and/or during one or more accelerated search windows following an active telemetry session being established with one or more IMDs, as was described in more detail above with reference to FIG. 14. Such an external device (e.g., 109) can additionally or alternatively also be used to implement an embodiment involving a tiered search for an advertisement sequence transmitted by an IMD, as was described above with reference to FIGS. 12A and 12B.

An external device (e.g., 109) that implements an embodiment involving determining an edge detection threshold based on a noise baseline such that the edge detection threshold is above the noise baseline, as described above with reference to FIGS. 11A and 11B, can optionally also be used to implement an embodiment involving performing a vector search during one or more OOS vector search windows when attempting to establish a conductive communication session with one or more IMDs, and performing a vector search during one or more accelerated search windows following an active telemetry session being established with one or more IMDs, as was described in more detail above with reference to FIG. 14. Such an external device (e.g., 109) can additionally or alternatively also be used to implement an embodiment involving a tiered search for an advertisement sequence transmitted by an IMD, as was described above with reference to FIGS. 12A and 12B. Such an external device (e.g., 109) can additionally or alternatively also be used to implement an embodiment where first, second, and third segments of a frame include respective first, second, and third CRC codes, as was described in more detail above with reference to FIGS. 8B and 8C.

An embodiment relating to determining an edge detection threshold above a noise baseline, as described above with reference to FIGS. 11A and 11B, can optionally be used in combination with an embodiment involving performing a vector search during one or more OOS vector search windows when attempting to establish a conductive communication session with one or more IMDs, and performing a vector search during one or more accelerated search windows following an active telemetry session being established with one or more IMDs, as was described in more detail above with reference to FIG. 14. A specific example of how such embodiments can be used together in combination is shown in the flow diagram of FIG. 15. Steps in FIG. 15 that are the same or similar to those already described above with reference to FIGS. 11A, 11B, and 14 are numbered the same or similar, and need not be described again in detail.

Figure 15:
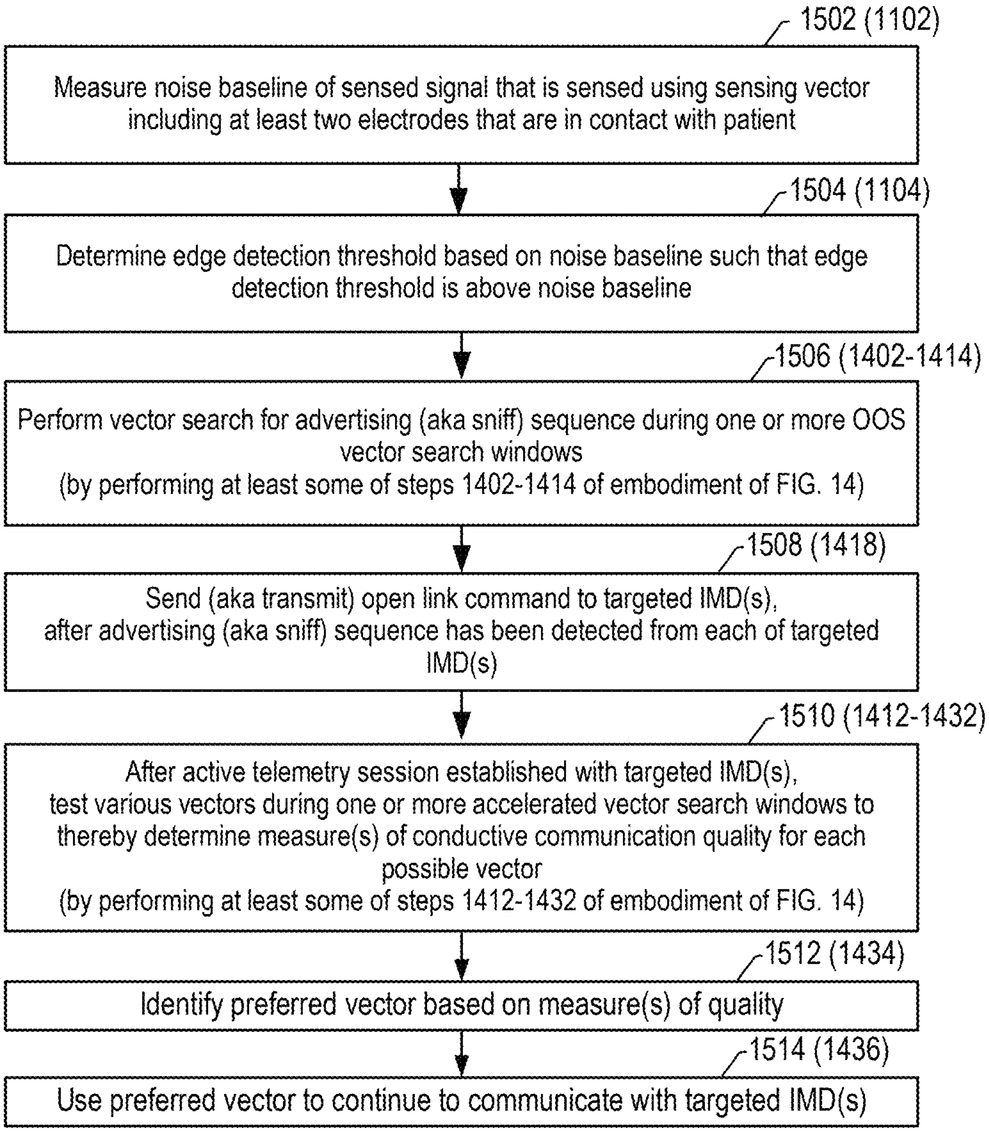
FIG. 15 is a high level flow diagram used to summarize how various embodiments of the present technology can optionally be used in combination with one another.

Referring to FIG. 15, step 1502 (which is the same or similar to step 1102 in FIG. 11) involves an external device (e.g., 109) measuring a noise baseline of a sensed signal that is sensed using a sensing vector including at least two electrodes (e.g., 115) that are in contact with a patient, and step 1504 (which is the same or similar to step 1104 in FIG. 11) involves the external device determining an edge detection threshold based on the noise baseline, measured at step 1102, such that the edge detection threshold is above the noise baseline. In certain embodiments, steps 1502 and 1504 are performed by the external device while it is not in an active conductive telemetry session with an IMD (e.g., an LP 102). Still referring to FIG. 15, step 1506 involves performing a vector search for an advertising (aka sniff) sequence during one or more OOS vector search windows, e.g., by performing steps 1402-1414 of FIG. 14, or a subset thereof. As part of performing the search for the advertising (aka sniff) sequence during an OOS search window, the external device compares a sensed signal (sensed using a sensing vector) to the edged detection threshold determined at step 1104 (the same or similar to what is done in step 1106 in FIG. 11B). Additionally, while attempting to establish an active conductive telemetry session with an IMD (e.g., an LP 102), the external device produces edge detections when an amplitude of the sensed signal transitions from being below the edge detection threshold to above the edge detection threshold (which is the same or similar to what is done in step 1108 in FIG. 11B). At step 1508, after an active telemetry session has been established with the targeted IMD(s), various vectors are tested during one or more accelerated search windows to thereby determine measure (s) of conductive communication quality for each tested vector. Step 1512 (which is the same or similar to step 1434 in FIG. 14) involves the external devices identifying a preferred conductive communication vector, based on the metrics of conductive communication quality that were determined at step 1510. Step 1514 (which is the same or similar to step 1436 in FIG. 14) involves the external device using the preferred vector to continue to communicate with the targeted IMD(s). Additional details of steps 1512 and 1514, according to certain embodiments of the present technology, can be appreciated from the above discussions of steps 1434 and 1436, and thus, need not be repeated.

In certain embodiments, the searching for the advertising (aka sniff) sequence at step 1506 can be implemented by performing a tiered search for the advertising (aka sniff) sequence (using an embodiment of FIG. 12A or 12B), which can include comparing a sensed signal (sensed using the sensing vector) to the edged detection threshold determined at step 1104 (which is the same or similar to what is done in step 1106 in FIG. 11B), producing edge detections when an amplitude of the sensed signal transitions from being below the edge detection threshold to above the edge detection threshold (which is the same or similar to what is done in step 1108 in FIG. 11B), and decoding a message in the sensed signal based on the edge detections (as was done in step 1110 in FIG. 11B) to detect a valid advertising (aka sniff) sequence (which is the same or similar to what is done in step 1214 in FIG. 12B).

In certain embodiments, after the preferred vector is identified and used to communicate with targeted IMD(s), the frames that are used to perform conductive communication between the external device and the targeted IMD(s) can include respective first, second, and third CRC codes, as was described in more detail above with reference to FIGS. 8B and 8C.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in the various flow diagrams. It would also be possible to just perform a subset of the steps shown in the various flow diagrams. For another example, it is possible to change the boundaries of some of the block diagrams.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112 (f), unless and until such claim limitations expressly use the phrase "means for" followed by a statement of function void of further structure.

What is claimed is:

1. A method for use by an external device that is configured to communicate with an implantable medical device (IMD) implanted within a patient using conductive communication, wherein the external device includes or is communicatively coupled to at least three external electrodes that are in contact with the patient, the method comprising:

while the external device is not in an active conductive communication session with the IMD, selecting one of a plurality of different combinations of the at least three external electrodes as a test vector, and during an out-of-session (OOS) search window having a first duration using the test vector to search for an advertisement sequence transmitted by the IMD;

if the advertisement sequence is not detected using the test vector during the OOS search window, selecting and using another one of the plurality of different combinations of the at least three external electrodes as the test vector to search for the advertisement sequence during another instance of the OOS search window having the first duration;

in response to detecting the advertisement sequence from the IMD, establishing an active conductive communication session with the IMD using the test vector that was used to detect the advertisement sequence and determining a respective score for the test vector; and while the active conductive communication session is established with the IMD, using each of other ones of the plurality of different combinations of the at least three external electrodes as the test vector to perform conductive communication with the IMD during an accelerated search window having a second duration that is shorter than the first duration, and determining a respective score for each of the other ones of the plurality of different combinations of the at least three external electrodes used as the test vector during different instances of the accelerated search window;

selecting as a preferred vector, based on the scores, one of the plurality of different combinations of the at least three external electrodes used as the test vector; and performing further conductive communication with the IMD using the preferred vector.

2. The method of claim 1, wherein the second duration of the accelerated search window is at least half of the first duration of the OOS search window.

3. The method of claim 1, wherein when one of the plurality of different combinations of the at least three external electrodes is selected as the test vector, a first subset of the at least three external electrodes that is used by the external device to transmit conductive communication pulses to the IMD differs from a second subset of the at least three external electrodes that is used by the external device to receive conductive communication pulses from the IMD.

4. The method of claim 1, wherein when one of the plurality of different combinations of the at least three external electrodes is selected as the test vector, a same subset of the at least three external electrodes that is used by the external device to transmit conductive communication pulses to the IMD is also used by the external device to receive conductive communication pulses from the IMD.

5. The method of claim 1, further comprising:

a next time the external device is not in an active conductive communication session with the IMD, and the external device attempts to communicate with the IMD, the external device using the preferred vector as an initial combination of the at least three external electrodes to use as the test vector to search for the advertisement sequence during another instance of the OOS search window.

6. The method of claim 1, wherein the respective score, determined for each of the plurality of different combinations of the at least three external electrodes used as the test vector, comprises or is based at least in part on a bit score indicative of how well a certain type of bit is conductively communicated using the test vector.

7. The method of claim 1, wherein the respective score, determined for each of the plurality of different combinations of the at least three external electrodes, is based at least in part on one or more of the following:

how many valid frame headers were conductively communicated using the test vector;

how many valid frame segments were conductively communicated using the test vector; or how many write acknowledgements were conductively communicated using the test vector.

8. The method of claim 1, wherein a said test vector must satisfy predetermined criteria to be eligible for being selected as the preferred vector.

9. An external device configured to communicate with an implantable medical device (IMD) that is implanted in a patient, the external device comprising:

at least three external electrodes configured to be placed in contact with skin of the patient within which the IMD is implanted;

a conductive communication receiver;

a conductive communication transmitter;

a plurality of switches;

a controller communicatively coupled to the conductive communication receiver, the conductive communication transmitter, and the switches;

the controller configured to control the switches to select one of a plurality of different combinations of the at least three external electrodes as a test vector while the external device is not in an active conductive communication session with the IMD, and use the test vector to search for an advertisement sequence transmitted by the IMD during an out-of-session (OOS) search window having a first duration;

if the advertisement sequence is not detected using the test vector during the OOS search window, control the switches to select and use another one of the plurality of different combinations of the at least three external electrodes as the test vector to search for the advertisement sequence during another instance of the OOS search window having the first duration;

in response the advertisement sequence being detected from the IMD, establish an active conductive communication session with the IMD using the test vector that was used to detect the advertisement sequence and determine a respective score for the test vector; and while the active conductive communication session is established with the IMD, control the switches to use each of other ones of the plurality of the different combinations of the at least three external electrodes as the test vector to perform conductive communication with the IMD during an accelerated search window having a second duration that is shorter than the first duration, and determine a respective score for each of the other ones of the plurality of different combinations of the at least three external electrodes used as the test vector during different instances of the accelerated search window;

select as a preferred vector, based on the scores, one of the plurality of different combinations of the at least three external electrodes used as the test vector; and perform further conductive communication with the IMD using the preferred vector.

10. The external device of claim 9, wherein the respective score, determined by the controller for each of the plurality of different combinations of the at least three external electrodes used as the test vector, comprises or is based at least in part on a bit score indicative of how well a certain type of bit is conductively communicated using the test vector.

11. A method for use by an external device that is configured to communicate with each of a plurality of implantable medical devices (IMDs) implanted within a patient using conductive communication, wherein the external device includes or is communicatively coupled to at least three external electrodes that are in contact with the patient, and wherein each of the IMDs is configured to transmit a different one of a plurality of advertisement sequences, the method comprising:

while the external device is not in an active conductive communication session with the IMDs, selecting one of a plurality of different combinations of the at least three external electrodes as a test vector, and during an out-of-session (OOS) search window having a first duration using the test vector to search for advertisement sequences transmitted by the IMDs;

if the advertisement sequences transmitted by the IMDs are not detected using the test vector during the OOS search window, selecting and using another one of the plurality of different combinations of the at least three external electrodes as the test vector to search for the advertisement sequences during another instance of the OOS search window having the first duration;

in response to detecting the advertisement sequences transmitted by the IMDs, establishing active conductive communication sessions with the IMDs using the test vector that was used to detect the advertisement sequences and determining for the test vector a separate respective score for each of the IMDs; and while the active conductive communication sessions are established with the IMDs, using each of other ones of the plurality of different combinations of the at least three external electrodes as the test vector to perform conductive communication with the IMDs during an accelerated search window having a second duration that is shorter than the first duration, and determining for each of the other ones of the plurality of different combinations of the at least three external electrodes used as the test vector during different instances of the accelerated search window a separate respective score for each of the IMDs;

selecting as a preferred vector, based on the scores, one of the plurality of different combinations of the at least three external electrodes used as the test vector; and performing further conductive communication with the IMDs using the preferred vector.

12. The method of claim 11, wherein the second duration of the accelerated search window is at least half of the first duration of the OOS search window.

13. The method of claim 11, wherein when one of the plurality of different combinations of the at least three external electrodes is selected as the test vector, a first subset of the at least three external electrodes that is used by the external device to transmit conductive communication pulses to the IMDs differs from a second subset of the at least three external electrodes that is used by the external device to receive conductive communication pulses from the IMDs.

14. The method of claim 11, wherein when one of the plurality of different combinations of the at least three external electrodes is selected as the test vector, a same subset of the at least three external electrodes that is used by the external device to transmit conductive communication pulses to the IMDs is also used by the external device to receive conductive communication pulses from the IMDs.

15. The method of claim 11, further comprising:

a next time the external device is not in an active conductive communication session with the IMDs, and the external device attempts to communicate with the IMDs, the external device using the preferred vector as an initial combination of the at least three external electrodes to use as the test vector to search for the advertisement sequences during another instance of the OOS.

16. The method of claim 11, wherein the respective score, determined for each of the IMDs for each of the plurality of different combinations of the at least three external electrodes used as the test vector, comprises or is based at least in part on a bit score indicative of how well a certain type of bit is conductively communicated using the test vector.

17. The method of claim 11, wherein the respective score, determined for each of the IMDs for each of the plurality of different combinations of the at least three external electrodes used as the test vector, is based at least in part on one or more of the following:

how many valid frame headers were conductively communicated using the test vector;

how many valid frame segments were conductively communicated using the test vector; or how many write acknowledgements were conductively communicated using the test vector.

18. The method of claim 11, wherein a said test vector must satisfy predetermined criteria to be eligible for being selected as the preferred vector.

19. An external device configured to communicate with a plurality of implantable medical devices (IMDs) implanted in a patient, wherein each of the IMDs is configured to transmit a different one of a plurality of advertisement sequences, the external device comprising:

at least three external electrodes configured to be placed in contact with skin of the patient within which the IMD is implanted;

a conductive communication receiver;

a conductive communication transmitter;

a plurality of switches;

a controller communicatively coupled to the conductive communication receiver, the conductive communication transmitter, and the switches;

the controller configured to control the switches to select one of a plurality of different combinations of the at least three external electrodes as a test vector while the external device is not in an active conductive communication session with the IMDs, and use the test vector to search for the advertisement sequences transmitted by the IMDs during an out-of-session (OOS) search window having a first duration;

if the advertisement sequences transmitted by the IMDs are not detected using the test vector during the OOS search window, control the switches to select and use another one of the plurality of different combinations of the at least three external electrodes as the test vector to search for the advertisement sequences transmitted by the IMDs during another instance of the OOS search window having the first duration;

in response the advertisement sequences being detected from the IMDs, establish an active conductive communication session with the IMDs using the test vector that was used to detect the advertisement sequences and determine for the test vector a separate respective score for each of the IMDs; and while the active conductive communication sessions are established with the IMDs, control the switches to use each of other ones of the plurality of different combinations of the at least three external electrodes as the test vector to perform conductive communication with the IMDs during an accelerated search window having a second duration that is shorter than the first duration, and determine for each of the other ones of the plurality of different combinations of the at least three external electrodes used as the test vector during different instances of the accelerated search window a separate respective score for each of the IMDs;

select as a preferred vector, based on the scores, one of the plurality of different combinations of the at least three external electrodes used as the test vector; and perform further conductive communication with the IMDs using the preferred vector.

20. The external device of claim 19, wherein the respective score, determined by the controller for each of the IMDs for each of the plurality of different combinations of the at least three external electrodes used as the test vector, comprises or is based at least in part on a bit score indicative of how well a certain type of bit is conductively communicated using the test vector.

* * * * *